United States Patent
Srinivasan et al.

(10) Patent No.: US 9,308,325 B2
(45) Date of Patent: Apr. 12, 2016

(54) METHODS, DEVICES, AND KITS FOR MICROJET DRUG DELIVERY

(75) Inventors: Ravi Srinivasan, Mountain View, CA (US); Richard C. Urso, Fremont, CA (US); Ameya Kantak, Sunnyvale, CA (US); Christoph Pistor, Mountain View, CA (US); Takashi Yogi, Santa Cruz, CA (US)

(73) Assignee: Corium International, Inc., Menlo Park, CA (US)

( * ) Notice: Subject to any disclaimer, the term of this patent is extended or adjusted under 35 U.S.C. 154(b) by 1003 days.

(21) Appl. No.: 11/820,591

(22) Filed: Jun. 19, 2007

(65) Prior Publication Data

US 2008/0091139 A1 Apr. 17, 2008

Related U.S. Application Data

(60) Provisional application No. 60/805,214, filed on Jun. 19, 2006, provisional application No. 60/805,215, filed on Jun. 19, 2006, provisional application No. 60/822,036, filed on Aug. 10, 2006.

(51) Int. Cl.
*A61M 5/30* (2006.01)
*A61M 5/20* (2006.01)

(52) U.S. Cl.
CPC .............. *A61M 5/30* (2013.01); *A61M 5/2053* (2013.01); *A61M 2005/3022* (2013.01)

(58) Field of Classification Search
CPC ................... A61M 2005/3022; A61M 5/2053; A61M 5/30; A61M 11/06
USPC ............................................. 604/68, 131, 502
See application file for complete search history.

(56) References Cited

U.S. PATENT DOCUMENTS

| | | | | |
|---|---|---|---|---|
| 4,360,019 A | * | 11/1982 | Portner et al. | 604/131 |
| H000150 H | * | 11/1986 | Hankner et al. | 604/890.1 |
| 4,685,903 A | * | 8/1987 | Cable et al. | 604/154 |
| 6,730,060 B1 | * | 5/2004 | Steinbach et al. | 604/131 |
| 7,108,686 B2 | * | 9/2006 | Burke et al. | 604/891.1 |
| 2004/0260234 A1 | * | 12/2004 | Srinivasan | A61M 5/30 604/66 |
| 2006/0122577 A1 | * | 6/2006 | Poulsen et al. | 604/890.1 |

* cited by examiner

*Primary Examiner* — Rebecca E Eisenberg
(74) *Attorney, Agent, or Firm* — Judy M. Mohr; McDermott Will & Emery LLP

(57) ABSTRACT

Described here are methods, devices, and kits for microjet drug delivery. The devices described here may be modular or non-modular. The modular devices typically include a first module having a drug reservoir and a nozzle in fluid communication with the drug reservoir and a second module having an actuator and a power supply. The power supply provides power to the actuator and when the first and second modules are coupled, the actuator is capable of acting on a dispensing member causing it to dispense a drug in liquid form from the drug reservoir via the nozzle at a velocity sufficient to penetrate skin. Other devices described include a nozzle, a reservoir in fluid communication with the nozzle, a dispensing member, and an actuator. In these devices, the nozzle has at least one feature that enhances nozzle contact with the skin in order to reduce lateral drug leakage about the nozzle.

65 Claims, 39 Drawing Sheets

(A-A)

FIG. 26A
FIG. 26B
FIG. 26C
FIG. 26D
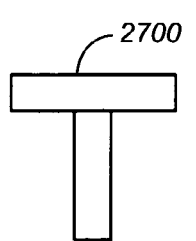
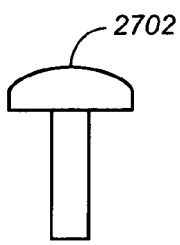
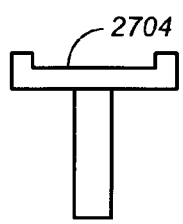
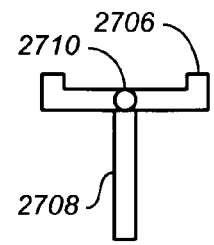
FIG. 27A　FIG. 27B　FIG. 27C　FIG. 27D

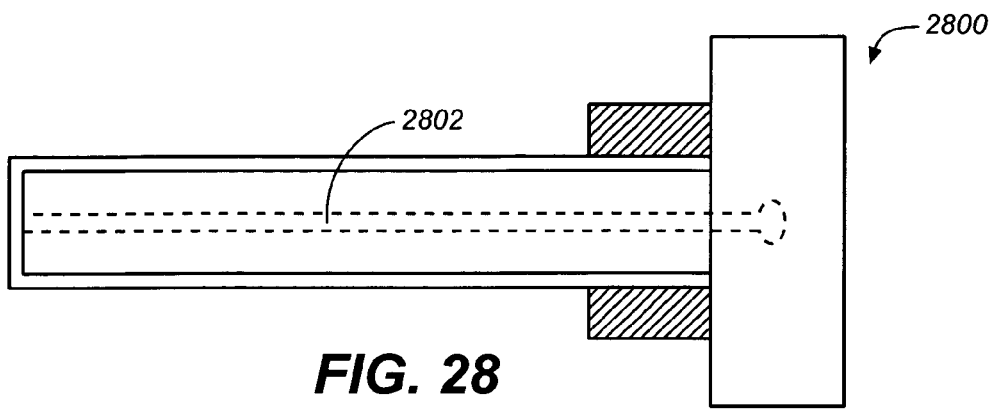
FIG. 28
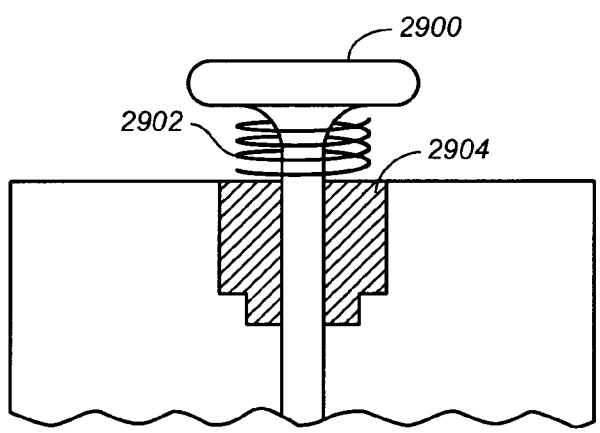
FIG. 29A
      
FIG. 29B   FIG. 29C   FIG. 29D

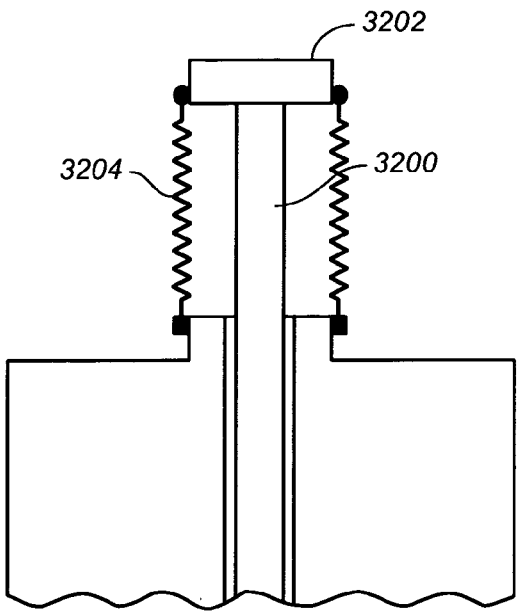
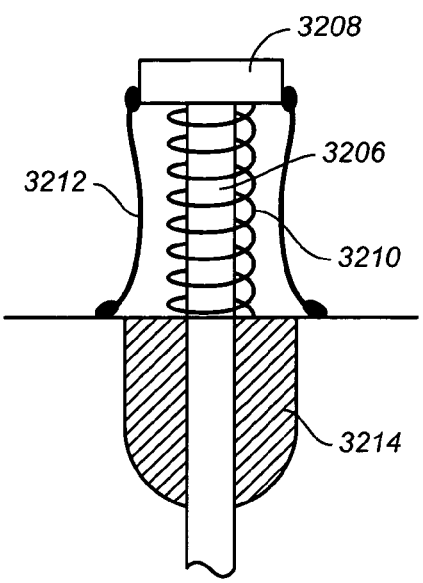
FIG. 32A  FIG. 32B
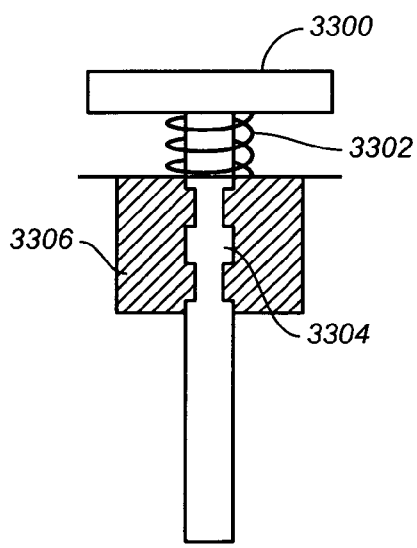
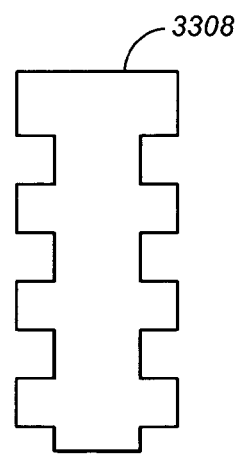
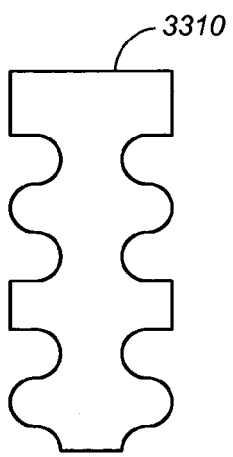
FIG. 33A  FIG. 33B  FIG. 33C

(B-B)

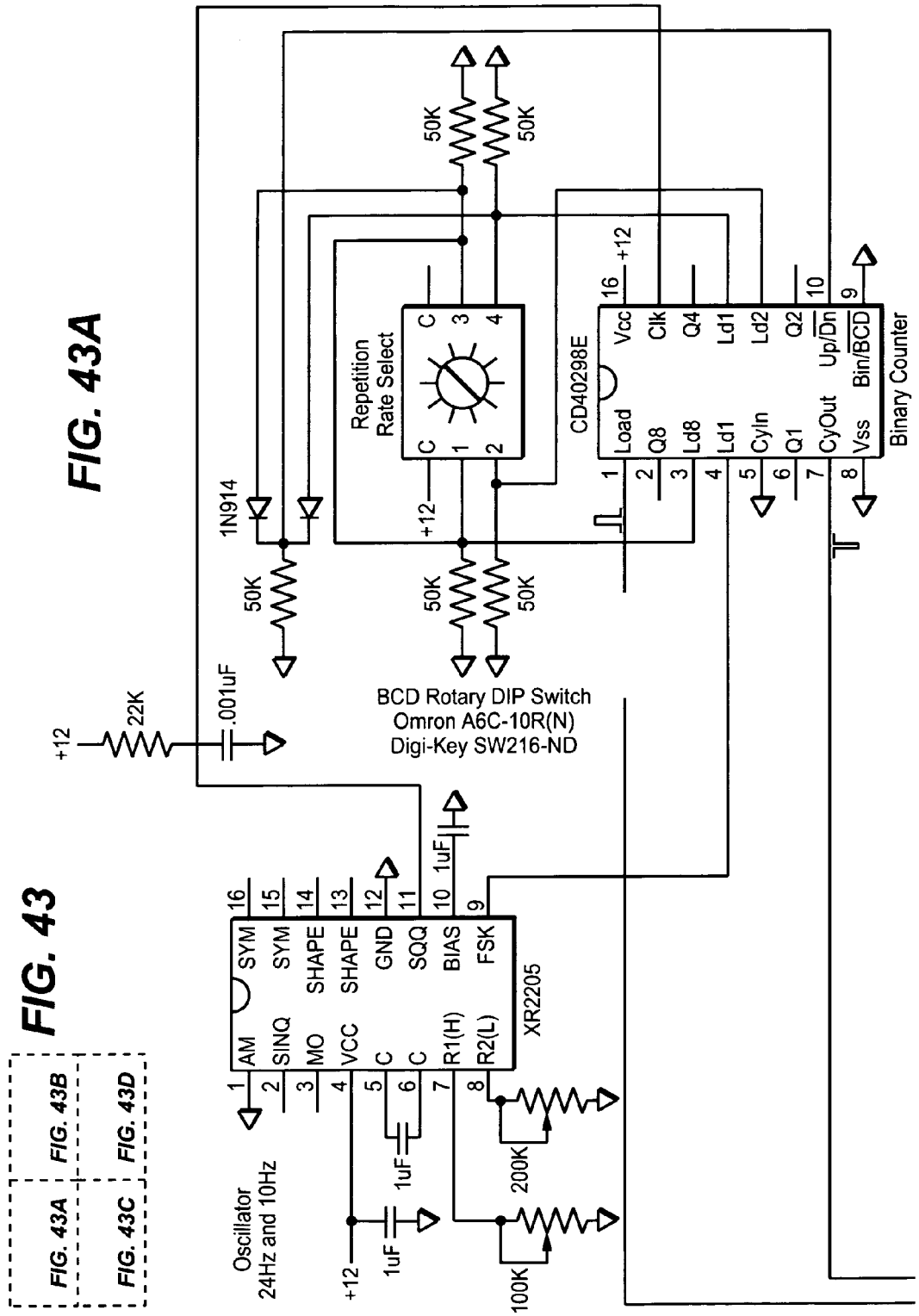

Repetition Role Select Switch Schedule

| Normal Position | Word 8 4 2 1 | Oscillator Frequency | Counter Direction | Function | Counter Output |
|---|---|---|---|---|---|
| 0 | 0 0 0 0 | 10Hz | DOWN | 10/10 | 1 Hz |
| 1 | 0 0 0 1 | 24Hz | DOWN | 24/1 | 24 Hz |
| 2 | 0 0 1 0 | 10Hz | DOWN | 10/2 | 5 Hz |
| 3 | 0 0 1 1 | 24Hz | DOWN | 24/3 | 8 Hz |
| 4 | 0 1 0 0 | 10Hz | UP | 10/(9-4) | 2 Hz |
| 5 | 0 1 0 1 | 24Hz | UP | 24/(9-5) | 6 Hz |
| 6 | 0 1 1 0 | 10Hz | UP | 10/(9-6) | 3 1/3 Hz |
| 7 | 0 1 1 1 | 24Hz | UP | 24/(9-7) | 12 Hz |
| 8 | 1 0 0 0 | 10Hz | UP | 10/(9-8) | 10 Hz |
| 9 | 1 0 0 1 | 24Hz | UP | 24/10 | 2.4 Hz |

*FIG. 43B*

METHODS, DEVICES, AND KITS FOR MICROJET DRUG DELIVERY

CROSS-REFERENCE TO RELATED APPLICATIONS

This application claims priority to provisional patent application U.S. Ser. No. 60/805,214, filed Jun. 19, 2006, provisional patent application U.S. Ser. No. 60/805,215, filed Jun. 19, 2006, and provisional patent application U.S. Ser. No. 60/822,036, filed Aug. 10, 2006, each of which are incorporated herein by reference in their entirety.

STATEMENT REGARDING FEDERALLY SPONSORED RESEARCH OR DEVELOPMENT

This invention was made with United States Government support under 70NANB4H3025 awarded by the National Institute of Standards and Technology (NIST). The United States Government has certain rights in the invention.

FIELD

The methods, devices, and kits described herein are in the field of needleless drug delivery. More particularly, the methods, devices, and kits described herein are in the field of microjet drug delivery across a skin surface.

BACKGROUND OF THE INVENTION

In an effort to minimize the fear, risk, and pain associated with needle injections, several types of needleless methods of drug delivery have been developed. These methods focus on delivering drug through the skin in a variety of different ways (e.g., passive or active diffusion utilizing patches, thermoporation, ultrasound or other energy sources, etc.). However, not all of these methods are effective for delivering all types of drug across and/or through the skin, given its significant and protective barrier function. To be sure, penetrating the skin barrier has proven challenging at times because of its low permeability to foreign molecules, especially large molecules. The main barrier to entry of these molecules is the outermost layer of skin, or the stratum corneum, which consists of densely packed keratinocytes (flat dead cells filled with keratin fibers) surrounded by lipid bilayers, which are highly ordered.

To overcome the barrier function of skin, the present Applicants have developed several microjet injectors that are capable of delivering drugs across the skin surface in a non-invasive fashion, see, e.g., U.S. patent application Ser. Nos. 10/829,888 and 11/367,202 each of which are incorporated herein by reference in their entirety. Other microjet devices have also been described.

Given the advantages microjets offer over standard needleless methods of drug delivery, improvements in the microjet art would be desirable. For example, microjet devices that maximize entry of drug into the skin (or prevent leakage of the drug therefrom) would be desirable. Similarly, microjet devices that are easy to use would be desirable.

BRIEF SUMMARY OF THE INVENTION

Described here are methods and devices for needleless drug delivery. Some of the devices described here are modular in nature and comprise a first module having a drug reservoir and a nozzle in fluid communication with the drug reservoir and a second module having an actuator and a power supply (e.g., a battery or the like). The modules are capable of being releasably coupled to form a modular drug delivery device, and when the first and second modules are coupled, the actuator is capable of acting on a dispensing member causing it to dispense a drug in liquid form via the nozzle at a velocity sufficient to penetrate skin. The modules may be temporarily locked together.

The power supply provides power to the actuator, which may be a piezoelectric actuator, a spring, a solenoid, a magnet, a motor, a compressed gas actuator, or the like. In some variations, the actuator is a piezoelectric actuator, which may or may not be controlled by one or more switches that are operated to apply a voltage pulse to the piezoelectric actuator. The dispensing member may be any suitable dispensing member, such as a plunger, which may have one or more grooves thereon for reducing leakage of drug. The reservoir may be refillable or may instead be configured for a single-use. The device may or may not be programmable, and any portion of the device may be made of a hydrophilic material or be coated with a hydrophilic agent. Having liquid contacting parts of the device be hydrophilic or coated with a hydrophilic agent may be especially useful for reducing bubbles, which may detract from the efficacy of the device, by reducing the velocity of the jet.

The device may be sized and shaped so that it may be worn and operated inconspicuously. For example, the device may take the form of a patch, and is some variations the first module has a basal surface and a top surface and further comprises an adhesive on at least a portion of its basal surface to provide for temporary device attachment to the skin. The second module may further comprise a field programmable gate array, to help with processing and/or programming of the device. The device may further comprise a display, for displaying information such as dosage information, and the like, and/or may further comprise at least one LED. The LED may for example, illuminate to provide some useful indicia of device operation. For example, the LED may indicate that the drug reservoir needs to be refilled, that there is a device failure, that the battery is low, or the like. The device may further comprise a user interface switch or button for allowing the user to control some aspect of the drug delivery.

The device may further comprise at least one element to reduce leakage of drug around the dispensing member, e.g., an O-ring surrounding the dispensing member. One or both modules may further be disposable and configured for a single use. In some variations, the modules are uniquely mateable for a given therapy.

Other devices described here for needleless drug delivery across a skin surface comprise a nozzle, a drug reservoir in fluid communication with the nozzle, a dispensing member, and an actuator. In these variations, the actuator is configured to act on the dispensing member causing it to dispense an amount of drug in liquid form from the nozzle at a velocity sufficient to penetrate skin. In these variations, the device or a portion thereof, comprises at least one feature that reduces leakage of the drug. For example, the geometry of the device (e.g., the nozzle interface) may enhance nozzle contact with the skin in order to reduce lateral leakage of drug. In some variations, the nozzle interface has a plurality of concentric rings formed at least partially thereon.

The device may also comprise at least one element to reduce leakage of drug around the dispensing member (e.g., a plunger or the like). In some variations, the device comprises a flange disposed about at least a portion of the dispensing member. The device may further comprise at least two electrodes to measure capacitance of the skin to help ensure good device contact.

The actuator may be selected from the group consisting of a piezoelectric actuator, a spring, a motor, a solenoid, a magnet, and a compressed gas actuator. In some variations the actuator is a piezoelectric actuator. The device may or may not be programmable, and in some variations the device is programmable. The device may have a basal surface and a top surface and may further comprise an adhesive on at least a portion of the basal surface to provide for temporary device attachment to skin. The device may further comprise at least one noise-reduction element capable of reducing the sound generated by the piezoelectric actuator. The noise-reduction element may, for example, be selected from the group consisting of acoustic foam, sound absorbing silicone, acoustic rubber, a suspension of micro hollow glass spheres, and a combination thereof.

At least a portion of the device may be made of a hydrophilic material or be coated with a hydrophilic agent. The reservoir may be refillable, or be configured for a single-use.

Any of the devices described here may further comprise a flow restrictor that governs the refill flow rate to the nozzle from the reservoir after drug has been dispensed therefrom. The flow restrictor may be any suitable flow restrictor, for example, a fluidic channel having an inner diameter between about 10 and about 200 μm. The device may be configured to deliver an amount of drug between about 5 and about 10 nL. At least a portion of the nozzle may be made from a polymeric material.

Also described here are microjet drug delivery devices for needleless drug delivery across a skin surface comprising a nozzle, a drug reservoir in fluid communication with the nozzle, a dispensing member, and a piezoelectric actuator having an unexpanded state and an expanded stated and configured to act on the dispensing member when in the expanded state, causing it to dispense an amount of drug in liquid form from the nozzle at a velocity sufficient to penetrate skin. In these variations, the piezoelectric actuator is in electrical communication with a capacitor and at least one switch. In some variations, the capacitor has a capacitance that is about 1.5 to about 10 times the capacitance of the piezoelectric actuator, and in some variations, the capacitor is charged to a voltage that is the same or higher than the desired final voltage of the piezoelectric actuator when it is in its expanded state.

The circuit may comprise more than one switch (e.g., a solid state switch), and the switches may or may not be opened or closed at the same time. In some variations, the switches are not closed at the same time. At least one switch is typically used to discharge the piezoelectric actuator to bring the piezoelectric actuator back to its unexpanded state.

In some variations, the piezoelectric actuator is configured to expand within a specified rise-time, be maintained in an expanded position for a specified dwell time, be brought back to its unexpanded state within a specified fall time, and be maintained in the unexpanded state for a specified time, forming a single cycle of operation. The circuit may be operated by any suitable power source, and in some variations it is operated by a battery. The battery may be selected from the group consisting of a lithium ion battery, a zinc-air battery, a lithium manganese oxide battery, a zinc manganese oxide battery, a lithium sulfuryl chloride battery, a lithium polymer battery, a lithium vanadium oxide battery, and a nickel metal hydride battery.

The circuit may further comprise a DC upconversion module. The module may comprise a switching mode power supply (e.g., a boost converter), a charge pump, or the like.

These devices may further comprise a microprocessor, e.g., to control DC upconversion, or the like.

BRIEF DESCRIPTION OF THE DRAWINGS

FIGS. 26A-D provide illustrative plunger tip geometries.

FIGS. 27A-D provide illustrative plunger head geometries.

FIG. 28 shows a plunger variation having a lumen therethrough for refill purposes.

FIG. 29A shows how a spring may be used in connection with the dispensing members described here for recoil purposes.

FIGS. 29B-D illustrate various suitable spring profiles.

FIGS. 30-32B illustrate how various sealing mechanisms may be used with the dispensing members described here.

FIG. 33A-C depict various dispensing members having one or more grooves thereon for aiding with sealing.

FIGS. 43 and 43A-D provide an illustrative schematic of a circuit that generates a pulsed power supply for a piezoelectric actuator powered by a low voltage battery and uses a DC-DC upconverter chip, as shown in FIG. 42.

DETAILED DESCRIPTION OF THE INVENTION

I. Devices

In general, the devices described here are needleless microjet drug delivery devices. That is, they are configured to be worn on the skin of a user and to deliver an amount of drug through the skin by way of a high-speed microjet. Accordingly, the devices described here typically comprise a reservoir for housing a drug (e.g., in liquid form), a dispensing mechanism, to dispense the drug via a nozzle, and an actuator, which when actuated, causes the dispensing mechanism to dispense the drug.

The devices may be configured for any type of attachment to the skin, and in some instances it may be desirable that the device be configured for relatively inconspicuous wear. For example, the devices described here may be configured as a patch for attachment to the skin, a watch, an armband, or the like. In some variations, which will be described in detail below, the devices described here are configured for use in a patch-like fashion. The devices may further comprise a user interface button or switch to allow for partial or total user operation and control. Similarly, the devices may further comprise one or more displays (e.g., to display device or dosing information or the like), one or more alarms (e.g., audible, tactile, vibratory, or the like, to warn the user of a potential problem), one or more LEDs (e.g., which may illuminate under various circumstances to provide some sort of system indication), or the like. Each of these components will be discussed in more detail below. The devices may also comprise two electrodes to measure capacitance of the skin, in order to help ensure proper contact of the device with the skin.

Some, but not all, of the devices described herein are modular in nature. That is, they comprise at least two modules that releasably couple together to form a single operable device. Modular devices may be particularly useful for long-term therapy sessions in that component pieces are easily accessible. In addition, one or more of the modules may be partially or entirely disposable. In some variations, the modules are uniquely mateable with one another. That is, in some variations, a first module may only be mateable with a single and specific type of second module. Having modules that are uniquely mateable may help prevent accidental or abusive drug dosing. It should be noted, that while the devices described herein, are typically needleless in fashion, the modular devices just described may also be used with certain needle type injectors/designs known in the art (e.g., infusion and/or insulin pumps). The modular nature (even with a needle type design) would offer the advantage of reduced cost, etc.

Figure 1A:
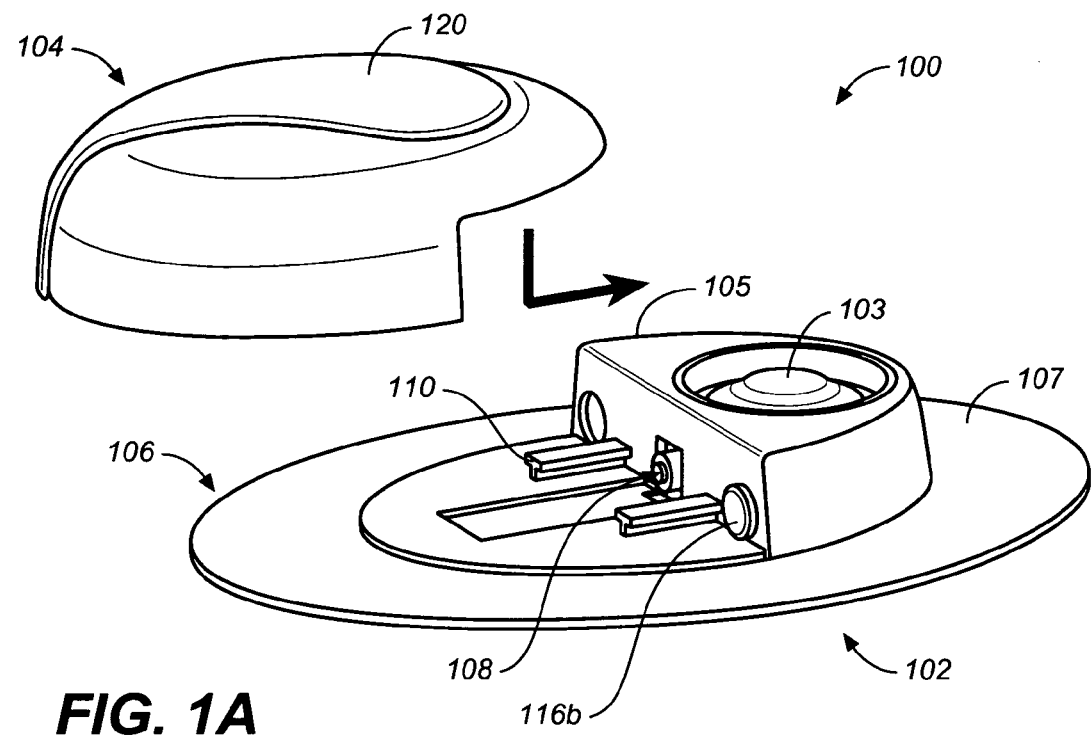
FIG. 1A provides an illustrative variation of a modular drug delivery device described herein.

One example of a modular drug delivery device is shown in FIGS. 1A-1D. As shown in FIG. 1A, device (100) comprises a first module (102) having a drug reservoir (103) and a nozzle in fluid communication with the drug reservoir (not shown in this view), and a second module (104) comprising an actuator and a power supply (not shown in this view). The first (102) and second modules (104) are capable of being releasably coupled (as shown by the arrow) to form a modular drug delivery device (100). When the first (102) and second (104) modules are coupled, the actuator is capable of acting on a dispensing member causing it to dispense a drug in liquid form from via the nozzle at a velocity sufficient to penetrate skin (e.g., from about 5 m/s to about 100 m/s, or from about 10 m/s to about 30 m/s).

The device (100) of FIG. 1A is configured for wear as a patch. As shown in FIG. 1A, first module (102) has a top surface (105) and a basal surface (107). The basal surface (107) has an adhesive (106) on at least a portion thereof to provide for temporary device attachment to the skin. Pressure sensitive adhesives are well known in the transdermal patch and wound-healing arts and any suitable wound-healing or transdermal patch adhesive may be used. In general, the adhesive should provide for adhesion of the device for the entire duration of the particular drug delivery therapy and should provide adhesion for that duration notwithstanding the weight of the device. Exemplary adhesives may be polysiloxane, polyisobutylene, or polyacrylate based, or the like, and in one variation the adhesive is a polyacrylate adhesive. Illustrative adhesives are 3M-1774W (foam adhesive) and 3M-9877 (transfer adhesive) manufactured by 3M Corporation.

Figure 2A:
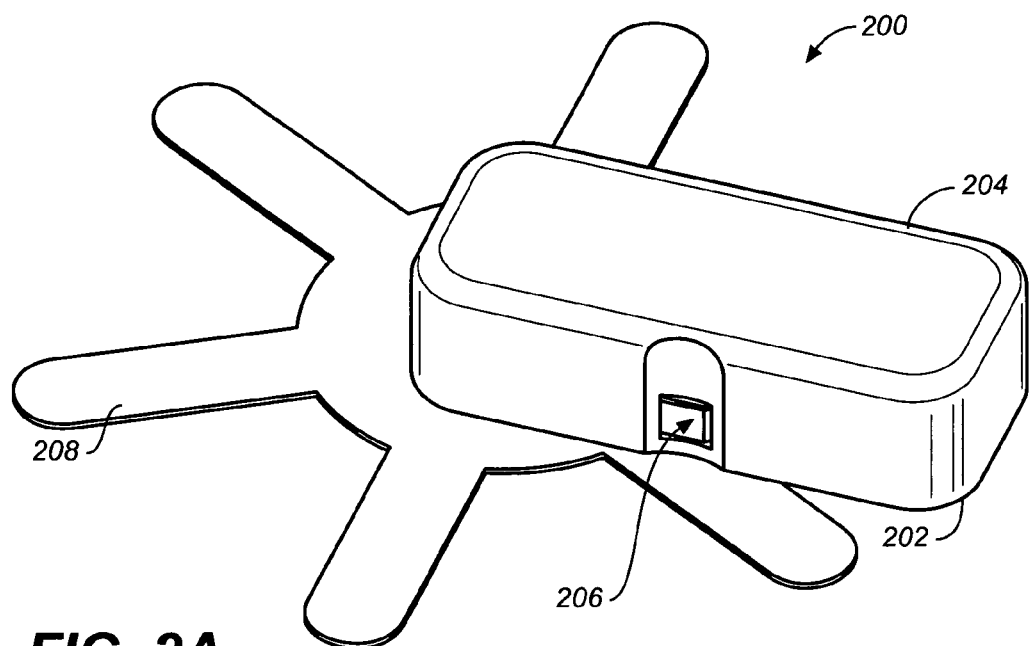
FIGS. 2A-2D depict how the modular drug delivery devices described here may be temporarily locked together.
Figure 2B:
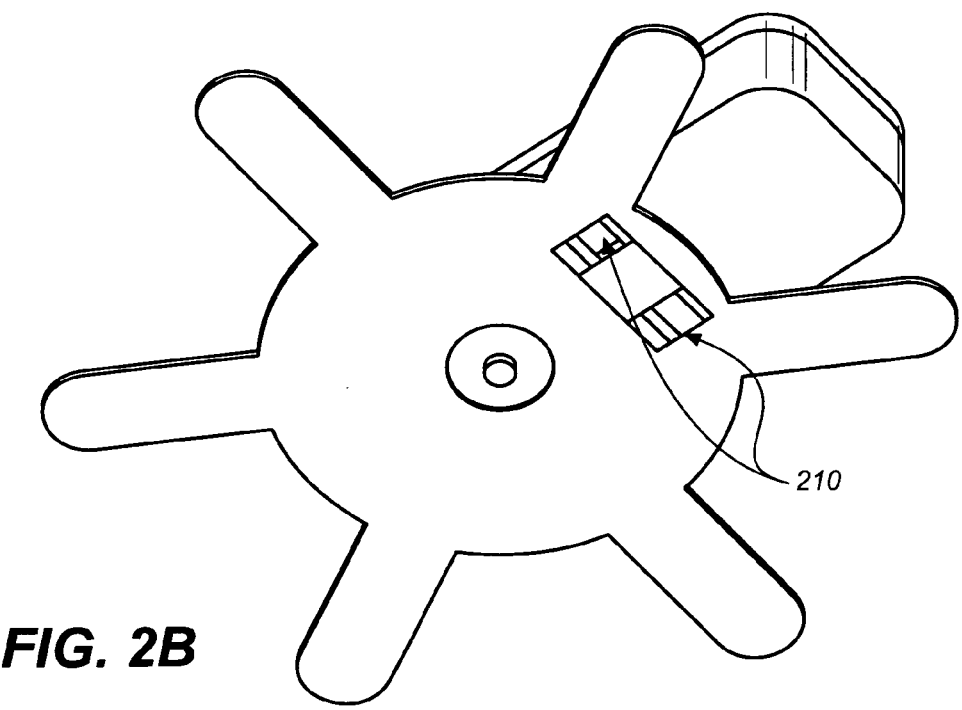
Figure 2C:
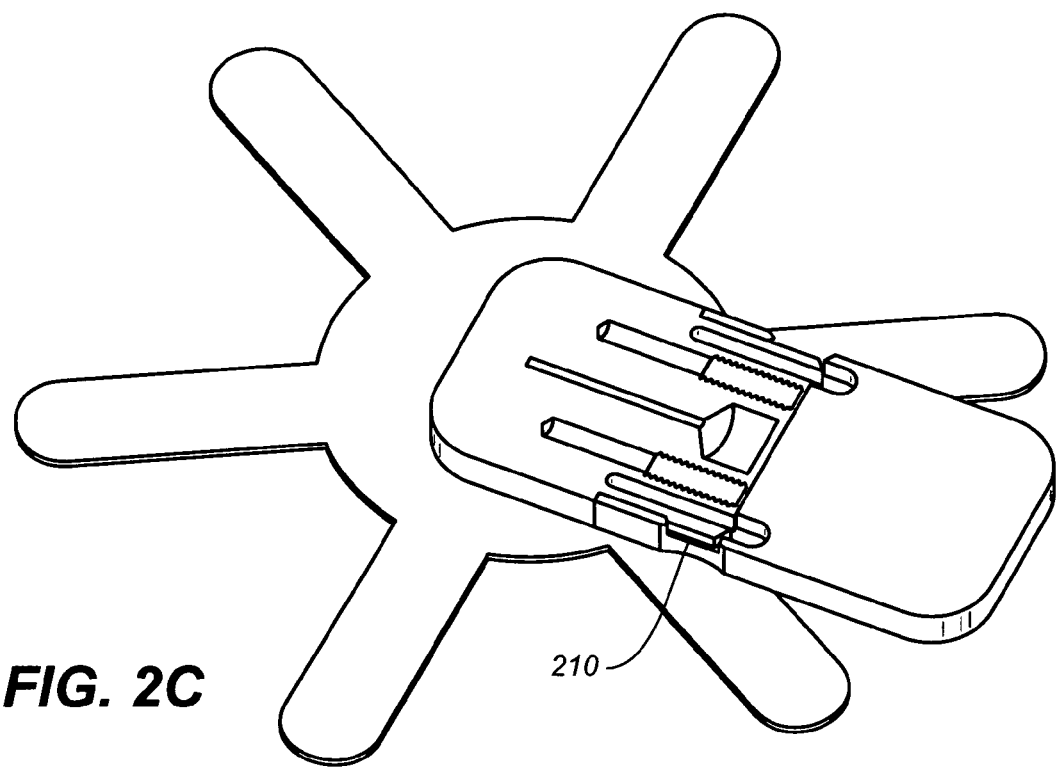

It is important to note that while the adhesive shown in FIG. 1A is generally elliptical in nature and covers entire basal surface (107) of first module (102), such an adhesive geometry is not necessary. The adhesive may have any suitable or desirable shape, may have one or more apertures therein, and may or may not cover the entire basal surface of the first module or device. For example, FIGS. 2A-2C provide an illustrative example of an adhesive surface (208) that has finger-like projections.

Referring back to FIG. 1A, also shown is user interface button (120), dispensing member (108), and sliding keyways (110), which serve to guide the coupling of first (102) and second (104) modules in a monorail fashion. The reservoir (103) is enclosed by a diaphragm (depicted more clearly as 109 in FIG. 1D). The user interface switch or button (120) may be used to allow the user to operate some aspect of the device, for example, dosing. When depressed by the user, the switch can trigger the actuator, which in turns leads to dispensing of a dose of drug.

Figure 1B:
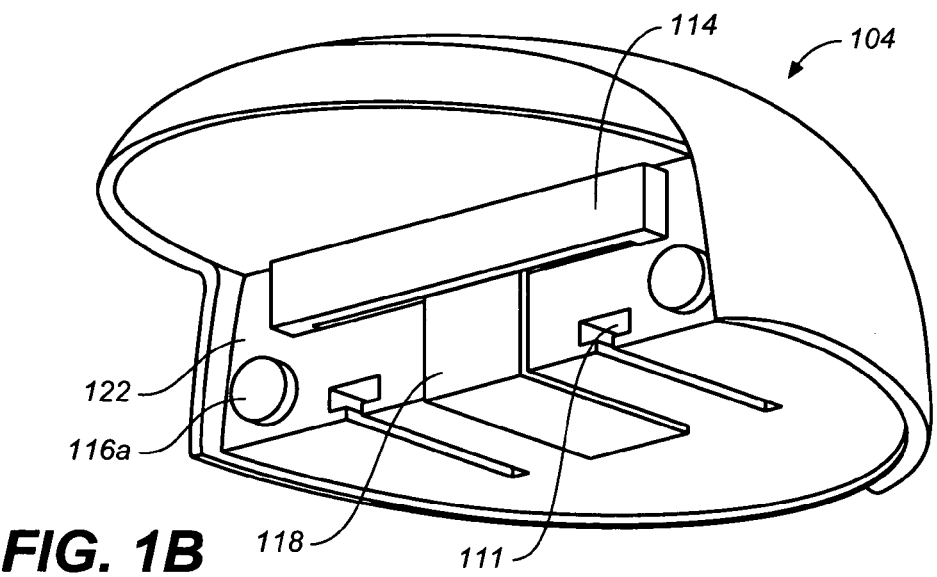
FIG. 1B shows an illustrative variation of a second module used with the modular drug delivery devices described herein.

FIG. 1B shows a close-up view of second module (104). Shown there is power source (114), here depicted as a removable battery held in a battery tray. The power source may be any suitable source, and in instances where a battery is used, the battery may or may not be rechargeable. Also shown in FIG. 1B are sliding keyways (111) which correspond to sliding keyways (110) on first module (102), for module coupling. Magnets (116a) are shown in this variation for further securing or locking the modules together after they have been coupled. In this variation, magnets (116a) are magnetically coupled to metal plates (116b). It should be understood that magnets (116a) may be on either the first (102) or second (104) module. Additional locking mechanisms will be discussed in more detail below with reference to FIGS. 2A-2D.

Figure 1C:
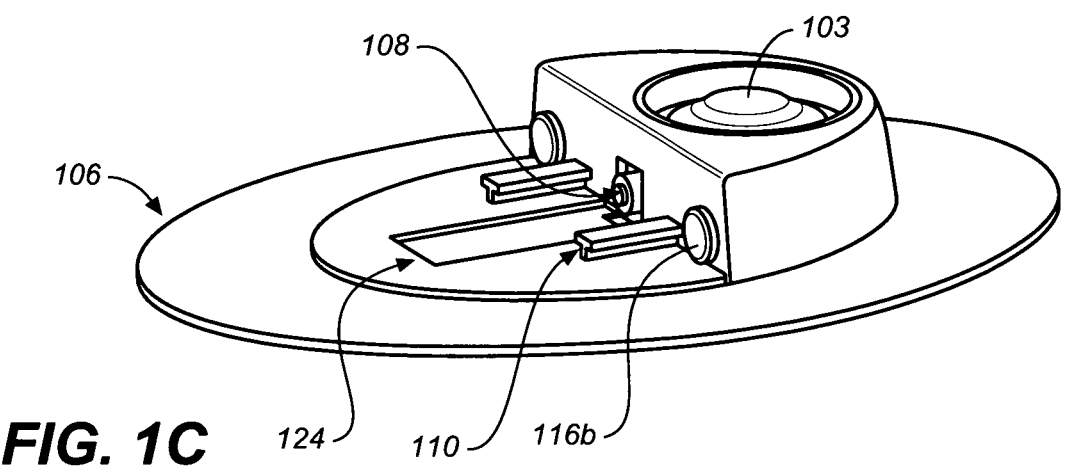
FIG. 1C shows an illustrative variation of a first module used with the modular drug delivery devices described herein.
Figure 1D:
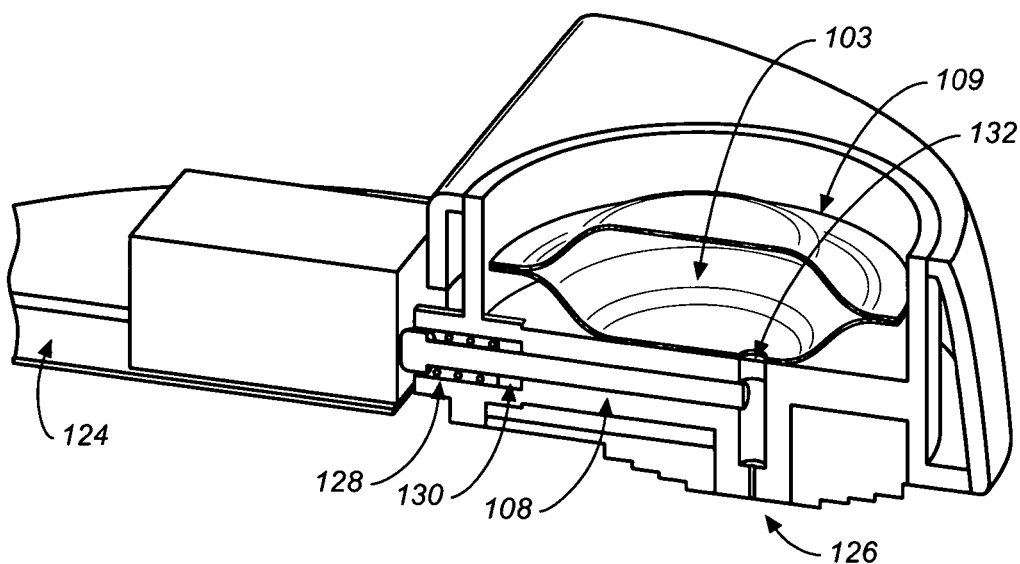
FIG. 1D provides a partial cross-sectional view of a first module.

FIG. 1C provides a close-up view of first module (102), showing the components identified in FIG. 1A in more detail, while FIG. 1D provides a partial cross-sectional view of the first module (102). As shown there, the first module (102) comprises a drug reservoir (103) for containing an amount of drug, most typically, in liquid form. However, the drug may be in any suitable dispensing form in the reservoir (e.g., a suspension, an emulsion, a solution, a mixture, a dispersion) and may or may not contain some solid particles. In this variation, the reservoir (103) is enclosed by a diaphragm (109), such as any of those diaphragms described below. Also shown is dispensing member (108) having a spring (128) for recoil and seal (130) about a portion of the dispensing member (108) to help reduce or prevent drug leakage. Also shown is a flow restrictor, here shown as a microfluidic channel (132). Each of these components will be described in substantial detail below.

While modules (102) and (104) are depicted throughout FIGS. 1A-D as having a particular geometry, the modules may have any suitable or desirable geometry. For example, a modular drug delivery device having a generally rectangular shape is shown in FIGS. 2A-2D. The modules may also be made from any suitable material, but surfaces in contact with the drug should be made from a drug compatible material (i.e., the material should not erode or otherwise degrade in the presence of the drug and should not leach into the drug or alter the drug properties). In some variations, the modules are made from a combination of plastics. The modules may have any appropriate size. For example, the footprint of either the first or second module may be from about 0.5 cm×0.5 cm to about 3 cm×3 cm. The height of either the modules may be from about 1 mm to about 3 cm, for example.

The modular drug delivery devices described herein, as noted briefly above, may also comprise any number of additional features or components. For example, the devices may comprise a mini-monitor or window display, to display certain information to the user, such as drug information, dosage information, delivery information, warnings, and the like. The display may also display certain information not directly relevant to the therapy, such as date and/or time of day. The devices may also comprise one or more LEDs. For example, the device may contain an array of LEDs, each illuminating in a different color for providing an indication of some aspect of the device operation. For example, an LED may illuminate to indicate that the drug reservoir is empty. Similarly, an LED may illuminate to indicate that the battery is low or that there is a device malfunction or failure. In a like fashion, a LED may illuminate to indicate a general warning about the dosing of the drug. The devices may also comprise two electrodes to measure skin capacitance.

The modules may be locked together in their coupled state as shown in FIGS. 2A-2D to help prevent separation and dosing failure or other problems due to poor module coupling. FIG. 2A shows a modular drug delivery device (200) comprising a first module (202) and a second module (204) temporarily locked by latches. Latch button (206) for releasing the latch is shown. A corresponding latch button may be present on the other side of the device (200) as well. In this variation, the modules are released or disengaged when the latch button (206) is depressed and the modules are pulled apart from one another. Also shown in FIG. 2A is an adhesive (208) having finger-like projections that extend radially outward from a center portion. This type of adhesive geometry may be advantageous in that it may help to ensure sufficient nozzle pressure and contact against the skin, when the fingers are pulled and attached to the skin surface in a tight and secure manner.

Figure 2D:
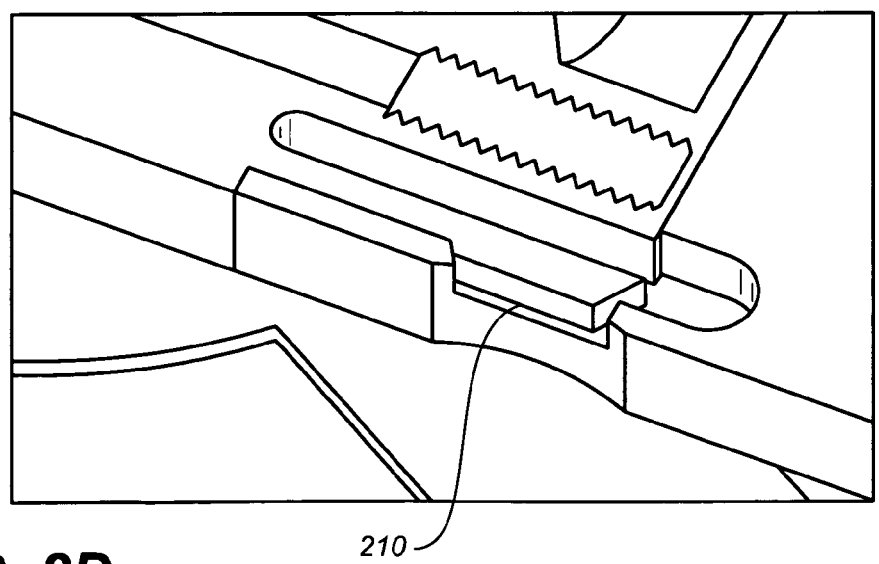

The latches for locking the device may be positioned at any convenient and operable location, and FIG. 2B shows a variation where the latches (210) are on the bottom of the device. FIG. 2C shows an internal view of a device having bottom-locking latches (210) and FIG. 2D shows a close-up view of this design. While latches have been disclosed and shown in some detail, it should be understood that any suitable locking mechanism may be used with the modular drug delivery devices disclosed here. For example, the modules may be temporarily locked together via magnets (as shown in FIG. 1A), via screws or other mechanical fasteners, or may be snap-fit together. In some variations, the modules are permanently locked together.

While modular drug delivery devices were just described in some detail above, not all the devices described herein are modular in nature. Indeed, in some variations, the device is a single unit, which may or may not be entirely disposable. The following device components may be used in either modular or non-modular drug delivery devices.

A. Nozzles

Figure 3A:
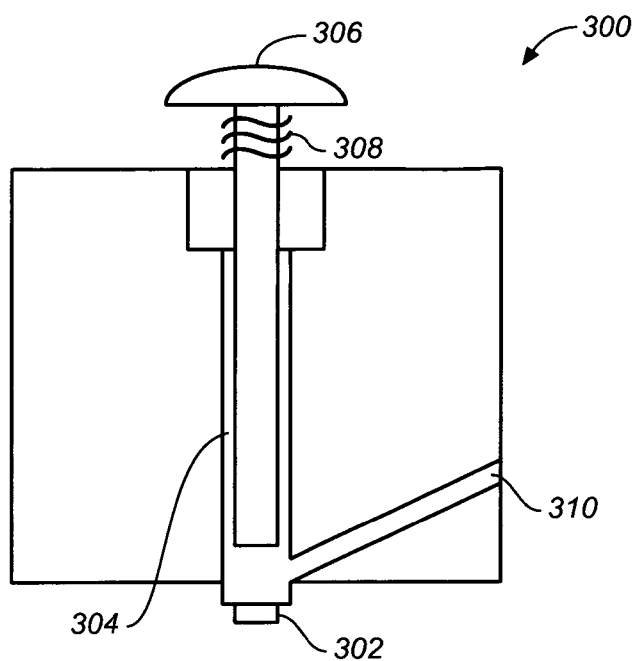
FIG. 3A depicts a portion of a suitable drug delivery device described here where the nozzle is in an axial relationship to the barrel.
Figure 3B:
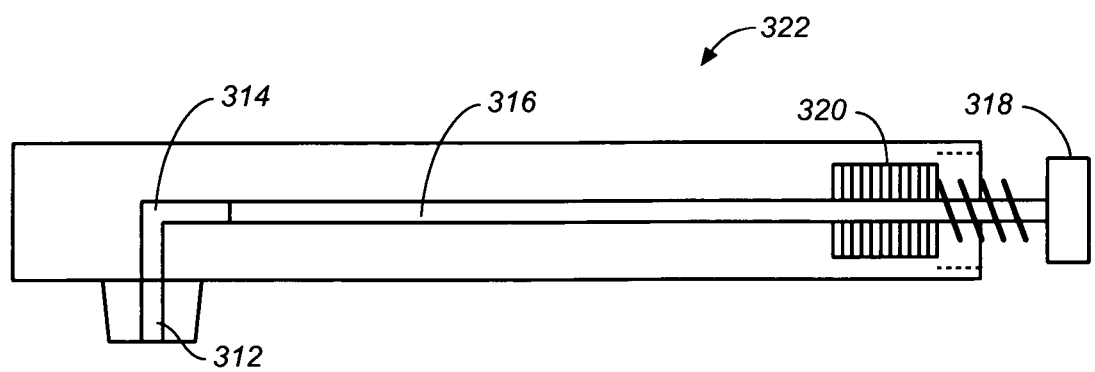
FIG. 3B depicts a portion of a suitable drug delivery device described here where the nozzle has a 90° bend adjacent to the barrel.

The devices described herein typically comprise one or more nozzles, through which the drug is ejected. The nozzle is in fluid communication with a drug reservoir, which typically houses a drug to be dispensed in liquid form. Reservoirs, dispensing members, and illustrative drugs will be discussed in more detail below. Exemplary illustrations of various portions of drug delivery devices are shown in FIGS. 3A and 3B. Shown in FIG. 3A is a portion of device (300). FIG. 3A shows nozzle (302) in fluid communication with a barrel (304), and dispensing member (306), here shown as a plunger having spring (308) for recoil. Also shown is a refill sideport (310) for refilling the barrel (304) with additional drug.

Figure 3C:
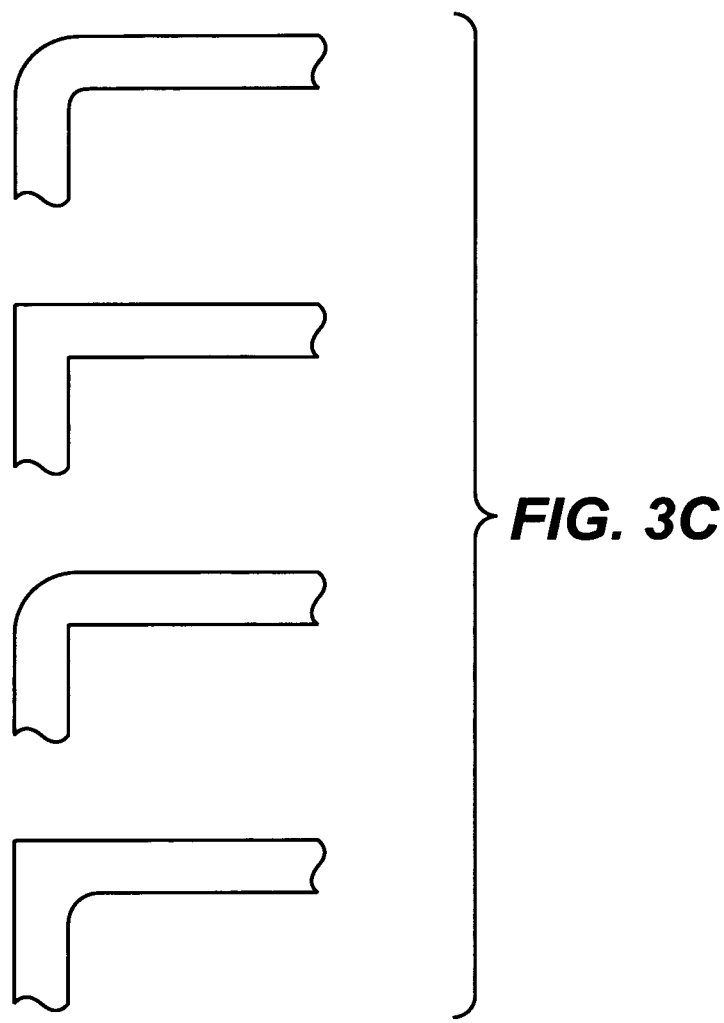
FIG. 3C depicts illustrative nozzle bend geometries.

The barrel may be in fluid communication with a reservoir (not shown), or may be the reservoir itself. In this variation, the nozzle is positioned in an axial relationship (i.e., a 180° angle) with respect to the barrel (304). Any desirable angle may be used. For example, the nozzle (312) of device (322) shown in FIG. 3B has a bend having a 90° angle (314) adjacent to barrel (316). The nozzle (312) is in fluid communication with barrel (316). Dispensing member (318), shown here as a plunger, is used to dispense drug out of barrel (316) via nozzle (312). Also shown in FIG. 3B is a seal or plug (320) that may be disposed about at least a portion of the dispensing member to help prevent leakage of drug. The seal or plug may be any suitable seal, for example, a silicone seal. Additional seals and sealing techniques about will be described in more detail below when reference is made to the dispensing member. It should be appreciated that the bend of the angle shown in FIG. 3B need not have two straight edges as shown there. For example, one or both edges of the bend may also be rounded as shown in FIG. 3C.

Figure 3D:
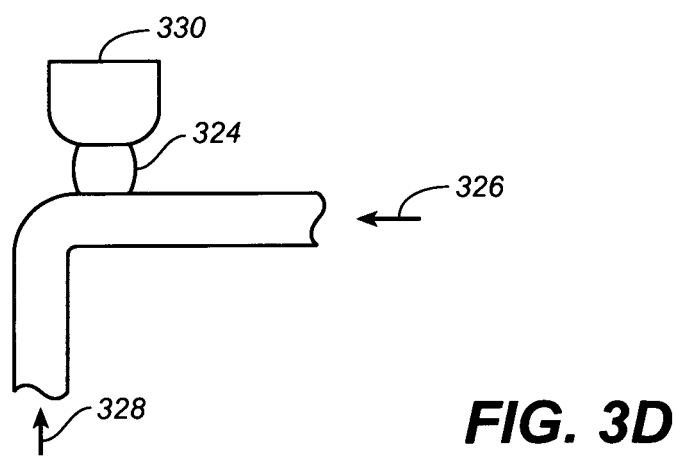
FIGS. 3D-3F demonstrate how a nozzle having a 90° bend may be made.
Figure 3E:
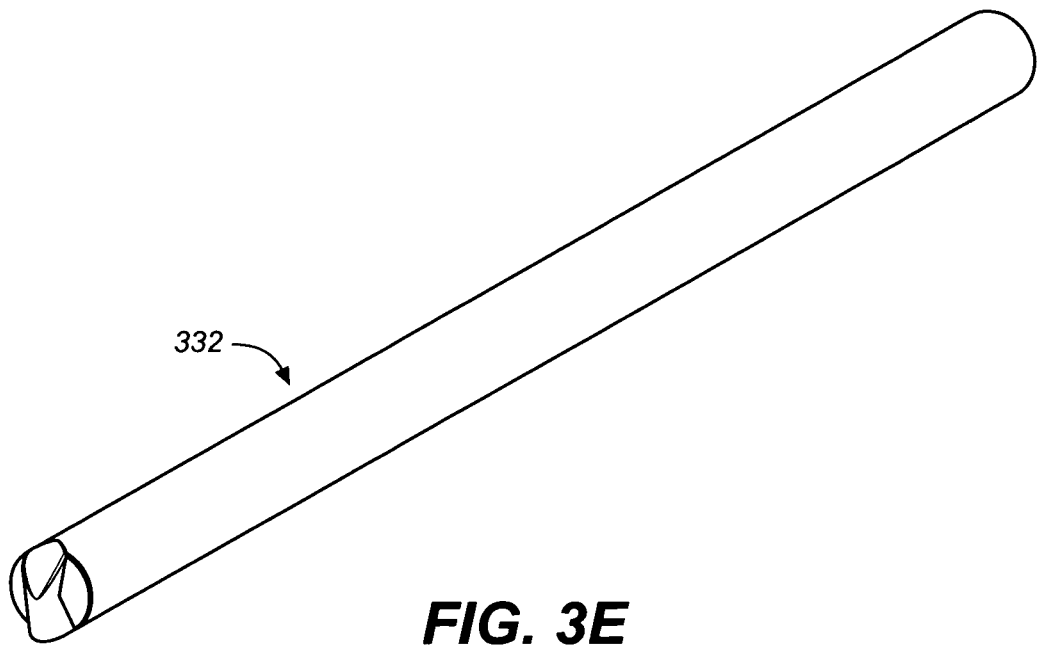
Figure 3F:
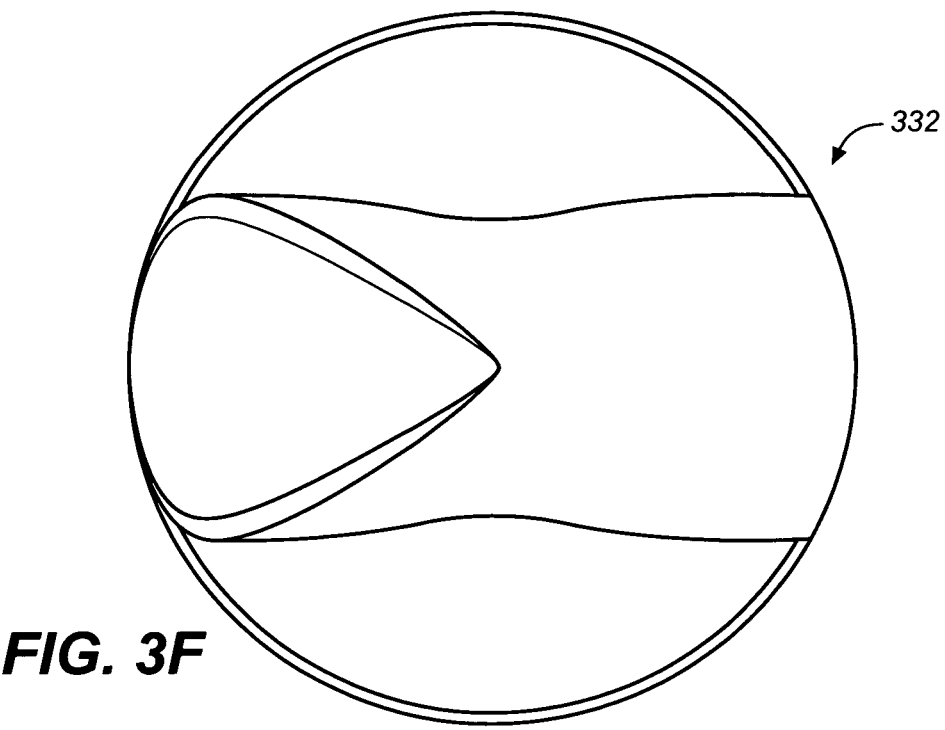

An illustrative method of making a nozzle having a generally 90° angle will now be described with reference to FIGS. 3D-F. Shown in FIG. 3D is nozzle piece (324) that has been constructed by drilling horizontally to create a first lumen (326) and drilling vertically to create a second lumen (328). Backfill hole (330) is used to fill the hole left by the second vertical drilling procedure. Prior to filling backfill hole with an epoxy or other suitable plugging material, a pin is placed into either the first or second lumen as the case may be, to block the flow of epoxy at the 90° angle intersection. An illustrative pin (332) for such a procedure is shown in a side-view in FIG. 3E and a front view in FIG. 3F.

It is important to note that while FIG. 3A illustrated a single refill port close to the nozzle of the device, any number of refill ports at any suitable location may be used. For example, the refill ports may be located closer or further from the reservoir and/or plunger. In some variations, multiple refill ports are used.

Figure 4A:
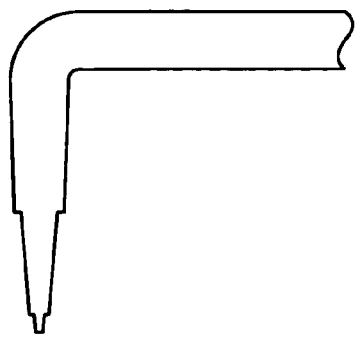
FIGS. 4A and 4B depict a nozzle having a stepped diameter reduction leading to the nozzle opening, and a gradual diameter reduction leading to the nozzle opening respectively.
Figure 4B:
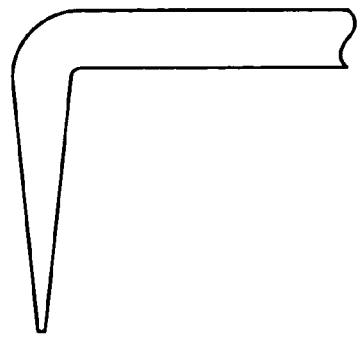

FIGS. 4A and 4B depict side views of various nozzle designs where there is a diametrical size reduction in the nozzle leading to the nozzle opening. In FIG. 4A the reduction occurs in a series of discrete steps. In FIG. 4B, the reduction is gradual.

As mentioned briefly above, any part of the devices described here may be made from a hydrophilic material, be coated with a hydrophilic agent, or be impregnated with, or otherwise comprise, a hydrophilic agent. Suitable hydrophilic agents include, but are not limited to polyethylene glycol (PEG), polyethylene oxide (PEO), polyethylene oxide-polypropylene oxide (PEO-PPO), dextran, polyetherimide (PEI), ethylhydroxyethylcellulose, PEG-derived polymers, polyacrylic acid (PAA), poly-L-lysine (PLL), poly(allylamine hydrochloride (PAH), poly(styrenesulfonate) (PSS), poly(dimethyl-ammoniumchloride) (PDDA), other polyelectrolytes, and the like. In some variations, PEG is used (e.g., by surface adsorption). When at least a portion of the fluid contacting surfaces are hydrophilic (e.g., the nozzle, the reservoir, refill port, plunger, etc.), bubble formation and surface adsorption of drug molecules may be reduced. The hydrophilic agent or material may be coated or bonded to the device my any suitable technique (e.g., spray-coating, dip-coating, physical or chemical bonding or grafting with or without prior surface activation with a plasma, or the like).

Figure 5A:
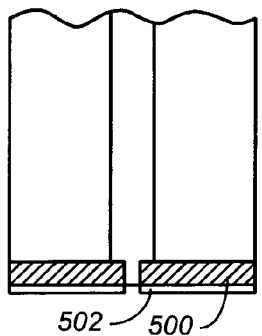
FIGS. 5A-C depict variations where a hydrophilic ring is used about the nozzle.
Figure 5B:
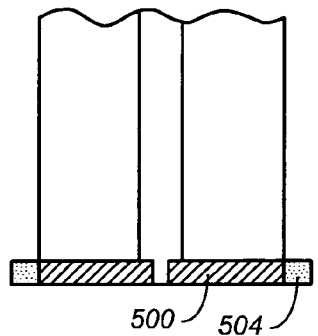
Figure 5C:
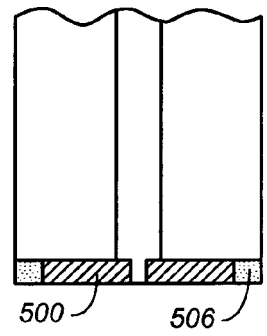

In some variations, the devices comprise a hydrophilic ring (e.g., a hydrophilic adhesive retainer ring) about at least a portion of the nozzle as shown in FIGS. 5A-5C. These figures depict how a hydrophilic ring may be coupled to the device. In FIG. 5A, hydrophilic ring (500) is coupled to the device using an adhesive (502). In FIG. 5B, the hydrophilic ring (500) is coupled using an outer ring (504), and in FIG. 5C, the ring (500) is coupled using a transfer tape (506). Hydrophilic ring (500) may also be a porous hydrophilic sheet, membrane, or other suitable thin film, e.g., a hydrophilic sheet made by Porex.

Figure 6A:
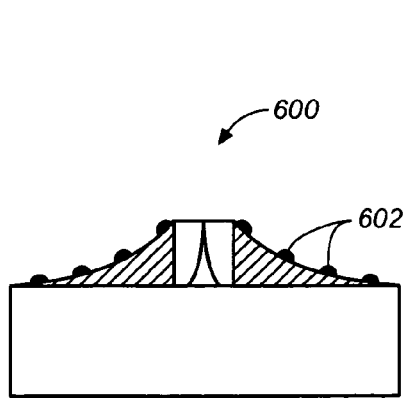
FIGS. 6A and 6B provide side and top views respectively of a nozzle portion having concentric rings thereon.
Figure 6B:
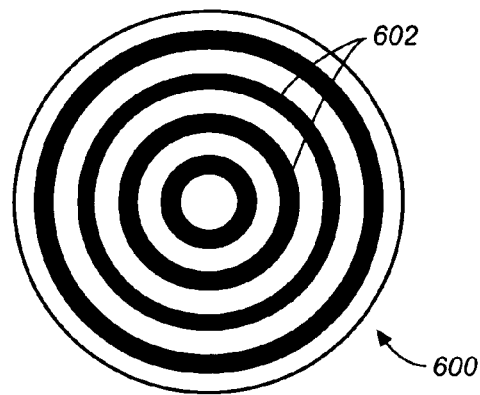

In some variations, the device, or a portion thereof, has at least one feature that enhances nozzle contact with the skin in order to reduce lateral leakage of drug about the nozzle. For example, the feature may the geometry of a portion of the device. In some variations, the portion of the device adjacent to the nozzle (i.e., the nozzle interface area) comprises a series of concentric rings or circles about at least a portion its surface in order to improve the seal between the skin and the nozzle and thus reduce lateral leakage of drug about the nozzle. This variation is shown in FIGS. 6A and 6B. FIG. 6A shows a side view of distal tip of nozzle interface (600) having a series of concentric rings (602) thereon. FIG. 6B shows a top view of the same nozzle interface (600). Any suitable number of concentric rings may be used, and the rings may be formed of the same or different material from the rest of the nozzle interface. In some variations, the nozzle is made from a polymer, such as a silicone or urethane polymer, and in some variations, the concentric rings are also formed from a polymer, such as a silicone or urethane polymer.

Figure 7A:
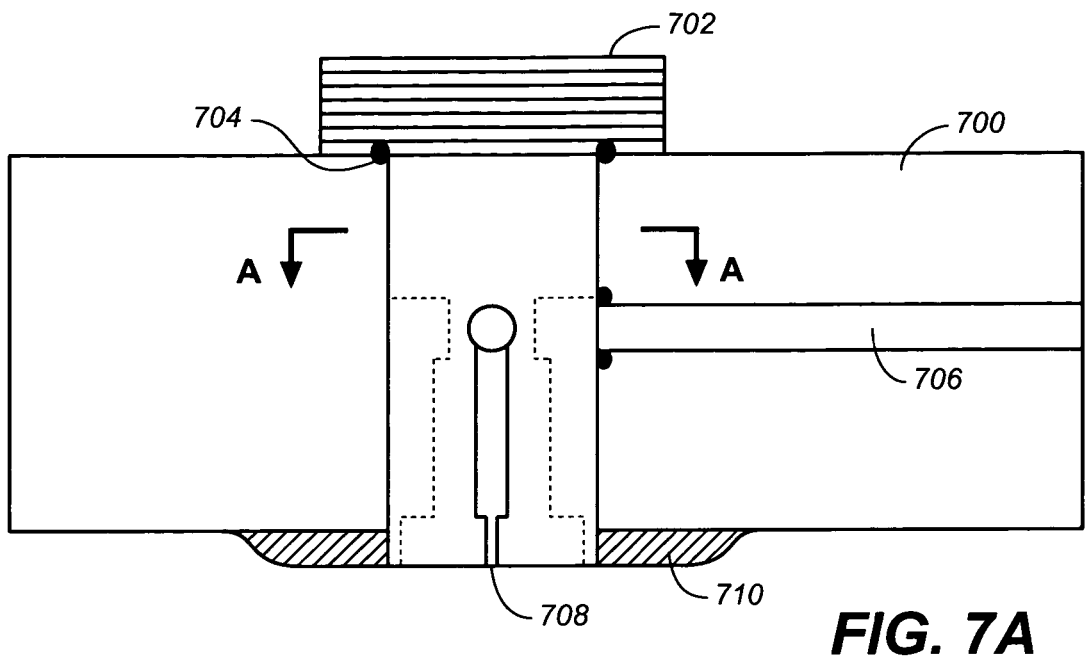
FIGS. 7A-7C provide illustrative variations of how the nozzle diameter may be varied.
Figure 7B:
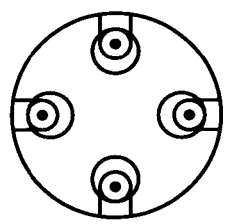
Figure 7C:
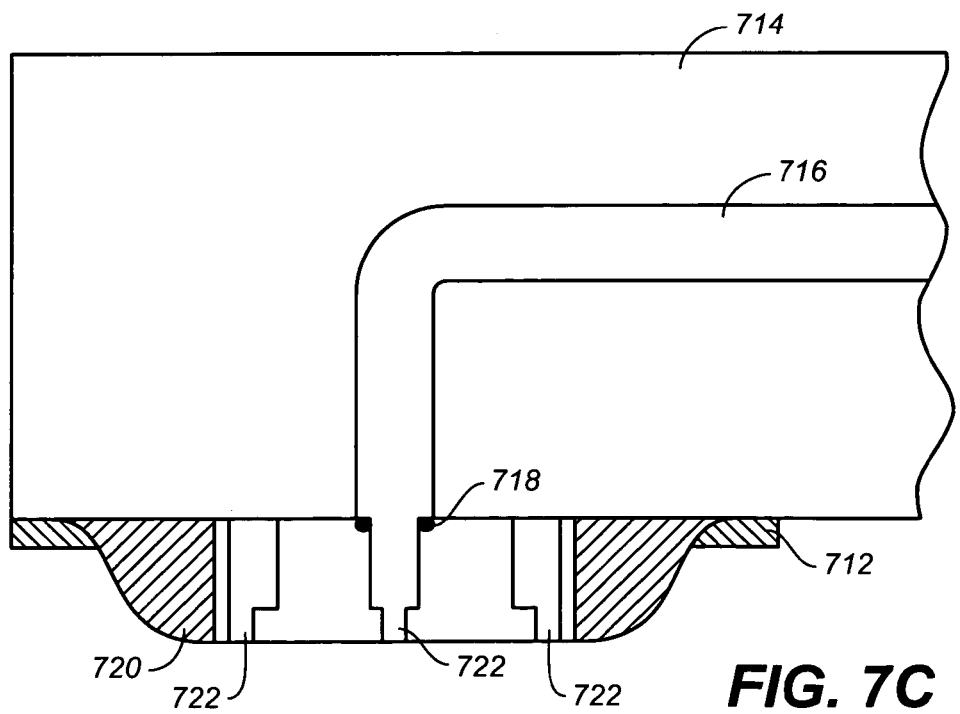

The nozzle may also be configured to provide for a variable diameter of its distal opening. For example, it may be desirable to change the diameter of the nozzle opening depending on the type of drug to be delivered, the dosing regime of the drug, or the like. In this way different preset volumes of drug may be delivered to the user. FIGS. 7A and 7C illustrate two different variations of an adjustable nozzle. Shown in FIG. 7A is nozzle body (700), variable nozzle selection dial knob (702), seal or bushing (704), barrel (706), nozzle tip (708), and skin-nozzle interface (710). In FIG. 7A, the diameter of the nozzle may be changed by turning or rotating dial (702). A top view taken along line A-A is shown in FIG. 7B. In FIG. 7C, the diameter of nozzle is changed by turning or rotating a selector wheel (712) located adjacent to nozzle tip. In this way, the diameter may be variable and selectable as needed or desired. Shown in FIG. 7C is nozzle body (714), barrel (716), selector wheel (712), bushing or seal (718), skin-nozzle interface (720), and adjustable nozzles (722).

Figure 8A:
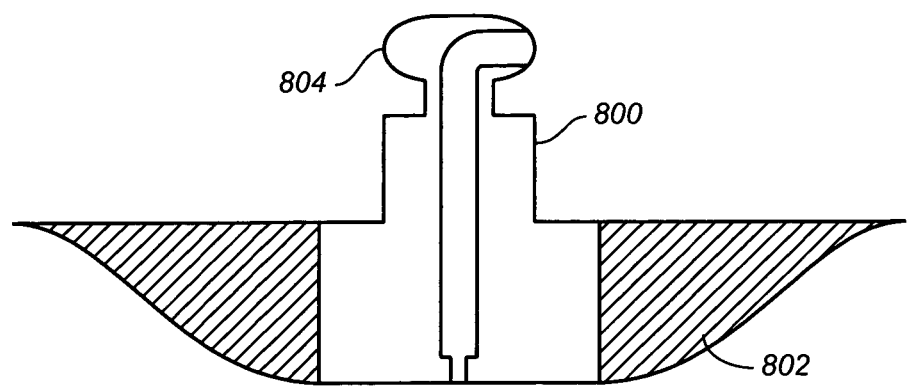
FIGS. 8A and 8B show how a nozzle may be removable and interchangeable.
Figure 8B:
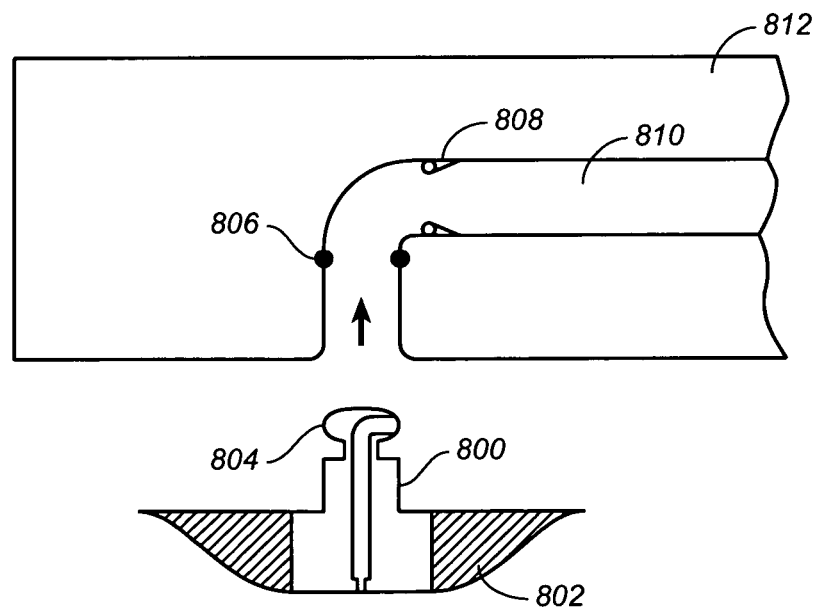

The nozzle may also be constructed in a modular fashion so that it is interchangeable with other nozzles as shown in FIGS. 8A and 8B. Shown in FIG. 8A is nozzle unit (800), skin-nozzle interface (802), and snap locking lugs (804), for coupling with rubber seal bushings (806). As shown in FIG. 8B, the nozzle unit (800) may be advanced into proper position within nozzle body (821). Also shown in FIG. 8B are rubber seal bushings, nozzle-plunger interface seals (808), and barrel (810). The nozzles may be snap-fit or otherwise configured for attachment to the devices described here. This may be desirable for quick interchange when changing between different dosing regimes, different drugs, or the like, or may be desirable if a nozzle is clogged, damaged, or otherwise needs to be replaced.

Again, it should be understood that any number of nozzles may be used as desirable. The nozzles may all have the same geometry, size, overall configuration and the like, or the nozzles may be different in one or more aspects. The nozzles may be positioned in an orderly array, or may be placed variously throughout the device where useful or convenient.

B. Reservoirs

The reservoirs for use with the devices described here typically house the drug to be dispensed in liquid form. The reservoir may be refillable, for example, via the use of a refill port (such as those briefly described above), or may be configured for a single use. When the reservoir has only a single dose or single therapy amount of drug therein, the reservoir, or in the case of a modular device, the first module comprising the reservoir, may be discarded. The reservoir may be any desirable geometry, and in some variations, it may be desirable to choose a reservoir geometry that is easily machinable or moldable, such as a circle, rectangle, ellipse, or the like.

Figure 9A:
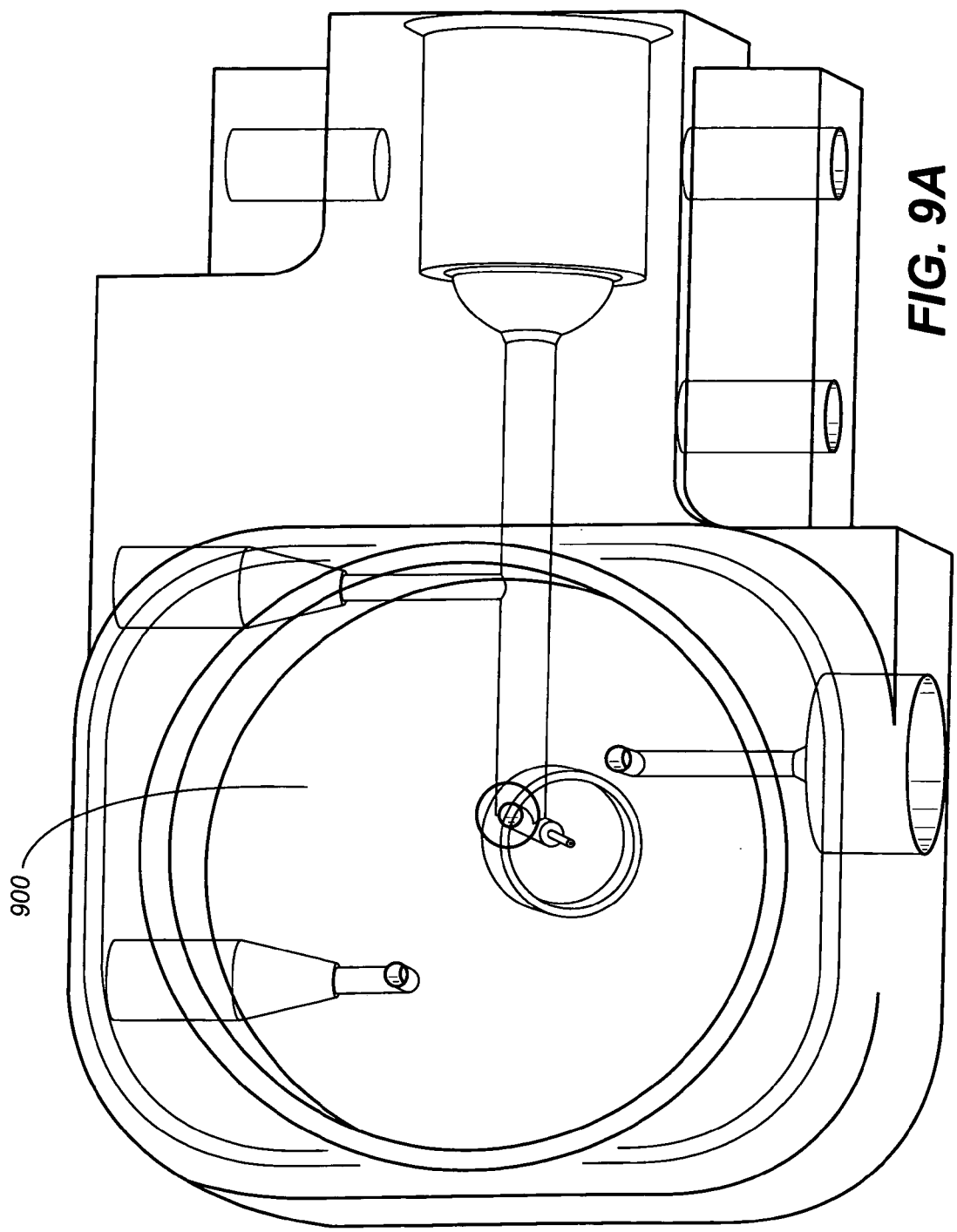
FIGS. 9A-9C depict various reservoir geometries.
Figure 9B:
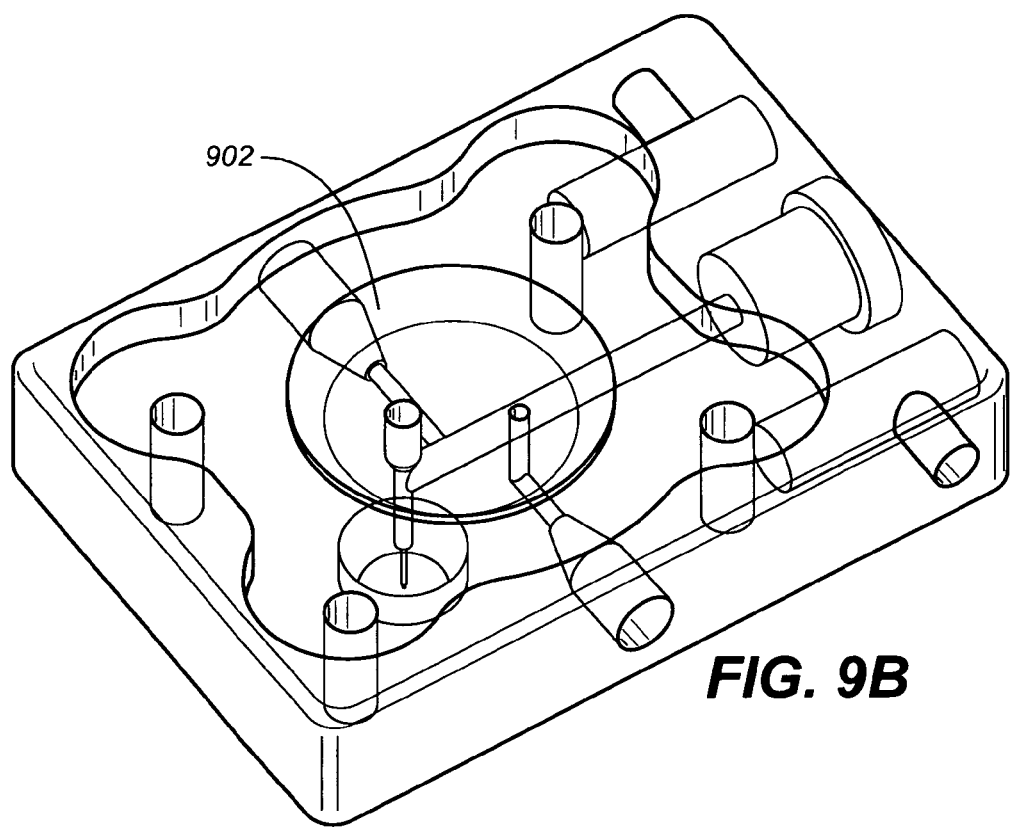
Figure 9C:
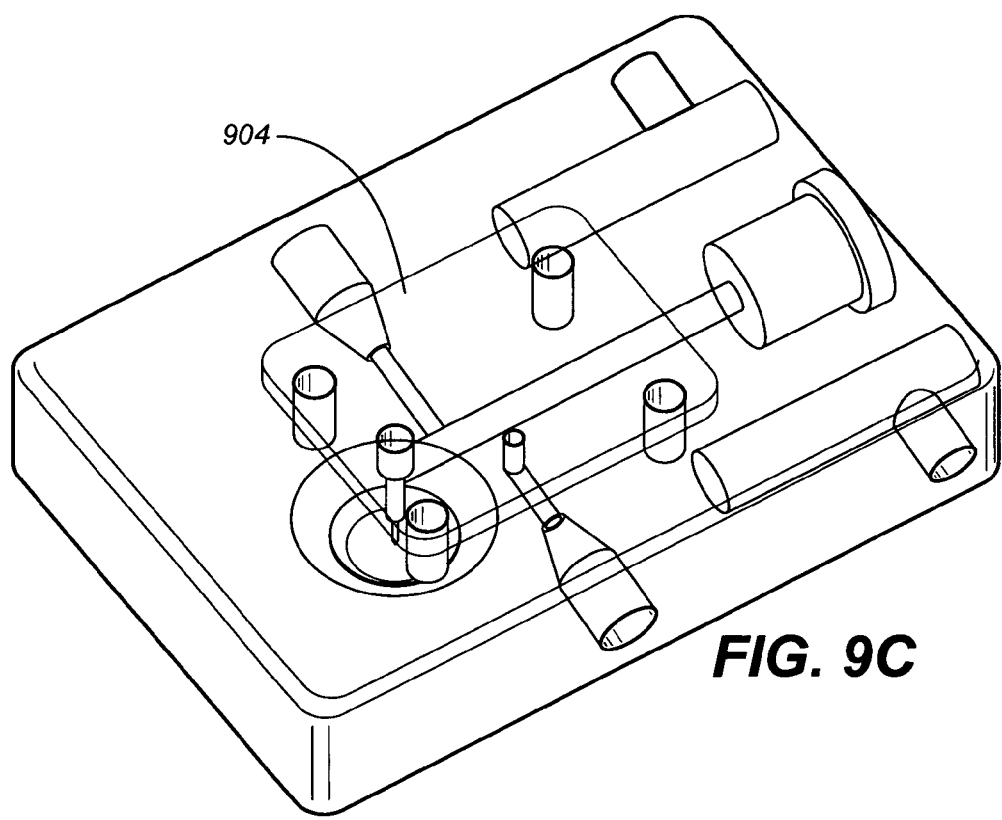

Exemplary reservoir geometries are shown in FIGS. 9A-9C (900, 902, 904). The reservoirs may hold any suitable volume, for example, from about 0.1 mL to about 20 mL. In some variations, the reservoir is configured to hold 1 mL of volume.

Figure 9D:
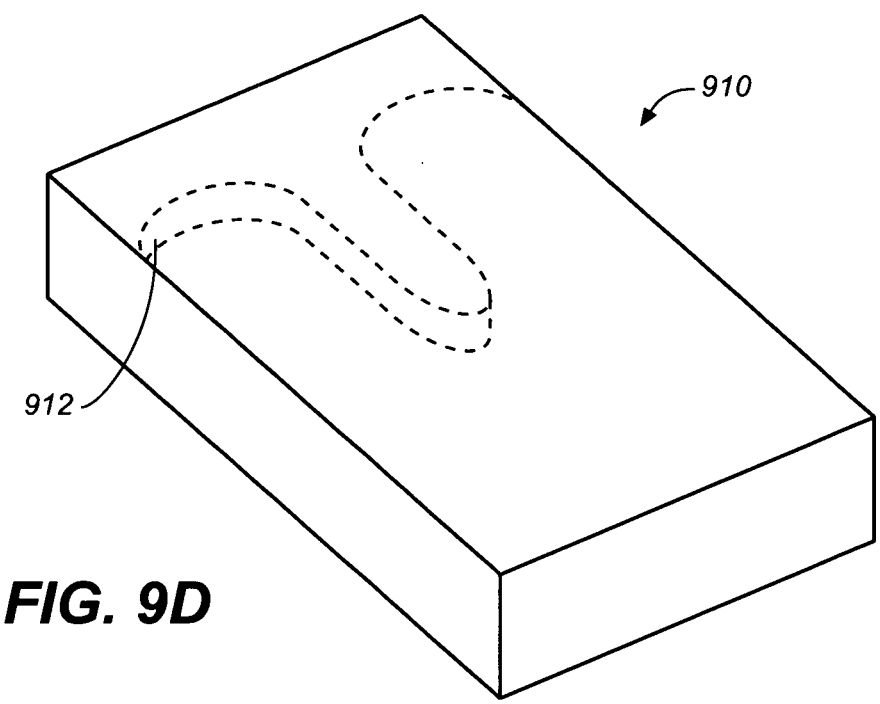
FIGS. 9D and 9E depict reservoirs made from a recess with and without a diaphragm, respectively.
Figure 9E:
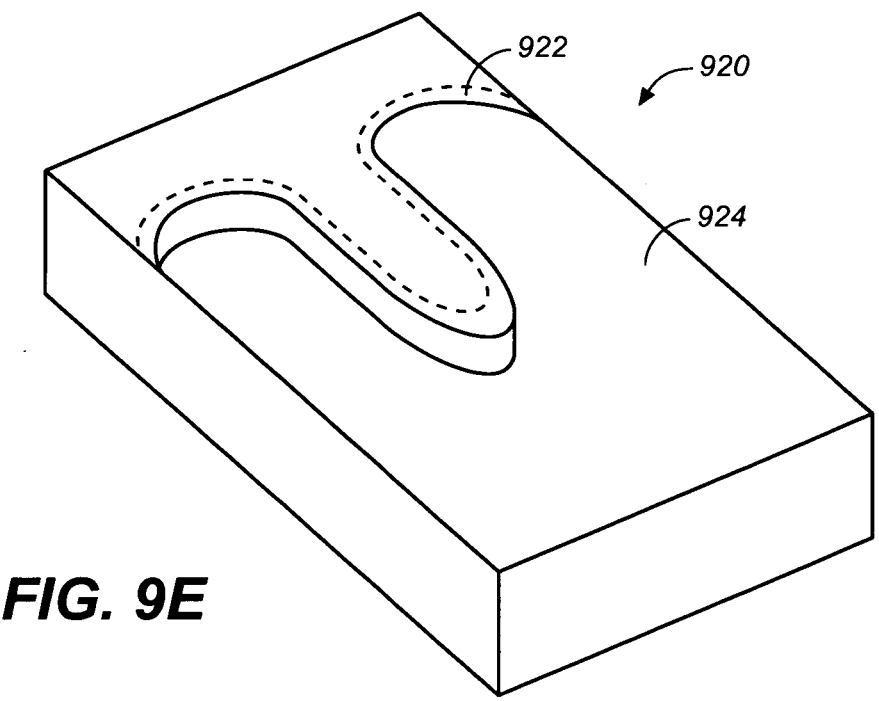

Reservoirs formed by recesses or spaces directly in the device body are also disclosed here. The recess may hold the drug in liquid form directly, or may be used in combination with an embedded porous sheet and/or fibers and/or membrane bladder or pouch. An illustrative reservoir formed by a recess is shown in FIG. 9D and an illustrative reservoir formed by a recess and covered by a diaphragm in shown in FIG. 9E. Shown in FIG. 9D is a device (910) having a recess (912) directly therein for housing a volume of drug in liquid form. Shown in FIG. 9E is device (920) having a recess (922) therein and covered by diaphragm (924). The diaphragm may be attached in any suitable fashion, as described below. In addition, the diaphragm may or may not have one or more vents or ports to help avoid substantial back-pressure in the device.

Figure 10A:
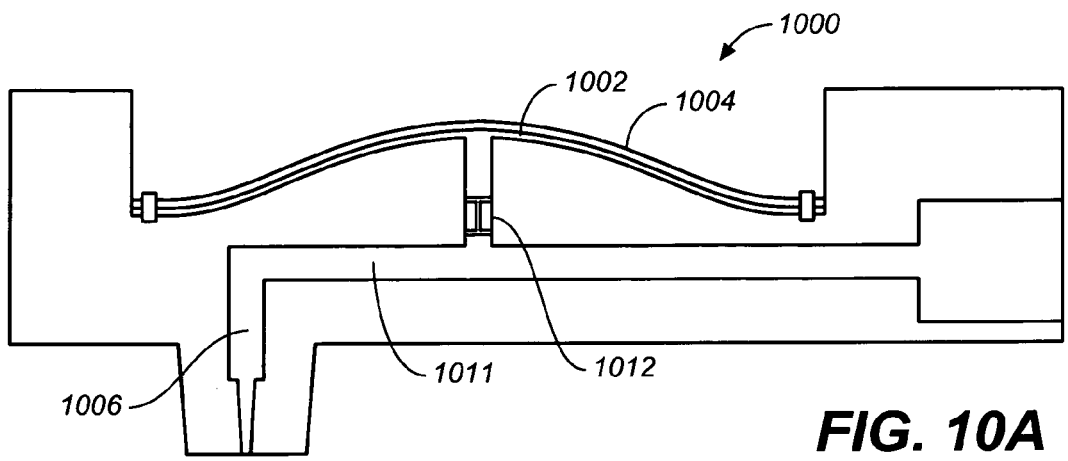
FIGS. 10A and 10B show a diaphragm in its relaxed and pressurized state respectively.
Figure 10B:
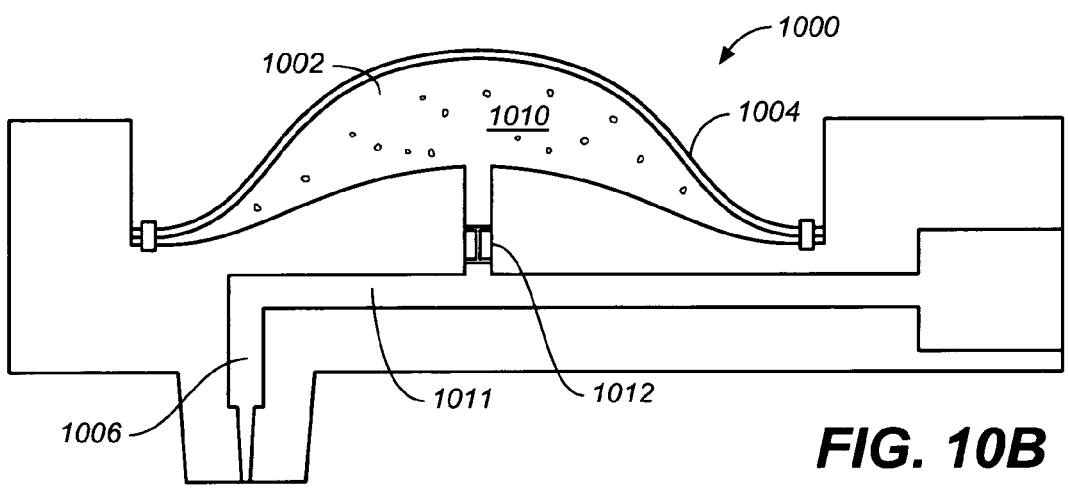
Figure 10C:
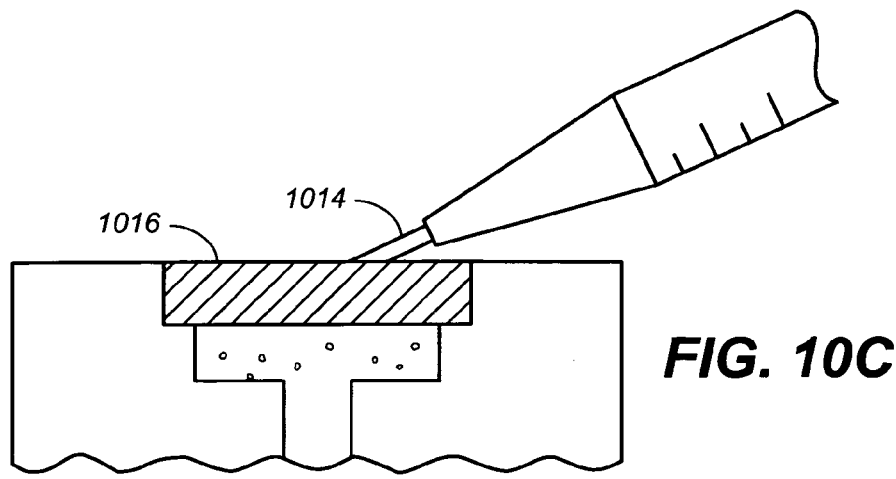
FIG. 10C provides an illustration of how a reservoir may be refilled using a small bore needle that punctures a septum.

Any of the reservoirs described here may be diaphragm-enclosed if desirable, and in some variations, the reservoir is enclosed by a diaphragm, as shown in the illustrative variation depicted by FIGS. 10A and 10B. As shown there device (1000) comprises a reservoir (1002) enclosed by diaphragm (1004). Nozzle (1006) having a 90° angle is also shown. In FIG. 10A, the diaphragm (1004) is in its resting, deflated, or depressurized state. The reservoir may then be filled by puncturing a septum (1016) located on diaphragm (1004) using a small bore needle (1014) or the like (shown in FIG. 10C), which pressurizes the diaphragm (1004) as shown in FIG. 10B. The drug (1010) is then allowed to drain or flow into the main barrel (1011) of device (1000) via a flow restrictor (1012). Suitable flow restrictors will be discussed in more detail below. It should be understood, that while not depicted in FIG. 10C, a septum spacer, may be used. For example, a ring (or portion thereof) of rigid material may be placed around (or at least partially around) the septum to restrict the possible needle depth. In this way, the needle is prevented from rupturing or puncturing one or more reservoir surfaces unintentionally. The septum may be positioned at any desirable location on the device.

The diaphragm should be flexible so that it may expand and/or stretch as necessary to accommodate the reservoir in its drug-filled state. In variations where the diaphragm is refillable and it (or some portion thereof) is puncturable by a small bore needle, it may be desirable that the diaphragm, or the puncturable portion, be made of a quickly self-sealing material, such as a self-sealing silicone or other polymer. Suitable diaphragm materials include any elastomeric material, such as polysiloxane, polyisobutylene, natural or synthetic latex material (e.g., polyisoprene), polyurethanes, and the like. In some variations, polyisoprene is used for the diaphragm.

Figure 11A:
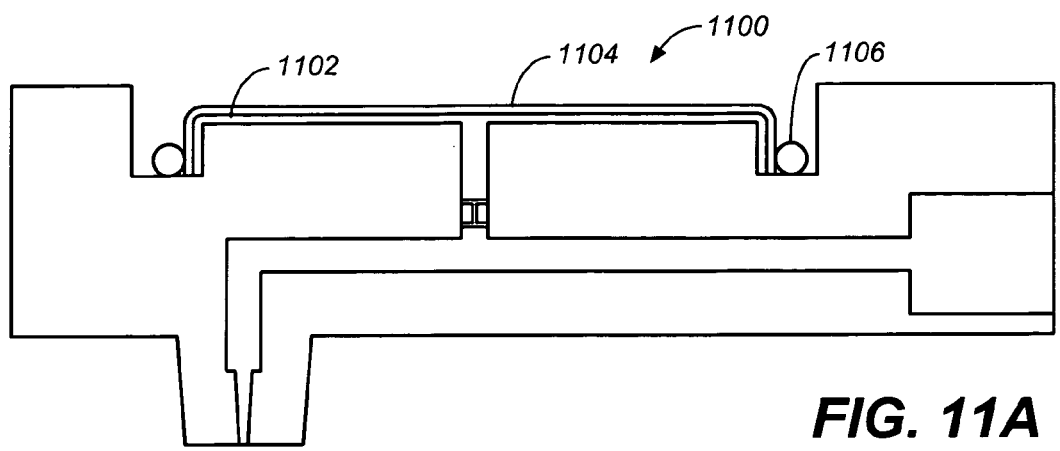
FIGS. 11A-11C depict various diaphragm attachment schemes.
Figure 11B:
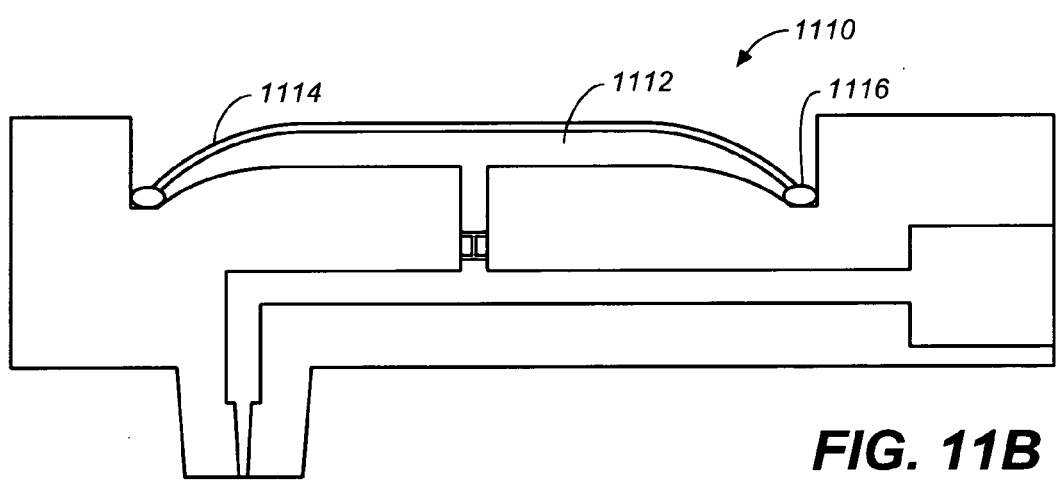
Figure 11C:
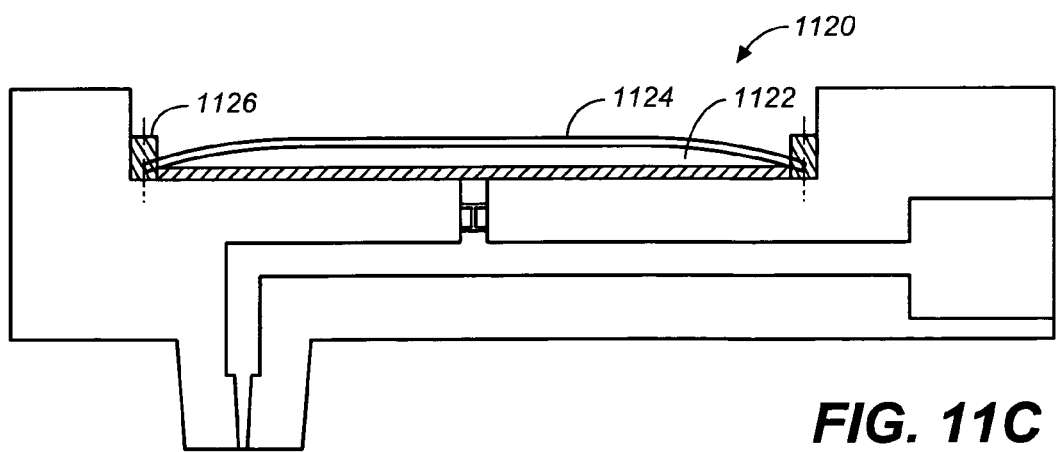

The diaphragm may be attached to the device in any suitable fashion. For example, the diaphragm may be attached by use of an O-ring (FIG. 11A), an adhesive (FIG. 11B), or a retainer (FIG. 11C). More specifically, FIG. 11A shows device (1100) comprising reservoir (1102) enclosed by diaphragm (1104). In this variation, diaphragm (1104) is attached to device (1100) via an O-ring (1106). In a similar fashion, FIG. 11B shows device (1110) comprising reservoir (1112) enclosed by diaphragm (1114) and attached by adhesive (1116). Any suitable adhesive may be used, such as a polysiloxane, polyacrylate, or polyisobutylene adhesive. In some variations, the adhesive is a cyanoacrylate adhesive. FIG. 11C illustrates device (1120) comprising reservoir (1122) enclosed by diaphragm (1124) attached to device by a retainer frame (1126). The retainer frame (1126) may be anchored to the diaphragm with fasteners (screws, etc.), an adhesive, or the like. In variations where a retainer frame is used to couple the diaphragm to the device, it may be desirable for the retainer to apply uniform pressure on all sides to help ensure that the diaphragm withstands the fluid pressure without any leak. The diaphragm may be stretched prior to loading of the reservoir, or may be kept in its natural unstretched state.

Figure 12A:
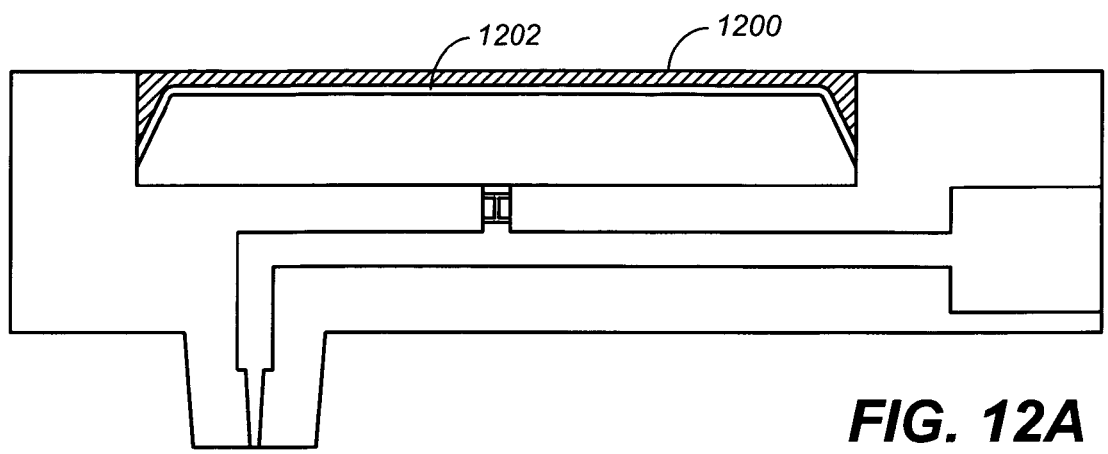
FIGS. 12A and 12B show variations where a cap is used to block entry to the reservoir.
Figure 12B:
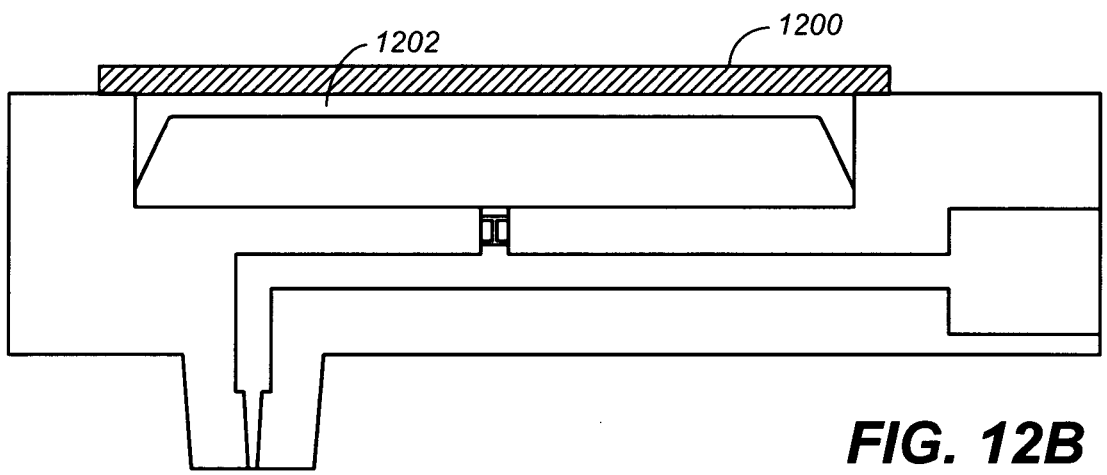

The volume of drug to be loaded into the reservoir is largely dependent on the drug to be delivered and the dosing regime or therapy to be followed. However, in some embodiments, the drug volume is restricted by the use of a reservoir enclosure cap as shown in FIGS. 12A and 12B. In this way, external access to the reservoir is blocked, and diaphragm puncture and tampering of the device (e.g., in potential abuse situations) is prevented. The enclosure cap (1200) may conform to at least a portion of the diaphragm (1202) as shown in FIG. 12A, or may cover the entire diaphragm (1202) and be attached directly to one or more device surfaces as shown in FIG. 12B.

Figure 13A:
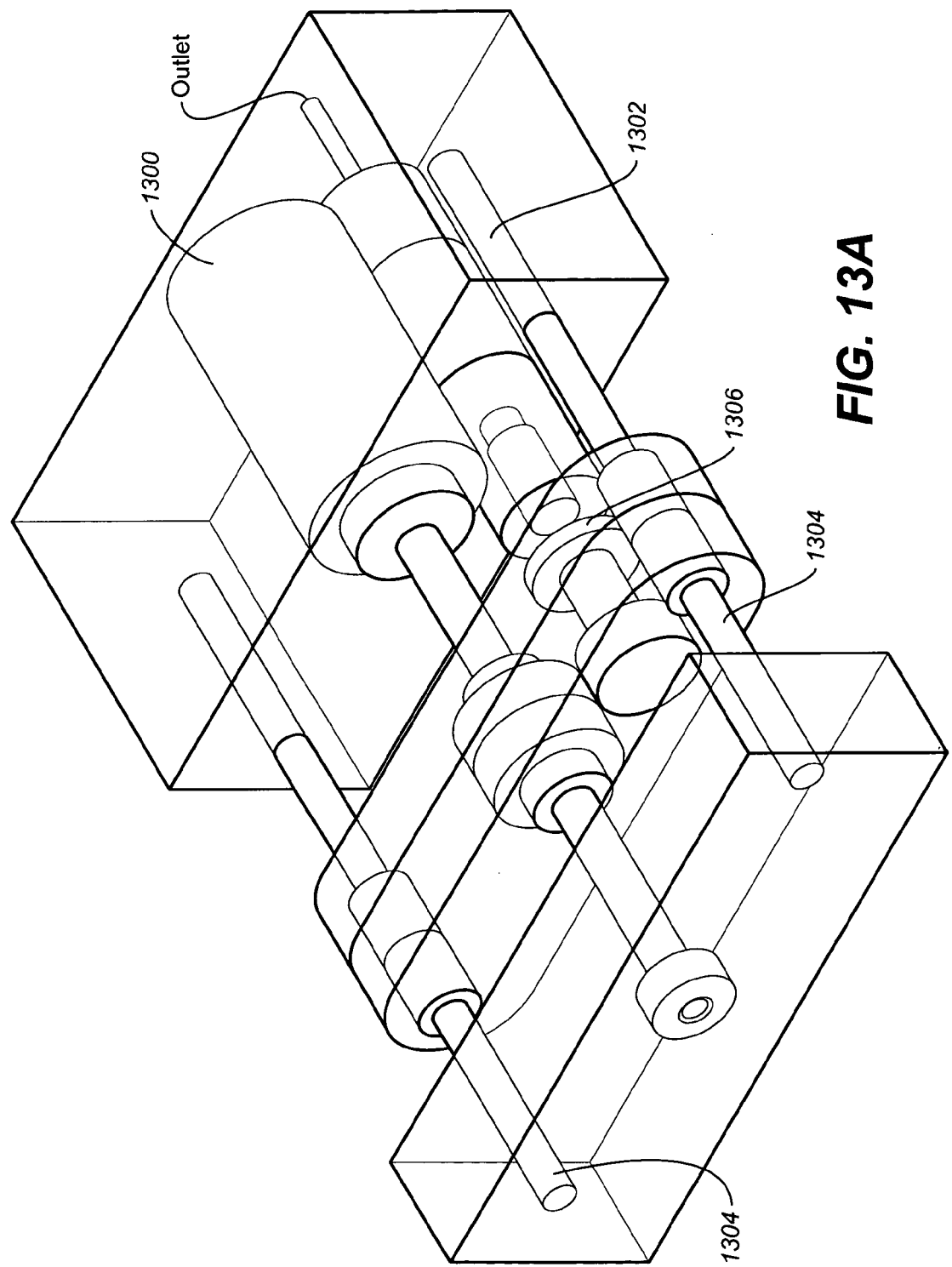
FIGS. 13A and 13B provide illustrative depictions of microstepper motor driven reservoir designs.

Typically, some type of force is required to fill (or refill, if drug has been ejected therefrom) the barrel or nozzle of the device with drug from the reservoir. This force may be any suitable force, e.g., mechanical, electrical, compressed gas, etc. FIGS. 13A and B provide illustrative variations where a microstepper motor is used to refill the nozzle or barrel of the device from the reservoir. Using a microstepper motor may be particularly useful in instances where programming the refill rate is desirable or necessary.

Figure 13B:
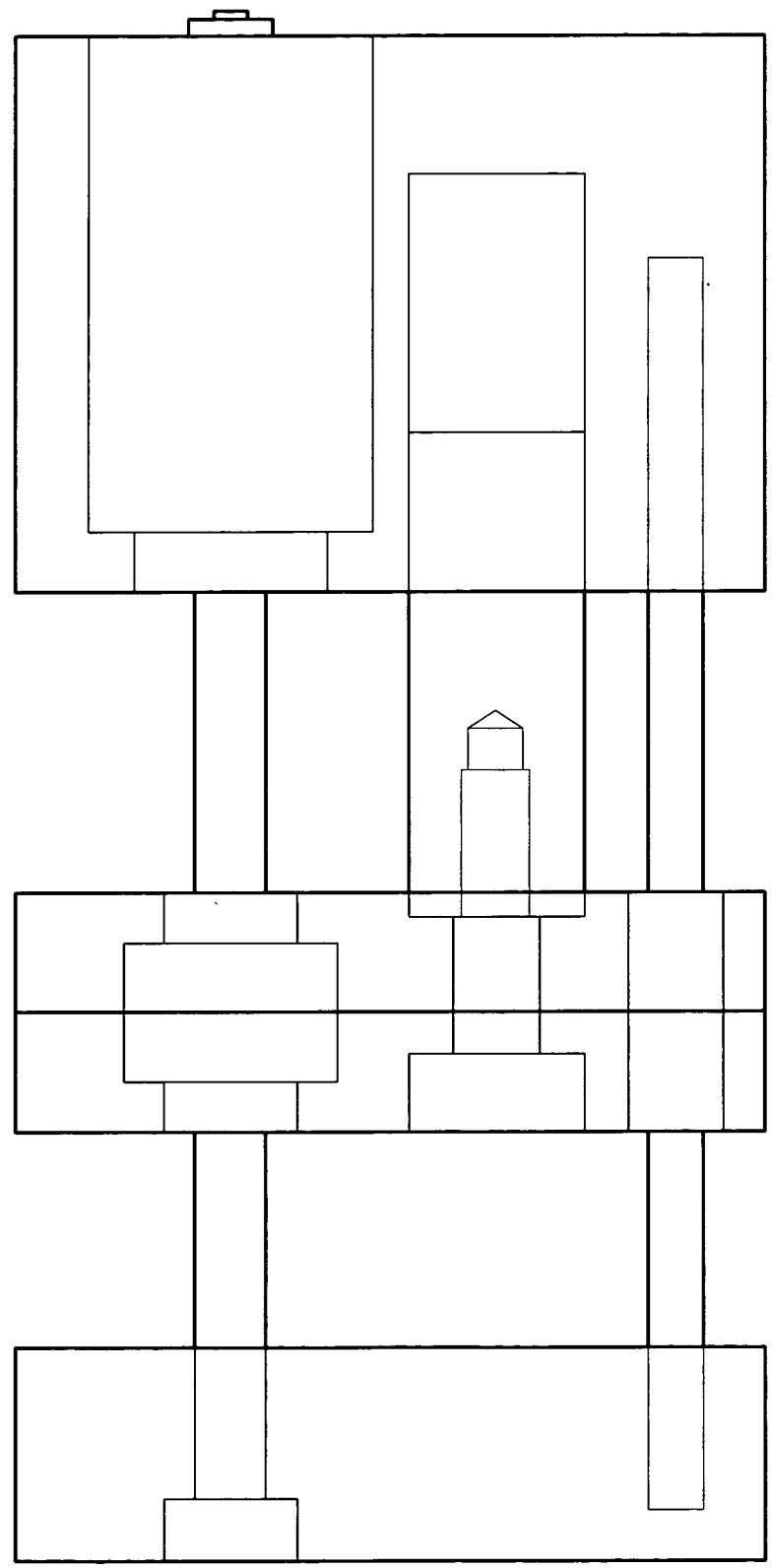

In this variation, the motor (1300) is attached to reservoir (1302), here shown as a recessed cylindrical cavity. The stepper motor (1300) in this variation is mounted using guide pins (1304), which in this variation, are stationary and support the bracket holding the motor. Also shown is piston (1306). The piston (1306) is connected to the bracket so that when the motor screw translates, the piston (1306) is moved. The moving piston (1306) then pushes drug from the reservoir into the barrel or nozzle as the case may be. The piston of this variation may include one or more seals. For example, a seal around the piston face may be accomplished by a bushing, a diaphragm, an O-ring or the like. The microstepper motor (1300) may use multiple guide pins (1304) as shown in FIG. 13A, or may use only one guide pin, as shown in FIG. 13B. Variations utilizing a microstepper motor may or may not further comprise a flow restrictor as will be discussed in more detail below. Suitable microstepper motors are well known in the art and any such motor may be used here. In addition, other motors capable of driving the reservoir, not shown in the figures, may be used. Such motors include motors from smoovy miniature drive systems, flat DC gearmotors, smoovy brushless DC drives, ARSAPE miniature drive 1-phase and 2-phase stepper motors, penny motors and penny brushless gearmotors, brushless DC servometers, coreless DC micromotors, ultraflat DC micromotors and gearmotors (all from Micromo Electronics, Faulhaber Group); miniature ultrasonic piezoelectric motors such as squiggle motors (from New Scale Technologies); ARSAPE single phase stepper motors in 6, 8, 10, 15, and 22 mm range; and series AM2224 and series ADM 0620 (from Donovan Micro-Teck Inc.); and the like.

Figure 14:
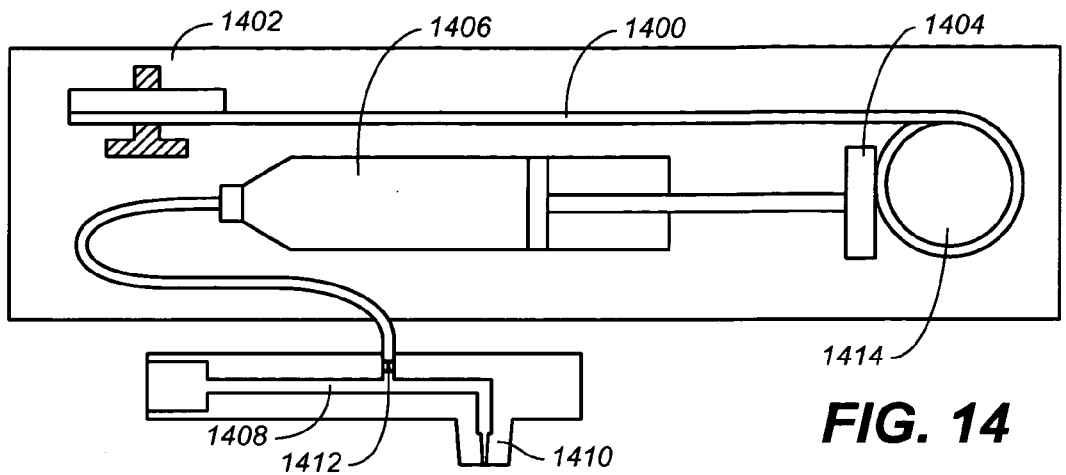
FIG. 14 provides an illustration of a constant spring force driven reservoir design.

In some variations, a constant spring force is used do refill the barrel or nozzle from the reservoir. This variation may be particularly useful in cases where a constant flow rate is desired. FIG. 14 provides an illustrative example of this variation. Shown there is a pre-stressed coiled spring (1400), which gets extended as it uncoils. The loose end of the spring is anchored (1402) and the spring is allowed to release its energy while it uncoils. As it uncoils, the spring extends and pushes the piston (1404) of reservoir (1406), thus pushing out drug volume. In this variation, the reservoir is connected to the barrel (1408) and nozzle (1410), and a flow restrictor (1412) is used. Any number of springs may be used, and while spring (1400) is shown here as mounted on a spindle (1414), the spring may be mounted in any suitable fashion.

Figure 15:
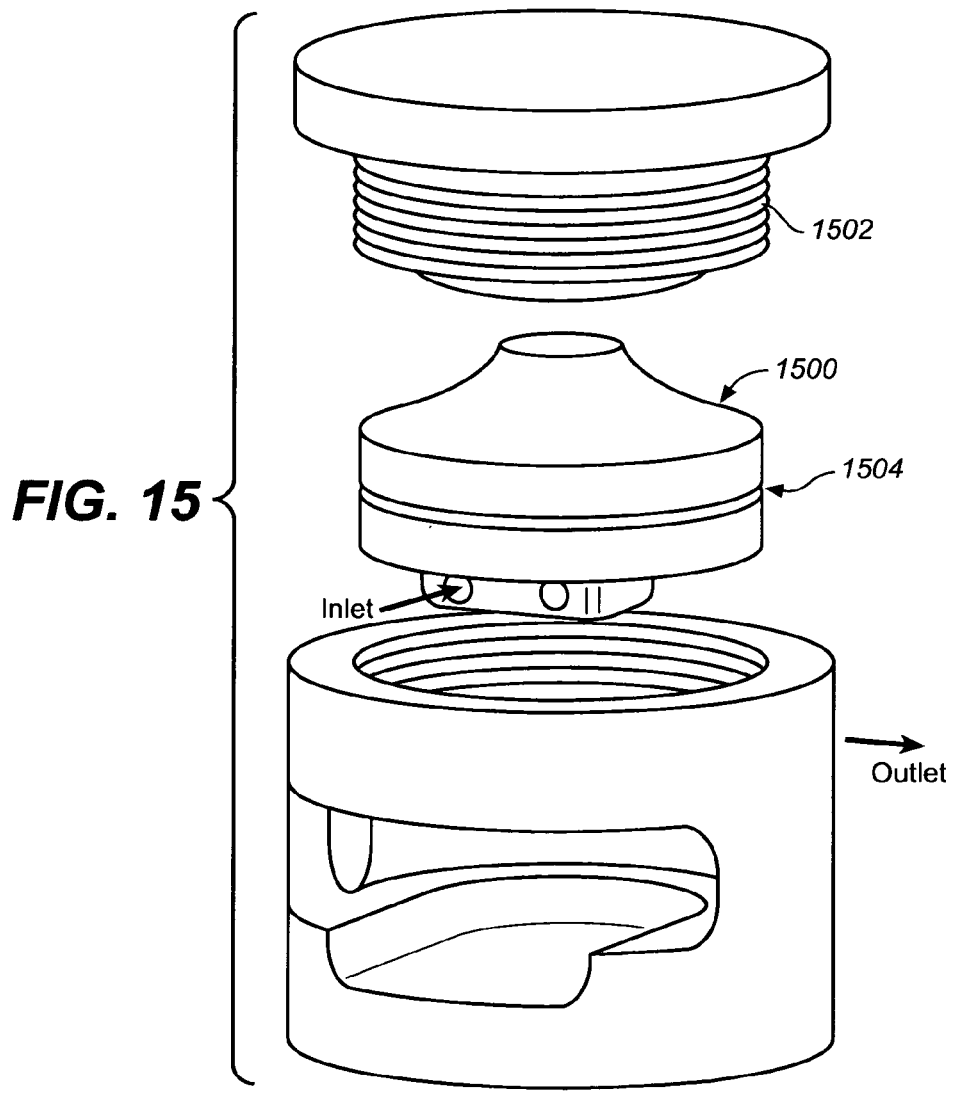
FIG. 15 provides an illustration of a Belleville spring driven reservoir design.

Other springs may also be used for refill purposes. For example, in some variations, a Belleville spring is used. A Belleville spring is generally flat and has a low profile. The force displacement (or load-deflection) curve of the Belleville spring typically has a generally flat region where force is relatively constant, and in some of the variations, the Belleville spring is operated in that region. An illustrative example of how a Belleville spring may be used with the devices described here is provided by FIG. 15. Shown in FIG. 15 is Belleville spring (1500), which is compressed by a spring compressor (1502) to act on reservoir (1504). It should be noted that while a spring compressor (1502) is depicted here, any suitable driving force may be used. In some variations, using a Belleville spring helps to completely drain the reservoir.

Figure 16:
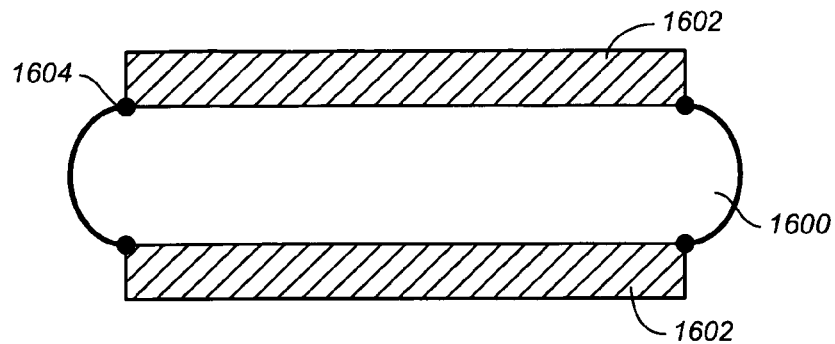
FIG. 16 shows a variation of a flexible and collapsible reservoir that may be used with the devices described herein.

When a Belleville spring is used, it may be further desirable to have a flexible reservoir, as depicted in FIG. 16. Shown there is a reservoir (1600) enclosed between two flat plates (1602). The reservoir may be bound to the flat plates (1602) in any suitable fashion, and in some variations, an adhesive (1604) is used. The reservoir of this variation is made from a flexible material, such as an elastomer, so that it is collapsible. This variation may be particularly useful to help ensure that as the reservoir is depleted of drug volume, the empty space is not replaced with air. While a reservoir of this type has been described in connection with the Belleville spring variation, it should be understood that such the flexible and collapsible reservoir just described may be used with any of the devices described here.

Figure 17A:
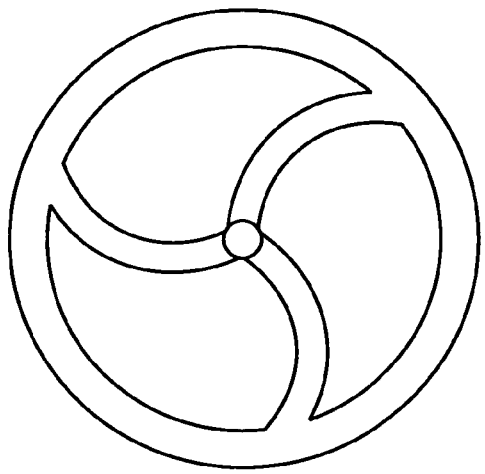
FIG. 17A-18C depict various spring designs that may be used with any of the devices described here.
Figure 17B:
Figure 18A:
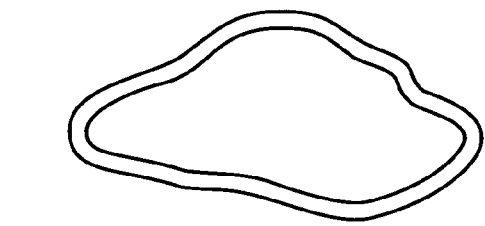
Figure 18B:
Figure 18C:
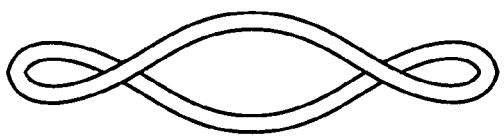

Other springs may also be used for refilling the barrel or nozzle with drug from the reservoir. For example, a flexural spring (flat spring or wave spring) may be used. This spring typically has a low profile, which may be advantageous in instances where it is desirable to reduce the overall profile of the device. Top and side views of an illustrative flexural spring (1700) are shown in FIGS. 17A and 17B respectively. Other suitable springs are shown in FIGS. 18A-C. It should be understood that any number of springs may be used, and in some variations, multiple springs are used in a stacked configuration.

Figure 19:
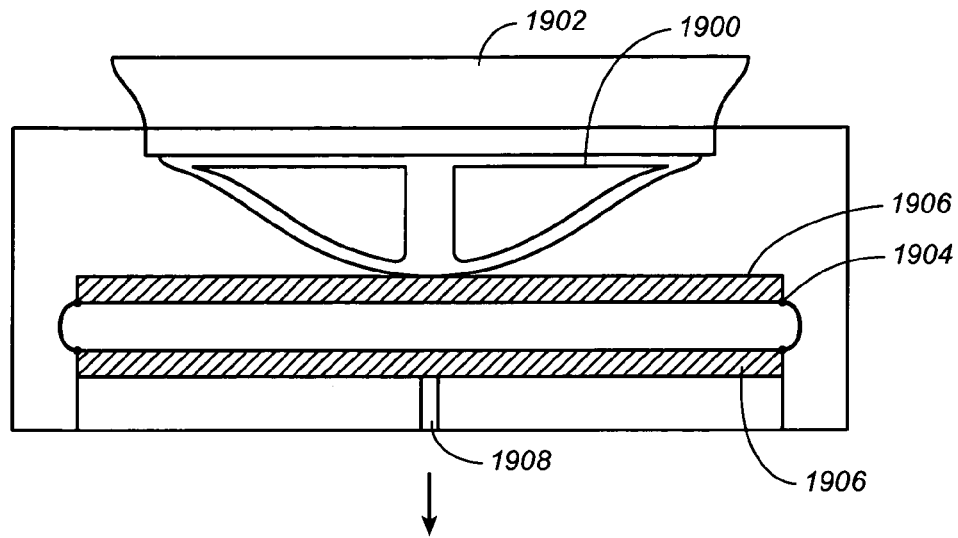
FIGS. 19 and 20 show illustrative variations of how a spring may be used with the reservoirs described here.
Figure 20:
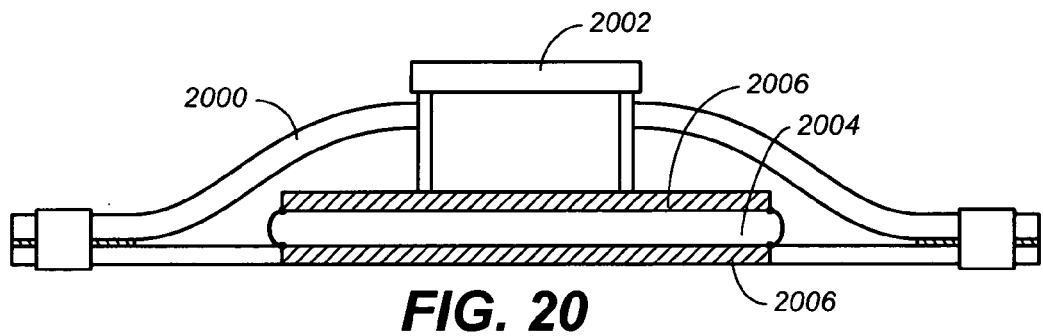

One variation showing how a low profile flexure spring may be used is shown in FIG. 19. There, spring (1900) rests against a flat surface and is compressed by spring compressor (1902). The reservoir (1904) is flexible and of the nature described above, held between plates (1906). Once spring (1900) acts on reservoir (1904), drug is moved through restrictor (1908), which in turn feeds the nozzle (as shown by the arrow) via any of the configurations previously described. Another variation is shown in FIG. 20. In the variation of FIG. 20, spring (2000) engulfs reservoir (2004), and is integral or otherwise directly connected with spring compressor (2002). Other springs, e.g., elastomer diaphragms, which act as springs such as the variations depicted in FIGS. 11A-C, may be used as well. Again, the nozzle may be connected via any of the configurations previously described.

Figure 21:
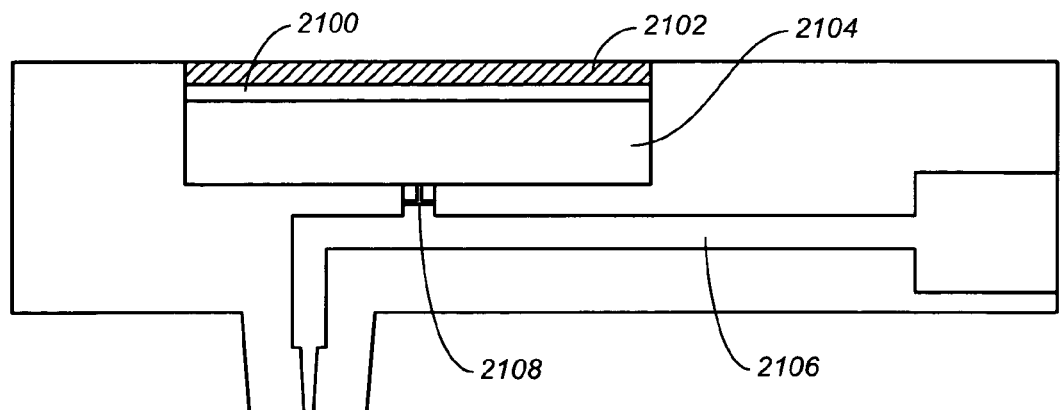
FIG. 21 shows an illustrative variation utilizing a piezoelectric disc to act on a reservoir.

In some variations, a piezoelectric mechanism, e.g., a piezoelectric disc or the like is used for refill purposes. In these variations, a reservoir diaphragm is typically used, and the diaphragm acts as a barrier between the piezoelectric mechanism and the reservoir containing drug. The diaphragm in this variation may also act as a sealant to help prevent drug leakage and the reservoir may be filled via the use of one or more septa, in the manner described above. FIG. 21 shows an illustrative variation utilizing a piezoelectric disc. In this variation, the diaphragm (2100) separates piezoelectric disc (2102) from reservoir (2104). The piezoelectric disc (2102) will expand under the action of externally applied voltage (as will be described in more detail below) and will apply pressure on the drug through the diaphragm. In instances where the piezo displacements are small, the pressures generated should be sufficient to drive fluid into barrel (2106) without the use of a flow restrictor. However, flow restrictor (2108) is also depicted, and may be used in these variations. Indeed, in instances of large displacements or large drug volumes, a flow restrictor may be suitable or desirable.

One or more pumping devices may also be used to refill the nozzle, e.g., a peristaltic or infusion pump, which may or may not have a separate flow restrictor in its path. In some variations, a microperistaltic pump is used. The peristaltic action of the pump may be programmable. In other variations, hydrogels are used for pumping action. For example, expansion and contraction of hydrogels in response to various external stimuli (e.g., pH, temperature, solvent concentration, radiation, etc.) may be used to create motion for refilling the nozzle, with or without a plunger.

C. Flow Restrictors

As just described above, after the nozzle has ejected a volume of drug (e.g., using any number of the dispensing members described herein, which will be discussed in more detail below), it must be refilled so that it can dispense one or more additional volumes of drug. In general, the refill rate to the nozzle is governed by the dynamic and geometric properties of the refill conduit, and in some variations, it is useful to employ a flow restrictor.

For example, a simple flow restrictor, such as a high resistance fluidic channel, or a tubing packaged into a channel (e.g., a small diameter channel having an ID ranging from about 10 µm to about 200 µm) may govern the flow rate. The flow restrictor may have any suitable geometry, shape, orientation, and length. It may be straight, coiled, some combination of both, or the like. Similarly, the flow restrictor may be placed in any functional location, so long as it can effectively control the refill rate to the nozzle. For example, it may be placed directly in between the reservoir and the nozzle, be embedded on one or more reservoir surfaces, or be in a separate module that may be plugged directly into the device.

Figure 22:
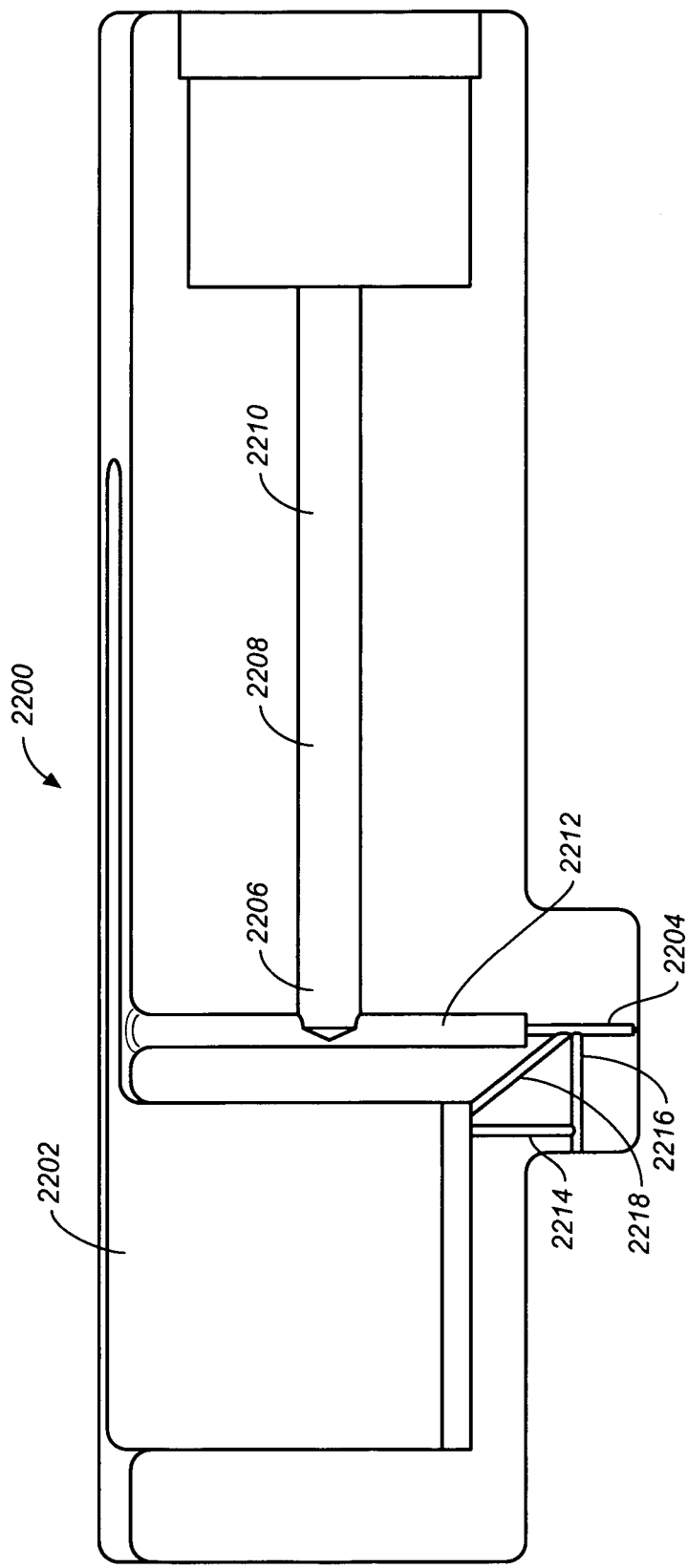
FIG. 22 shows a recessed reservoir and depicts several suitable locations for flow restriction.

FIG. 22 shows a device (2200) having a recessed reservoir (2202) and nozzle (2204) in fluid communication therewith. In this figure, generalized locations for nozzle refill from the reservoir after a dose of drug has been ejected therefrom are shown. For example, the nozzle may be refilled from any of the locations (2206, 2208, 2210, 2212, 2214, or 2216). In the variation shown in FIG. 22, a flow restrictor (2218) is provided, although the flow restrictor may be at any of locations 2206, 2208, 2210, 2212, 2214, and 2216 previously disclosed.

Capillary action or wicking may also be used to refill the nozzle with drug from the reservoir and/or for flow restrictor purposes. For example, a wicking rod or the like may be used. In this variation, the rod may supply drug directly into the nozzle or barrel of the device from the reservoir. The function of the wicking rod may be further enhanced by the use of a collection bowl. Any number of wicking rods may be used, and the wicking rods may have any suitable geometry. Similarly, any number of collection bowls may be used, and the bowls may be placed in any desirable location.

Figure 23A:
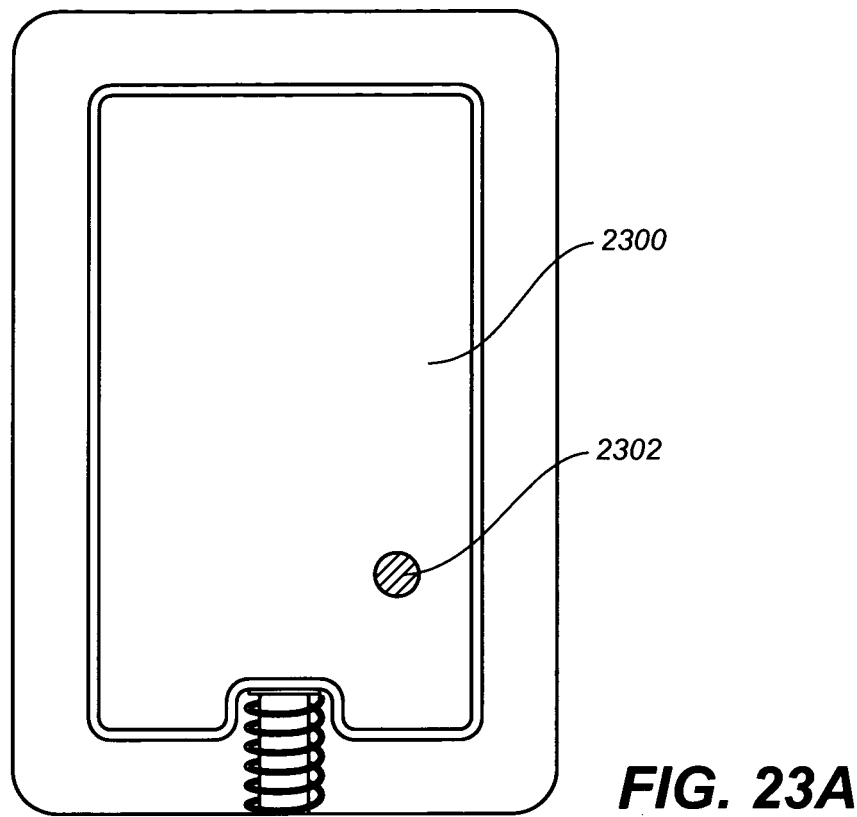
FIGS. 23A-23C depict various wicking regimes for flow restriction.
Figure 23B:
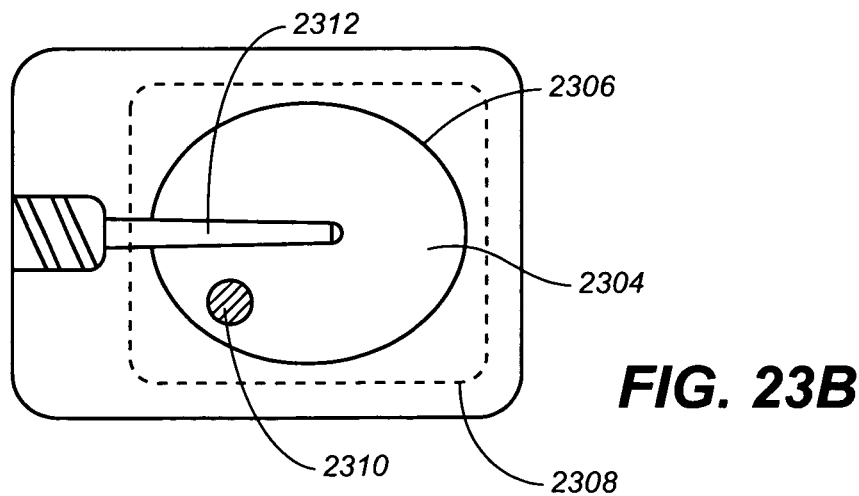
Figure 23C:
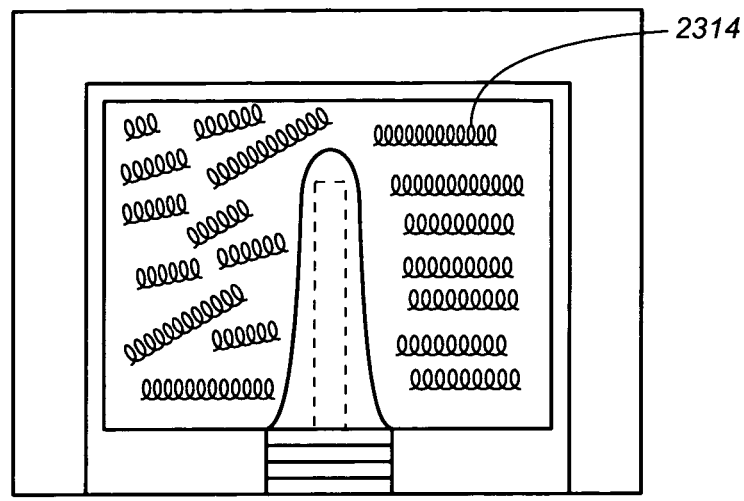

In some variations, the reservoirs described here may also have a wicking surface, a wicking material, or be constructed to include one or more wicking matrixes or the like. For example, FIG. 23A illustrates one variation of a reservoir covered from the top to its bottom surface with a wicking material (2300). Septum (2302) used for filling or refilling the reservoir with drug, e.g., made of a self-sealing silicone material, is also shown. FIG. 23B shows one variation of a reservoir comprising both a wicking material (2304) and a diaphragm (2306), such as those diaphragms described just above. In this variation, the device also comprises a retention frame (2308) for the diaphragm. Fill septum (2310), and barrel (2312) are also shown. FIG. 23C shows a variation where the reservoir is filled with an open-cell wicking foam (e.g., a porous hydrophilic polymeric material). One or may layers of an open-cell foam may be used.

Figure 24:
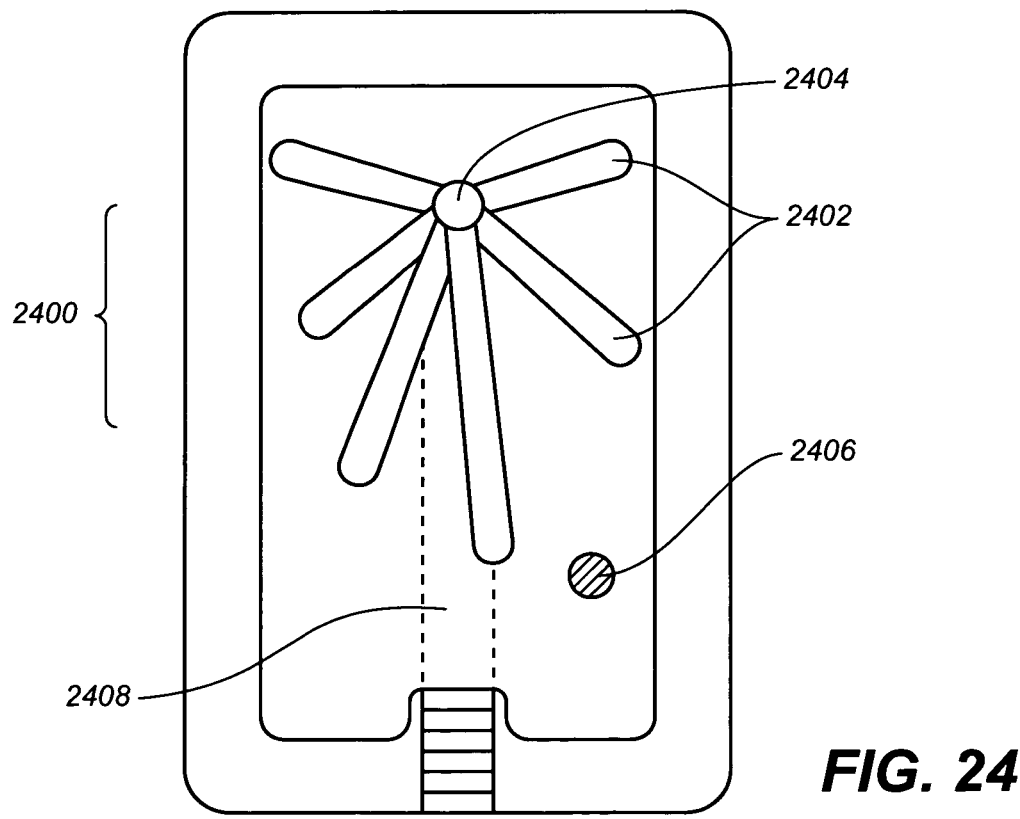
FIG. 24 depicts a microfluidic channel used for flow restriction.
Figure 25A:
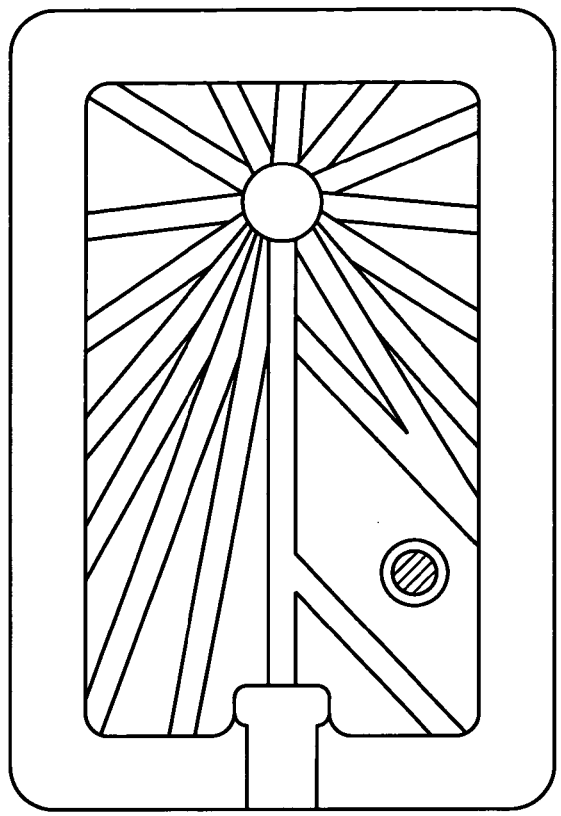
FIGS. 25A and 25B provide top and bottom views respectively of a microfluidic or wicking pattern that may be etched or otherwise patterned onto the top and bottom surfaces of a reservoir.
Figure 25B:
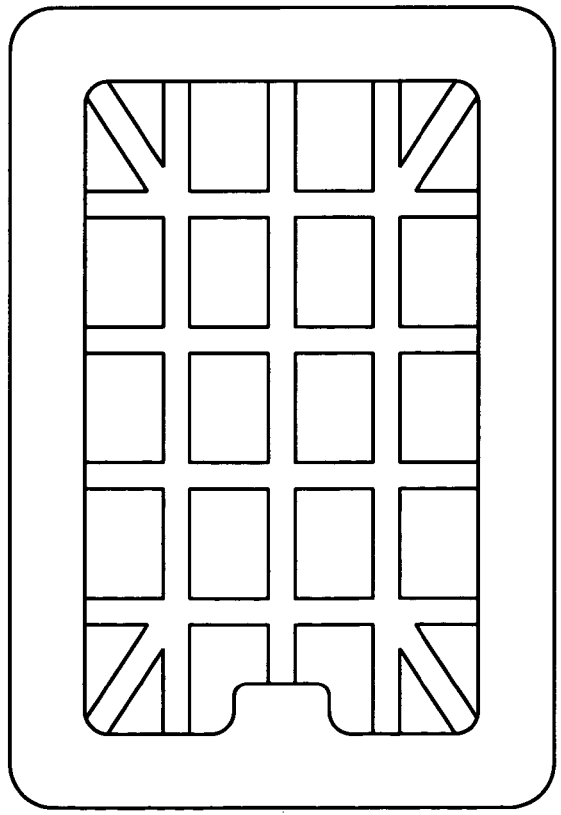

FIG. 24 provides an illustration of a wicking microfluidic circuit in conjunction with the devices described here. This variation may be particularly useful in instances where a collapsible reservoir is not used. In these variations, the microfluidic circuit may help provide access to the drug (because for example, at least a portion of the circuit would be in fluid communication with the drug), independent of the reservoir location and/or orientation. The circuit (2400) has arms (2402) that radiate outward from a collection bowl (2404). Septum (2406) for refilling, and barrel (2408) are also shown. FIGS. 25A and 25B provide top and bottom reservoir views respectively of a microfluidic or wicking pattern that may be etched or otherwise patterned onto the top and bottom surfaces of the reservoir. Procedures for such patterning are well known in the art and include techniques such as surface machining, laser cutting, lithography, injection or impression molding, and the like.

D. Dispensing Members and Actuators

In general, the devices described here comprise some type of dispensing member for dispensing drug out of the nozzle opening, and often the dispensing member is actuated by the use of some type of actuator or actuating member. The dispensing member may be any suitable dispensing member, for example, a spring, disc, or any other component capable of acting on a liquid. In some variations, the dispensing member and the actuator are the same. In other variations, the dispensing member is a plunger (rod, piston, push-pull member, etc.). The plunger may be made of any suitable material (e.g., coated or non-coated metal, plastic, or the like) and may have any suitable geometry. Illustrative plunger tips are shown in FIGS. 26A-D. As illustrated there, the plunger tip may be rounded, conical, flat, or flat with rounded edges as shown in FIGS. 26A, B, C, and D respectively.

The plunger head may also have any suitable geometry and may have one or more extension or cross pieces thereon, and such extension or cross piece may or may not have a recess for receiving, accommodating, coupling with, or otherwise engaging an actuator, or a portion thereof. For example, FIG. 27A provides an illustrative depiction of a plunger having an extension or cross piece with a flat head (2700). FIG. 27B provides a depiction of a plunger having an extension piece with a rounded head (2702), and FIG. 27C provides a depiction of a plunger having an extension piece with a recess therein (2704) for receiving, accommodating, engaging, or otherwise coupling with, an actuator. FIG. 27D provides an illustration of an extension piece (2706) connected to plunger body (2708) in a hinged, ball and socket joint fashion (2710). In some variations, a plunger having a circular cross-section is used. At least a portion of the plunger or other dispensing member may be hollow, or have a port or lumen therethrough to provide for refill access. Such a plunger is shown in FIG. 28. Shown there is plunger (2800) having refill port (2802).

One or more springs are typically used for dispensing member recoil and any suitable spring may be used (such as precision compression springs, Belleville springs, die springs, disc springs, helical springs, etc.). For example, FIG. 29A illustrates plunger (2900) having spring (2902). Also shown is sealing member (2904). Sealing members will be discussed in more detail below. The spring may be positioned in any operable location. For example, the spring may be attached to the plunger body, may be free hanging, may be attached to the device body itself (not shown), may be attached to sealing member (2904), or the like. Various spring profiles are depicted in FIGS. 29B-D. It should be understood that multiple springs may be used (especially in the case of Belleville, disc, or other generally flat springs), and they may be used in a stacked, parallel, or anti-parallel fashion.

Figure 30:
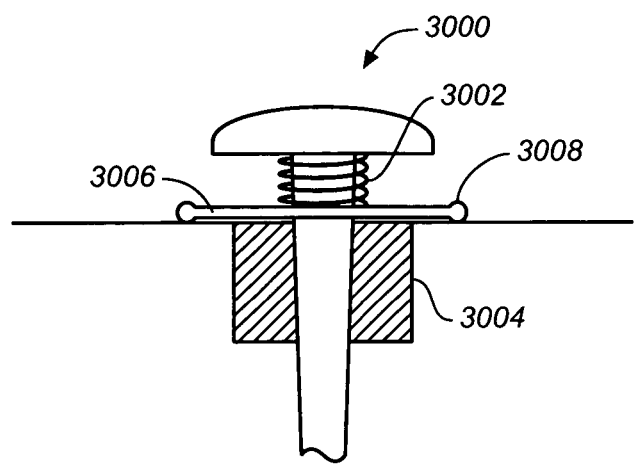

Due to potential leak paths from the plunger-spring interface, it may be desirable to include one or more sealing members, or elements to reduce or prevent leakage. For example, shown in FIG. 30 is plunger (3000) having spring (3002). Seal or plug (3004) is shown, as is O-ring (3006), which is held in place by adhesive (3008), both seal (3004) and O-ring (3006), will help prevent leakage. Seal (3004) may be any suitable seal. For example, it may be a flexible silicone, such as polydimethylsiloxane (PDMS), or the like. In some variations, a flexible silicone is used as seal (3004), and it is made or formed in-situ by first filling the seal space with a liquid silicone material and then curing it. In this way, the seal will conform to the plunger geometry, which can be extremely advantageous in helping to prevent leakage. It should also be noted that in some variations, it may be desirable to have the plunger bonded to the device body or diaphragm.

Figure 31:
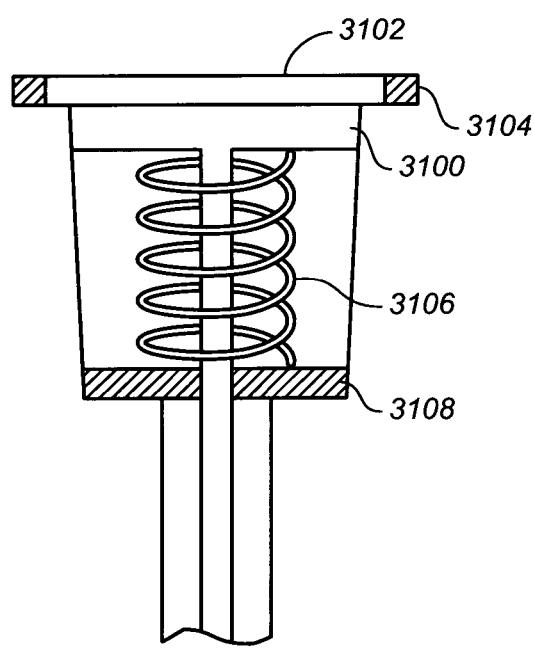

FIG. 31 shows another device configuration where the plunger head (3100) is inside device body enclosed by a diaphragm (3102) held by adhesive (3104), although other attachment mechanisms are also suitable such as, retainer rings, mechanical fasteners and the like. In this variation, seal (3108) is also shown to help prevent leakage about spring (3106).

FIGS. 32A and B show additional variations to reduce leakage. Shown in FIG. 32A is plunger (3200) having plunger head (3202). In this variation, a metal bellow (3204) is used instead of a spring. Here, the bellow is attached to the plunger head (3202) and device body around its periphery, forming a hermetically sealed enclosure. The bellow may be made out of any suitable metal. In the variation shown in FIG. 32B, an elastomeric tube (3212) is used. In this variation, the tubing surround spring (3210) and plunger (3206) and is attached to the plunger head (3208) and device body forming a hermetically sealed enclosure. Also shown in the variation of FIG. 32B is seal (3214), such as those seals described above.

Sealing may also be improved with the use of one or more grooves on the dispensing member with or without the use of in-situ seal formation. Various such grooves are depicted in FIGS. 33A-33C. Shown in FIG. 33A is plunger (3300) and spring (3302). Plunger (3300) has a series of grooves (3304) thereon, and a seal (3306) has been formed corresponding to the grooves (3304). The seal (3306) may or may not be formed in-situ. In instances where the seal is formed in-situ (for example, using the methods described above), the seal formed between the dispensing member and the seal (3306) will be of a ring type or flange type nature. The dispensing member may have any number of grooves thereon, and the grooves themselves may have any suitable geometry. They can be annular with or without rounded corners, or the like.

FIGS. 33B and 33C provide close up views of dispensing members (3308) and (3310) having various geometries. Similarly, any appropriate spacing may be used between the grooves.

Figure 34A:
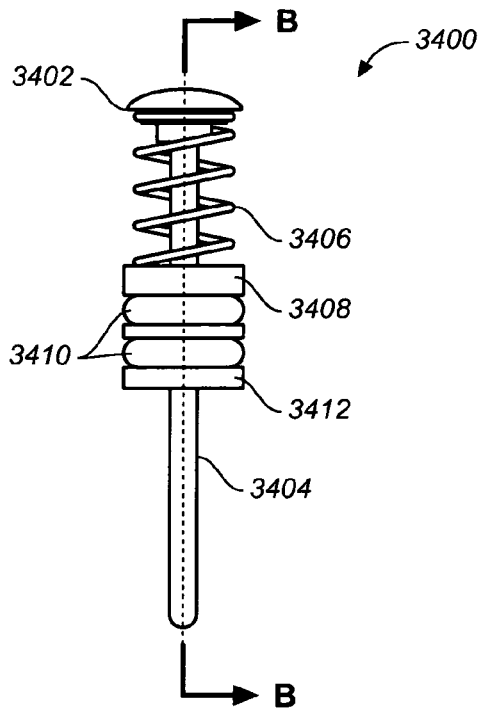
FIG. 34A provides an illustrative depiction of a suitable dispensing member as described herein, and FIG. 34B provides a cross-sectional view of the dispensing member of FIG. 34A taken along line B-B.
Figure 34B:
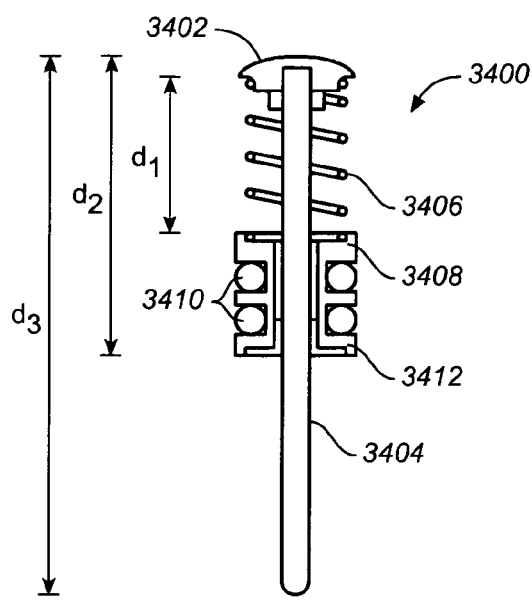
Figure 35:
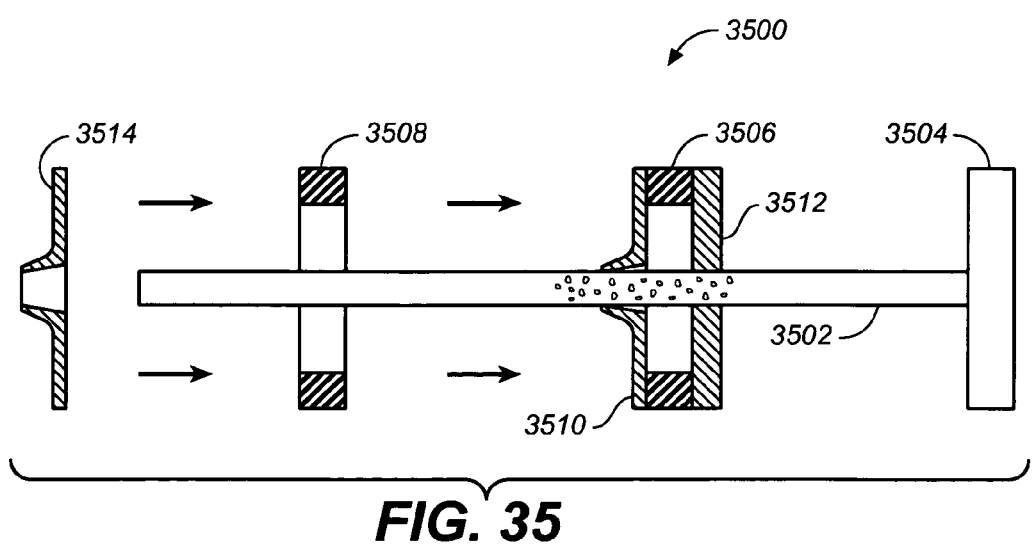
FIG. 35 depicts how a dispensing member assembly may be constructed.
Figure 36:
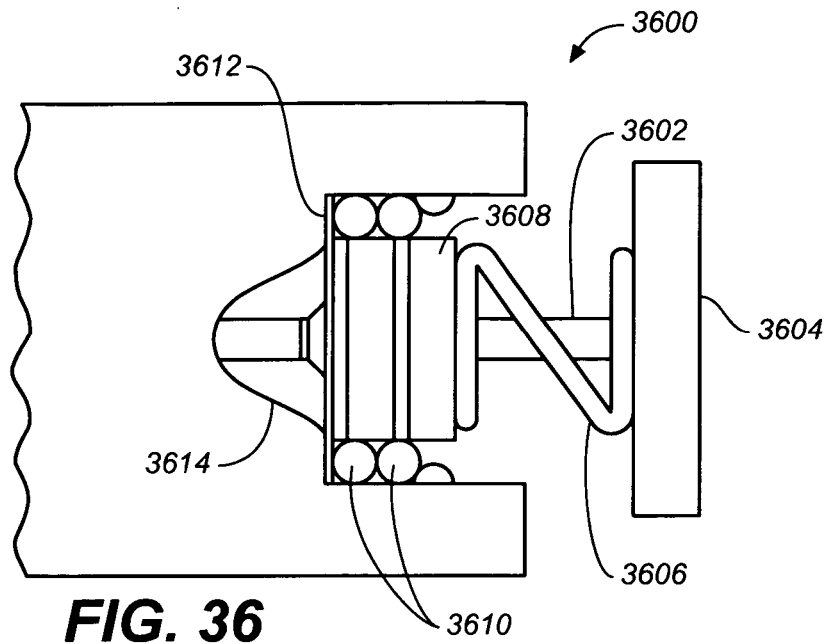
FIG. 36 provides an illustrative variation of a suitable dispensing member assembly.

Sealing around the dispensing member may also be improved with the use of one or more seals around the dispensing member itself, as described briefly above. FIGS. 34-36 show illustrative variations of such seals. Shown in FIG. 34A is plunger assembly (3400). Plunger assembly (3400) comprises plunger body (3404), plunger head (3402), spring (3406), retaining ring (3408), O-rings (3410) and diaphragm (3412). A cross-sectional view of these components is shown in FIG. 34B, taken along line B-B. These components may be made of any suitable material, and it is desirable that they be made out of drug compatible material as described above. Distances d1, d2, and d3 shown in FIG. 34B may be any suitable length, and their lengths largely depend on the overall device design and construction. For example, d1 may be from about 0.2 inches to about 0.5 inches d2 may be from about 0.5 inches to about 1 inch and d3 may be from about 1 inch to about 1.6 inches. Illustrative lengths for d1, d2, and d3 for the plunger assembly shown in FIG. 34B are 0.375 inches, 0.690 inches, and 1.224 inches. The O-rings may have any suitable diameter, and the diameter of the O-rings largely depends on the diameter of the plunger body. In some variations, the O-ring has an inner diameter of about 0.218 inches and an outer diameter of about 0.257 inches. The entire plunger assembly (3400) may be removable from the device, or any portion of the assembly (3400), such as O-rings, etc. may be removable from the plunger body.

It should be understood that while the plunger head (3402) shown in FIGS. 34A-B is generally rounded, any plunger head geometry, such as those described above, may be used. Similarly, while the spring shown in FIGS. 34A-B is generally helically, any of the springs previously disclosed may be used. In addition, any number of springs may be used, any number of O-rings may be used, and any number of diaphragms may be used. FIG. 35 provides an illustrative depiction of a how a plunger assembly having multiple O-rings and multiple diaphragms may be constructed. Shown there is plunger assembly (3500) having plunger body (3502), plunger head (3504), diaphragms (3510, 3512, and 3514), and O-rings (3506 and 3508). As shown by the arrows, a first diaphragm (3512) may be slid over the plunger body (3502) until a suitable location is reached. Then first O-ring (3506) may be slid over the plunger body (3504) until it abuts first diaphragm (3512). Second diaphragm (3510) is then slid over the plunger body (3506) until it abuts first O-ring (3506). Any number of additional O-rings and diaphragms may be added to the plunger assembly in a like fashion. In some variations, it may be desirable to micro-blast at least a portion of the plunger body (3502) where bonding of one or diaphragms will occur, as shown in FIG. 35 by the dotted section.

Another variation of a plunger assembly having a seal is shown in FIG. 36. In the variation shown there, plunger assembly (3600) comprises plunger body (3602), plunger head (3604), spring (3606), and retaining ring (3608) housing a double O-ring seal (3610). Also shown is diaphragm (3612). In this variation, diaphragm (3612) is attached or otherwise bonded to plunger (3602), and is made of a flexible material (e.g., an elastomer, such as silicone, etc.). The diaphragm (3612) is also attached or otherwise bonded to retaining ring (3608) at its edges or periphery. As the plunger body (3602) is displaced, the diaphragm (3612) flexes, and assumes a convex shape, which may expand into a portion, or all, of the diaphragm housing (3614). The diaphragm housing (3614) may be a separate housing, or may be an aperture or other hole formed in the nozzle block or portion itself.

Actuators are also described here, and any suitable actuator may be used in combination with any of the dispensing members described just above. For example, the actuator may be a piezoelectric actuator, a spring, a solenoid, a magnet, a motor, a shape-memory alloy actuator, or a compressed gas actuator. In some variations, a shape memory alloy actuator is used, such as a nickel titanium alloy actuator. In other variations, the actuator is a piezoelectric actuator.

Figure 37A:
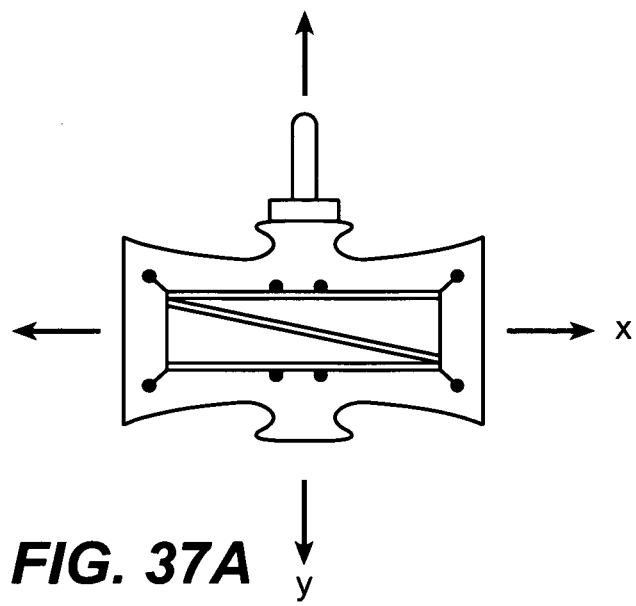
FIG. 37A illustrates piezoelectric crystal expansion and FIG. 37B depicts how a piezoelectric crystal may be used as an actuator for any of the devices described here.

Piezoelectric actuators are capacitive transducers that expand when voltage is applied to them. The displacements of piezoelectric transducers are typically small (e.g., typically less than 10 μm), while the forces they generate can be quite large (1 N to 1000 N). Typically, the expansion of a piezoelectric transducer is limited by piezo size, but large displacements (which result in larger velocities) are desirable. One way to amplify the motion of a piezoelectric transducer is to use flexural hinges, as depicted in FIGS. 37A and B. As shown in FIG. 37A, expansion of the piezo in the horizontal direction (x-x) leads to a push or pull of hinges in the vertical direction (y-y).

Figure 37B:
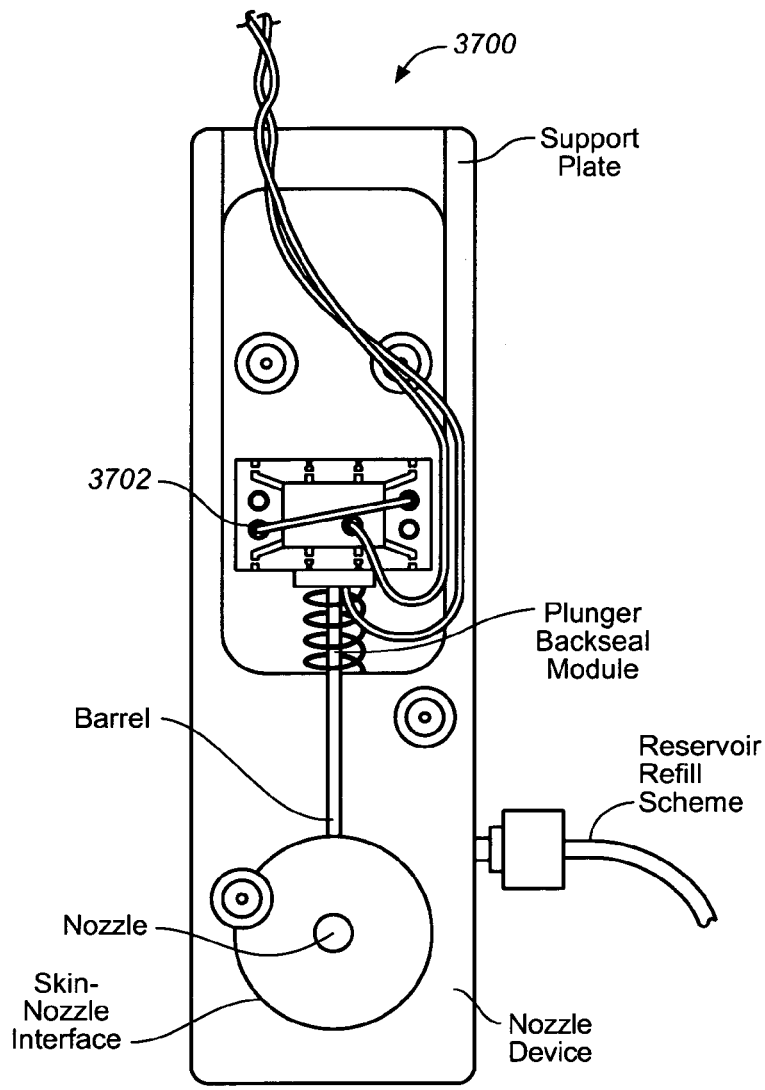

FIG. 37B provides an illustrative depiction of a piezoelectric actuator that may be incorporated into the devices described here for actuating a dispensing member. Shown there is device (3700) comprising piezoelectric actuator (3702), here in the form of a piezoelectric crystal with flexural hinges. When the crystal expands, it depresses plunger (3704), forcing drug out of nozzle (3706). Any suitable amplified (hinged) piezoelectric actuator may be used, such as those manufactured by CEDRAT, DSM, PI, Noliac, and the like.

Figure 38:
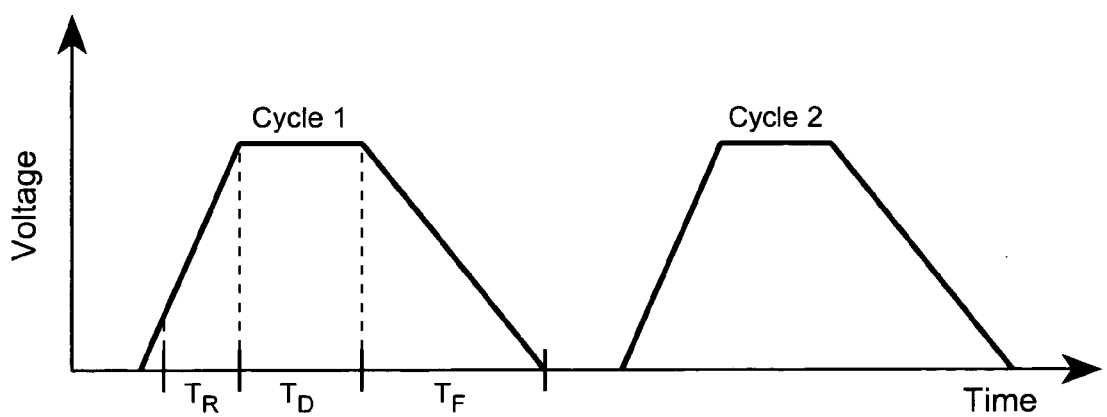
FIG. 38 provides a voltage pulse time curve for a piezoelectric actuator.

Shown in FIG. 38 is a voltage pulse time curve for a piezoelectric actuator. Shown there is the rise time ($T_R$), the dwell time ($T_D$), and the fall time ($T_F$). Illustrative rise times are typically less than about 10 ms, more typically less than about 1 ms, and preferably less than about 10 μs. Illustrative dwell times are typically between about 1 ms to about 60 s, and the fall time can vary from about 1 ms to about 100 ms. The voltage level during the dwell time can vary from about 25V to about 500 V, and more typically, from about 60V to about 150V.

Figure 39:
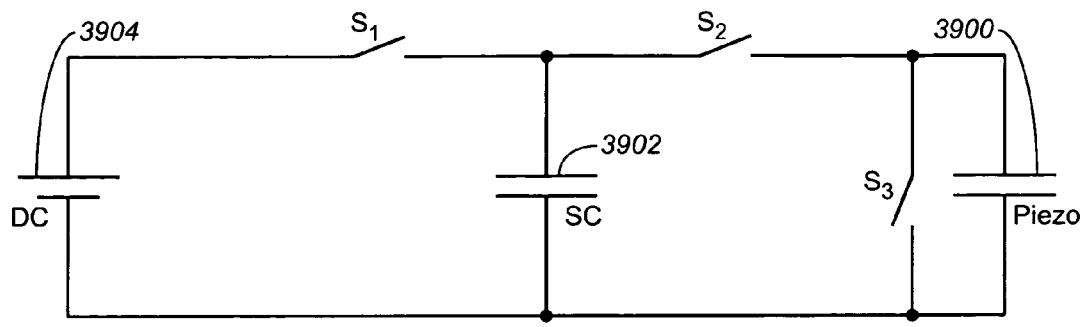
FIG. 39 provides an illustrative schematic of a circuit that may be used to generate the pulsed power to drive any of the piezoelectric actuators described here.

FIG. 39 provides an illustrative schematic of a circuit that may be used to generate the pulsed power to drive any of the piezoelectric actuators described here. Shown there are switches $S_1$, $S_2$, and $S_3$, piezoelectric actuator (3900), storage capacitor (3902) and DC power supply (3904). Switches $S_1$, $S_2$, and $S_3$ may be any suitable switches, e.g., MOSFET switches, bipolar junction transistor (BJT) switches, or silicon controlled rectifiers, some combination thereof, or the like, and may be opened or closed using one or more additional switches and/or amplifiers. During the first stage of a typical cycle, $S_1$ is closed while $S_2$ and $S_3$ are open, serving to transfer energy from the DC power supply to the storage capacitor. The DC power supply may be any suitable power supply (e.g., a 60-300V DC power supply). During the second stage, $S_1$ and $S_3$ are open while $S_2$ is closed, serving to transfer the stored energy to the piezoelectric actuator in a short period of time. $S_3$ remains open for the period of the dwell time while $S_1$ and $S_2$ stay be open or closed. The third stage, initiating the piezoelectric voltage fall, is accomplished by opening $S_2$ while $S_3$ is closed. In some variations, S1 is closed as the piezoelectric voltage falls back to ground, enabling the storage capacitor to be charged while the piezoelectric discharges, thereby shortening the time between pulses. This three-stage cycle can be repeated for any number of pulses and the time between pulses may be set by controlling the opening or closing of any or all of switches $S_1$, $S_2$, and $S_3$.

Figure 40:
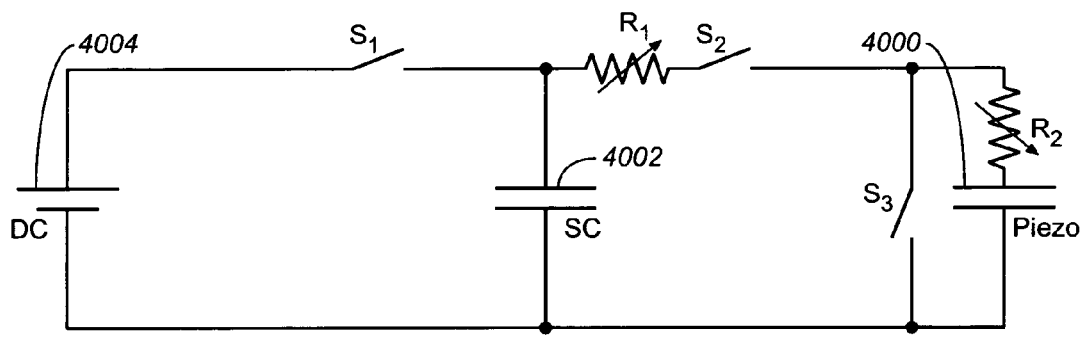
FIG. 40 provides a schematic of a circuit that may be used to control the rise and/or fall times of the voltage pulse applied to a piezoelectric actuator using variable resistors.
Figure 41:
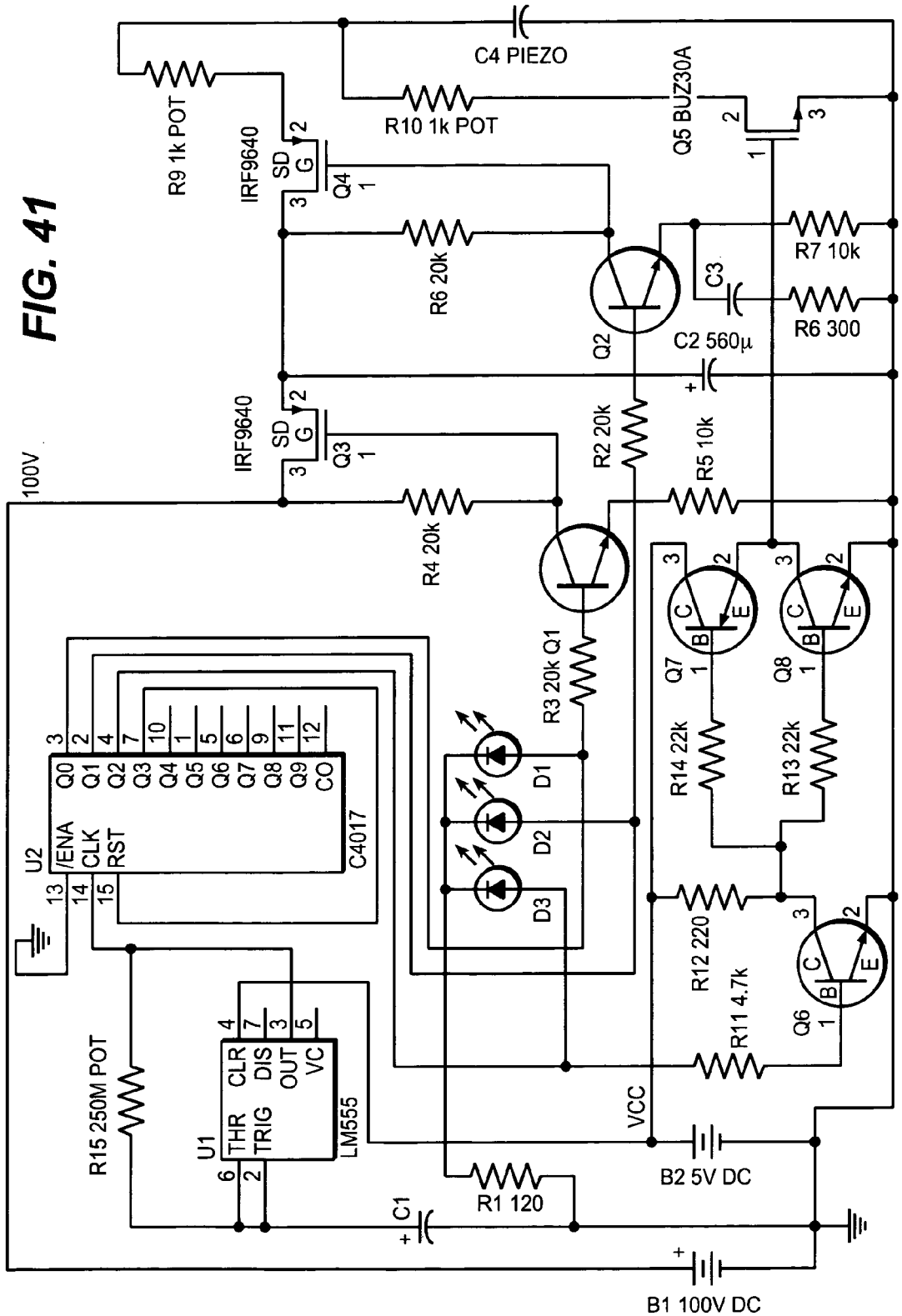
FIG. 41 is an illustrative circuit diagram that may be used to provide a pulsed power to a piezoelectric actuator having variable resistors as shown in FIG. 40.
Figure 43C:
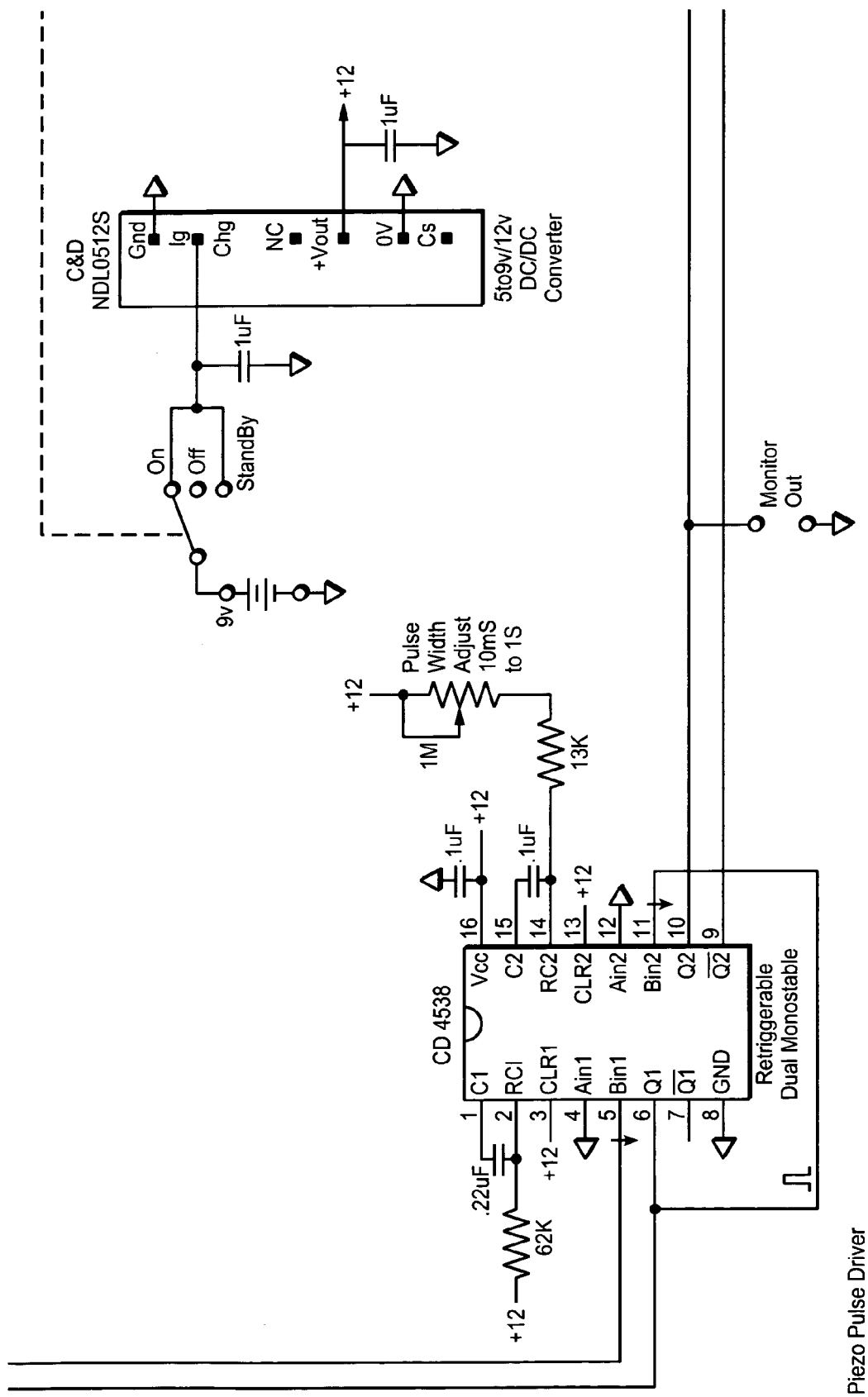
Figure 43D:
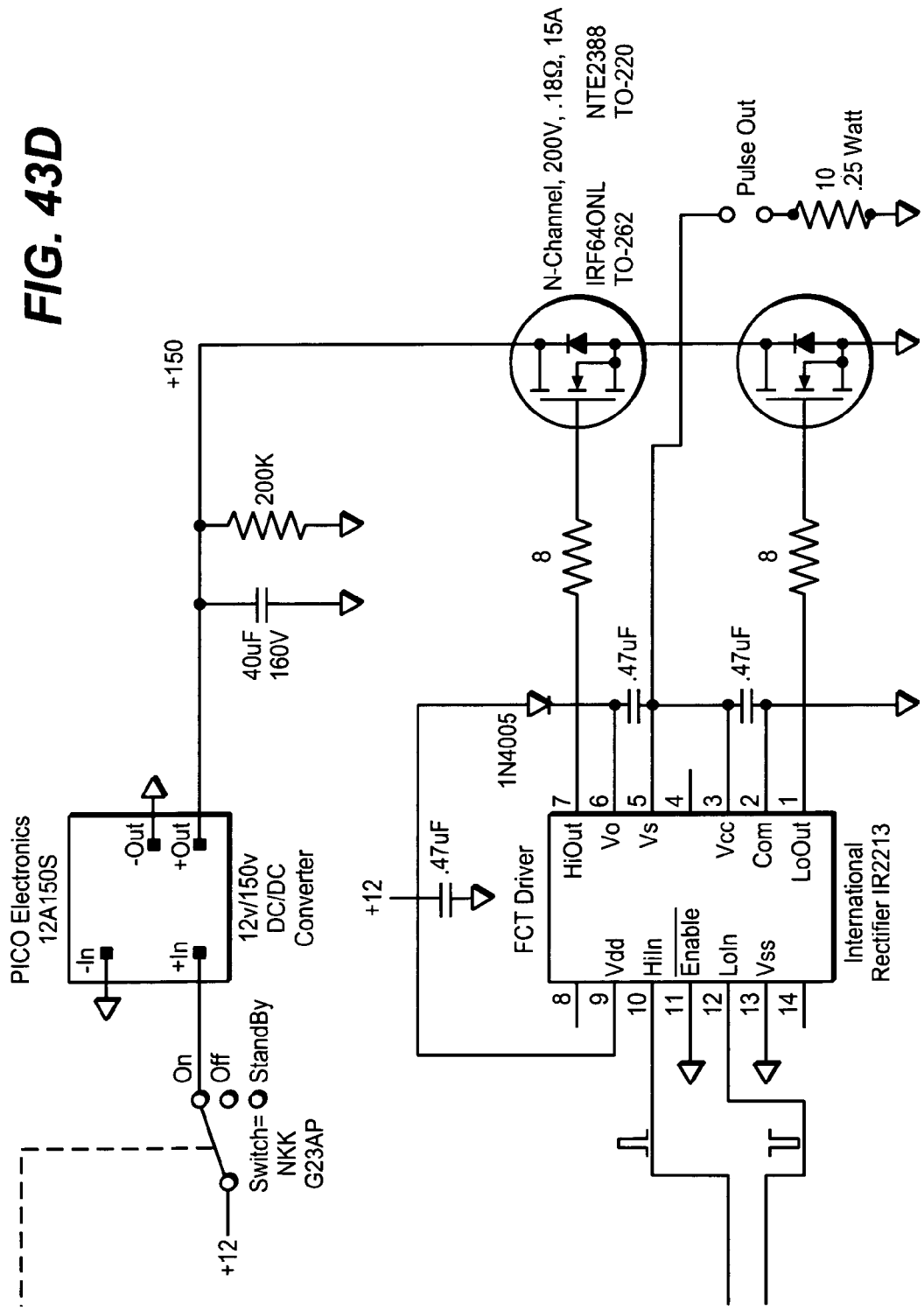

FIG. 40 provides a schematic of a circuit that may be used to control the rise and/or fall times of the voltage pulse applied to the piezoelectric actuator using variable resistors. Shown there is piezoelectric actuator (4000), storage capacitor (4002), DC power supply (4004), switches, $S_1$, $S_2$, and $S_3$, and variable resistors $R_1$ and $R_2$. In this variation, the resistors serve to control the current flow to the piezoelectric actuator (4000), which in turn serves to modulate the rise and fall times of the voltage pulse. The DC power supply (4004) may be a high voltage power supply, such as the power supplies described just above, and the switches may be any suitable switches as described above. The variable resistors can be digital potentiometers that allow for the resistance value to be pre-set, either manually or automatically via a microprocessor or the like. The variable resistors may be implemented using either series or parallel configurations. FIG. 41 is an illustrative schematic of a circuit that may be used to provide a pulsed power to the piezoelectric actuator (4000) having variable resistors shown in FIG. 40. In this circuit, the storage capacitor C2 is charged from the power supply B1. Switches Q3, Q4, and Q5 may be opened or closed as described above to generate the voltage pulse(s) for the piezoelectric actuator C4. The piezoelectric actuator C4 is discharged when switch Q5 is closed.

Figure 42:
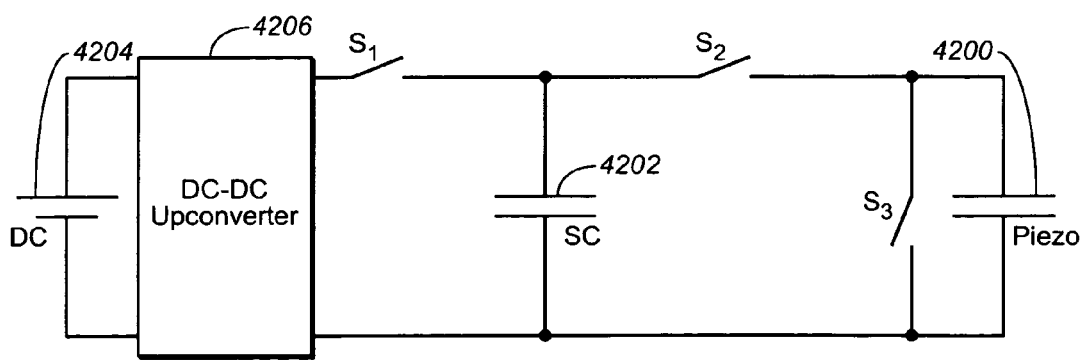
FIG. 42 provides a schematic of a circuit having a low voltage battery.

The voltage pulses described above may also be accomplished using low a voltage battery. Since typical batteries operate at low voltages (0.5V to 10V DC), and the piezoelectric actuator typically requires an operating voltage of about 90V to about 150V, a DC-DC upconversion or voltage boost is required. Accordingly, in variations where a low voltage battery is employed, the circuits include a voltage up conversion so that voltages sufficient to operate the piezoelectric actuator may be generated. One such variation is shown in FIG. 42. Shown there is piezoelectric actuator (4200), storage capacitor (4202), DC power supply (4204), and DC-DC upconverter (4206). Switches $S_1$, $S_2$, and $S_3$ are also shown. In this variation, DC power supply is a low voltage power supply (e.g., less than about 10V), and a DC-DC upconverter (4206) is used to generate the pulsed power necessary to drive the piezoelectric actuator (4200).

The upconverter (4206) is shown as a single module, but multiple modules may be used, and the upconversion can occur in a single, or in multiple stages. In some variations, the DC-DC upconverter (4206) is of high efficiency for longer battery life, small to enable portable applications, programmable to set the output voltage, or some combination thereof. The DC-DC upconverter (4206) may employ or comprise an inductor based boost circuit or a charge pump circuit that uses capacitors, or a Cockroft-Walton circuit that uses capacitors and diodes. In some variations, the inductor based boost circuit is a switching mode power circuit. The switching mode power circuit may be a boost circuit or a buck-boost circuit, a flyback converter circuit or a push-pull circuit, a Cuk circuit or a single ended primary inductor converter (SEPIC), or any other similar and suitable circuit, which are well known in the art.

FIGS. 43 and 43A-D provide an illustrative circuit implementation of the schematic circuit shown in FIG. 42 using two off-the-shelf DC upconverters. The first upconverter, manufactured by C&D Technology, amplifies the voltage from 1.5-9V to 12V, and the second upconverter, manufactured by Pico Electronics, amplifies the output of the first upconverter from 12V to 150V. The circuit shown in FIGS. 43 and 43A-D include modules that allow repetition rate and pulse width to be preset. An oscillator chip, binary counter chip, and a repetition rate switch serve to preset the repetition and pulse widths.

Figure 44:
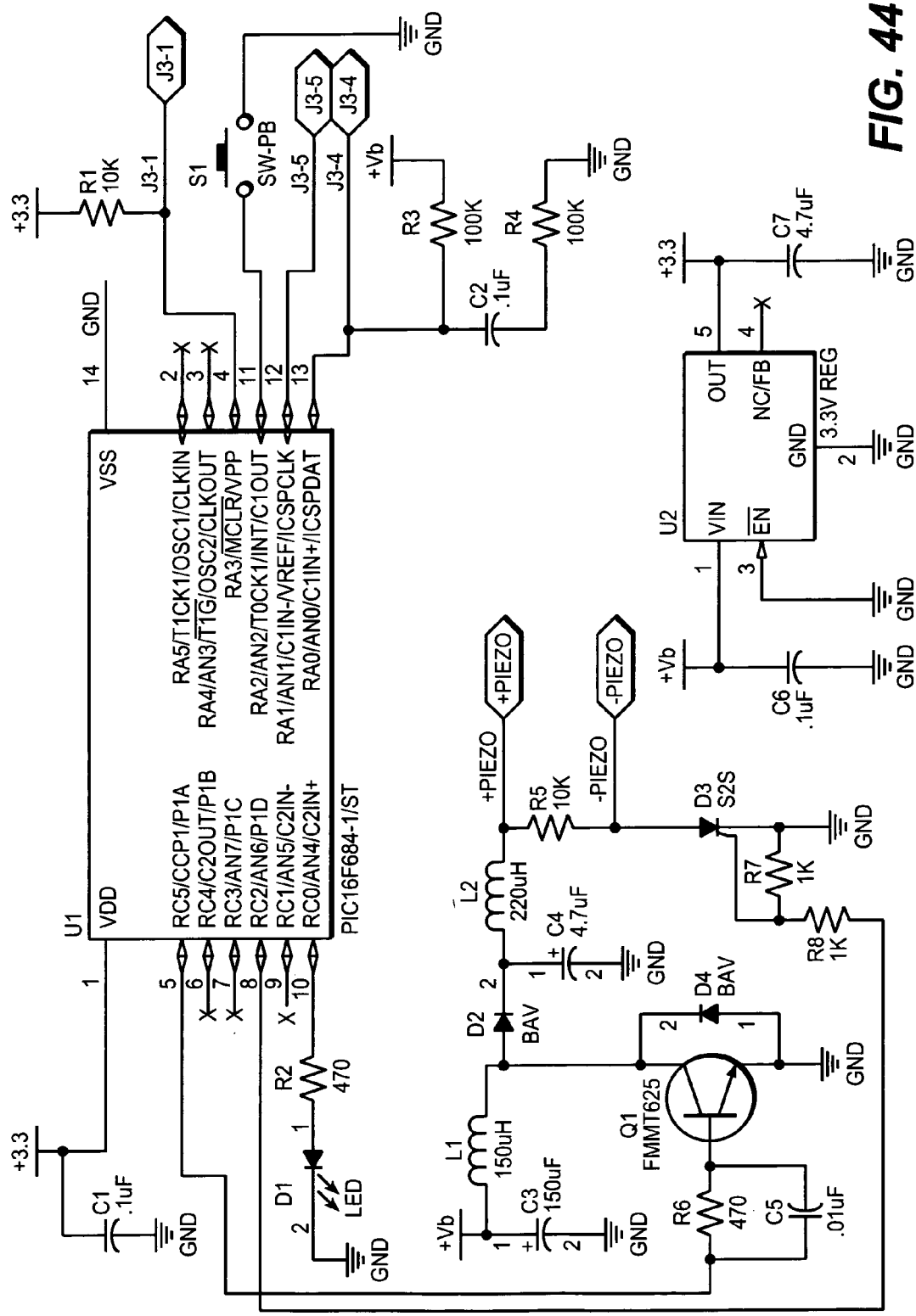
FIG. 44 provides an illustrative schematic of a circuit that uses a custom boost converter for DC-DC upconversion, a microprocessor for circuit control, and a silicon controlled rectifier switch.

FIG. 44 provides an illustrative schematic of a circuit that may be used to drive the piezoelectric actuator. This circuit includes a microprocessor and an inductor-based switching mode DC voltage upconversion module. The microprocessor controls the output pulse characteristics (e.g., repetition rate, output voltage, pulse width, pulse fall time, etc.) and may also control the switching mode power supply boost converter transistor. The microprocessor may control these variables irrespective of the type of switch used in the circuit. Microprocessors used in any of the described circuits may also be used for programmability purposes, e.g., to control timing of drug delivery, dosage level, and the like. A silicon controlled rectifier D3 is used as a switch to transfer energy from the storage capacitor to the piezoelectric actuator via an inductor L2. In the variation shown here, a lithium ion battery is used, although other primary (i.e., single use) or secondary (i.e., rechargeable) batteries with suitable lifetimes may also be employed. In addition to lithium ion batteries, suitable batteries, may for example, be selected from the group consisting of zinc-air batteries, lithium manganese oxide batteries, zinc manganese oxide batteries, lithium sulfuryl chloride batteries, lithium polymer batteries, lithium vanadium oxide batteries, and nickel metal hydride batteries. Of course, any suitable battery may be used.

In variations where a piezoelectric actuator is used, the device may further comprise at least one noise-reduction element, which may cover at least a portion of the piezoelectric actuator, or may be closely adjacent thereto. The noise-reduction element may be selected from the group consisting of acoustic foam, sound absorbing silicone, acoustic rubber, a suspension of micro hollow glass spheres, or a combination of any of the above.

E. Drugs for Delivery

Any suitable drug, or active agent, (most typically in liquid form) may be delivered with the devices described here. In some variations, it may be desirable to deliver those drugs that are typically used over long periods of time, e.g., those drugs to treat chronic pain or chronic conditions, and the like. Similarly, it may be desirable to deliver those drugs that are typically delivered in a subcutaneous, intramuscular, or other injectable fashion, in order to reduce pain and improve patient compliance. Delivery of other types of drugs may also be desirable.

Suitable active agents for use with the methods, devices, and kits described here are not limited by therapeutic category, and can be, for example, analgesics, anti-emetics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, calcium channel blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, potassium channel activators, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof. Similarly, the active agent can be a cytokine, a peptidomimetic, a peptide, a protein, a toxoid, a serum, an antibody, a vaccine, a nucleoside, a nucleotide, a portion of genetic material, a nucleic acid, or a mixture thereof.

Specific, non-limiting examples of suitable active agents are: abatacept; abciximab; acarbose; acetyl cysteine; acetylcholine chloride; acutretin; acyclovir; adalmumab; adenosine; agalsidase beta; alatrofloxacin; albendazole; albumin, human; albuterol; aldesleukin; alefacept; alemtuzumab; alendronate; alglucerase; alprostadil; alteplase; alvimopan; amantadine hydrochloride; ambenomium; amifostine; amikacin; amiloride hydrochloride; aminocaproic acid; aminogluthemide; amiodarone; amlodipine; amoxicillin; amphetamine; amphotericin B; anakinra; anidulafungin; antihemophilic factor (human); antihemophilic factor (porcine); antihemophilic factor (recombinant); antithrombin III; antivenin crotalidae polyvalent ovine; apomorphine; aprotinin; argatroban; arsenic trioxide; asparaginase; atenolol; atorvastatin; atovaquone; atracurium besylate; atropine; azacitidine; azithromycin; azithromycin; aztreonam; bacitracin; baclofen; basiliximab; BCG vaccine; becalermin; beclomethsone; belladona; benezepril; benzonatate; bepridil hydrochloride; beractant; betamethasone; bevacizumab; bicalutanide; bivalirudin, bleomycin sulfate; bortezomib; botulinum toxin type A; budesonide; bupropion; busulphan; butenafine; calcifediol; calciprotiene; calcitonin human; calcitonin salmon; calcitriol; camptothecan; candesartan; capecitabine; capreomycin sulfate; capsaicin; carbamezepine; carboplatin; carmustine; carotenes; caspofungin; cefamandole nafate; cefazolin sodium; cefepime hydrochloride; cefixime; cefonicid sodium; cefoperazone; cefotetan disodium; cefotoxime; cefoxitin sodium; ceftazidime; ceftizoxime; ceftriaxone; cefuroxime axetil; celecoxib; cephalexin; cephapirin sodium; cerivistatin; cetrizine; cetuximab; chlorothiazide sodium; chlorpheniramine; cholecalciferol; cholera vaccine; chondroitin sulfate sodium; chorionic gonadotropin; cidofovir; cilostazol; cimetidine; cinnarizine; ciprofloxacin; cisapride; cisatracurium besylate; cisplatin; cladribine; clarithromycin; clemastine; clidinium bromide; clindamycin and clindamycin derivatives; clomiphene; clomipramine; clondronate; clopidrogel; codeine; coenzyme Q10; colistimethate sodium; colistin sulfate; cortocotropin; cosyntropin; cromalyn sodium; cyclobenzaprine; cyclosporine; cytarabine; daclizumab; dactinomycin; daltaperin sodium; danaproid; danazol; dantrolene; daptomycin; darbopoetin alfa; decitabine; deforoxamine; denileukin diftitox; desmopressin; dexchlopheniramine; diatrizoate megluamine and diatrizoate sodium; diclofenac; dicoumarol; dicyclomine; didanosine; digoxin; dihydro epiandrosterone; dihydroergotamine; dihydrotachysterol; diltiazemi; dirithromycin; dobutamine hydrochloride; domase alpha; docetaxel; donepezil; dopamine hydrochloride; doxacurium chloride; doxorubicin; drotrecogin alfa; edentate trisodium; editronate disodium; efalizumab; efavirenz; efuvirtide; elanaprilat; enelapril; enkephalin; enoxacin; enoxaparin sodium; ephedrine; epinephrine; epirubicin hydrochloride; epoetin alpha; eposartan; eprostenol sodium; eptacpq alpha; eptifibatide; ergocalciferol; ergotamine; ertapenum sodium; erythromycin; esmolol; esmolol hydrochloride; esomeprazole sodium; essential fatty acid sources; estradiol; estrogen; etanercept; etodolac; etomidate; etonogestrel; etoposide; exenatide; factor VIII kogenate; factor IX; famiciclovir; famotidine; felodipine; fenofibrate; fentanyl; fexofenadine; fibroginogen; filgrastim; finasteride; flucanazole; fludarabine; flumazenil; fluorouracil; fluoxetine; flurbiprofen; fluvastatin; follitropin alfa; follitropin beta; fomepizole; fondaparinux sodium; foscamet sodium; fosphenytion; frovatriptan; fulvestrant; furazolidone; gabapentin; ganciclovir; gemcitabine hydrochloride; gemfibrozil; gemtuzumab ozogamicin; gentamycin; glatiramer acetate; glibenclamide; glipizide; globulin, rabies immune; glucagon; glyburide; glycine; glycopyrolate; glymepride; GnRH; gonadorelin; gonadotropin releasing hormone and synthetic analogs thereof; goserelin acetate; granulocyte colony stimulating factor; granulocyte-macrophage stimulating factor; grepafloxacin; griseofulvin; growth hormone-bovine; growth hormones-recombinant human; halofantrine; hemin; hemophilus B conjugate vaccine; heparin calcium; heparin magnesium; heparin sodium; hepatitis A virus vaccine inactivated; hepatitis B virus vaccine inactivated; hetastarch; hydroxycodone hydrochloride; hydroxycortisone hemisuccinate; hyoscyamine hydrobromide; ibuprofen; ibutilide fumarate; ifosfamide; imiglucerase; immunoglobulin, anti-cytomegalovirus; immunoglobulin, anti-thymocyte; indomethancin, meglumine salt; indinavir sulfate; indomethacin sodium; infliximab; influenza virus vaccine; insulin aspart; insulin detemir; insulin glargine; insulin glulisine; insulin isophane; insulin lispro; insulin NPH; insulin procine; insulin-human; interferon alfa-2A; interferon alfa-2b; interferon alfacon; interferon beta 1A; interferon beta 1B; interferon gamma; interleukin-2; interleukin-3; iodine 131 tositumomab; ipratropium bromide isofosfamide; irbesartan; irinotecan; isosorbide dinitrate isotreinoin; itraconazole; ivermectin; japanese encephalitis virus vaccine; ketoconazole; ketorolac; lamivudine; lamotrigine; lanosprazole; leflunomide; lepirudin; leucovorin calcium; leuprolide acetate; levofloxacin; lincomycin and lincomycin derivatives; lisinopril; lobucavir; lomefloxacin; loperamide; loracarbef; loratadine; lovastatin; L-thryroxine; lutein; lutropin; lycopene; mannitol; measles virus vaccine; medroxyprogesterone; mefepristone; mefloquine; megesterol acetate; melphalan hydrocholoride; meningococcal vaccine; menotropins; mephenzolate bromide; meropenem; mesalmine; metformin hydrochloride; methadone; methanamine; methotrexate; methoxsalen; methscopolamine; methylprednisolone; metronidazole; metroprolol; mezocillin sodium; miconazole; micafungin; midazolam; miglitol; milrinone; minoxidil; mitoxantrone; mivacurium chloride; montelukast; morotocog alfa; morphine tartrate; mumps viral vaccine; nabumetone; nalbuphine; naloxone hydrochloride; naratiptan; natalizumab; nedocromil sodium; nelfinavir; neostigmine bromide; neostigmine methyl sulfate; nesiritide; neutontin; nicardipine; nicorandil; nifedipine; nilsolidipine; nilutanide; nisoldipine; nitrofurantoin; nizatidine; nonacoq alpha; norepinephrine bitartrate; norepinephrine hydrochloride; norethindrone enanthate; norfloxacin; octocog alpha; octreotide acetate; ofloxacin; olpadronate; omalizumab; omeprazole; ondansetron; oprevelkin; osteradiol; oxaliplatin; oxaprozin; oxytocin; paclitaxel; palivizumab; palonosetron hydrochloride; pamidronate disodium; pancuronium bromide; panitumumab; paricalcitol; paroxetine; pefloxacin; pegfilgrastim; peginterferon alfa 2A; peginterferon alfa 2B; pegvisomant; pemetrexed; penicillin G procaine; pentagastrin; pentamindine isethionate; pentazocine; pentobarbital; pentostatin; pentoxifylline; periciclovir; perphenazine; phentolamine mesylate; phenylalanine; physostigmine salicylate; pioglitazone; piperacillin sodium; pizofetin; plague vaccine; platelet derived growth factor-human; pneumococcal vaccine polyvalent; poliovirus vaccine inactivated; poliovirus vaccine live (OPV); polymixin B sulfate; pralidoxine chloride; pramlintide; pravastatin; prednisolone; pregabalin; probucol; progesterone; propenthaline bromide; propofenone; pseudoephedrine; pyridostigmine; pyridostigmine bromide; pyrilamine; quinine formate; rabeprazole; rabies vaccine; raloxifene; rasburicase; refocoxib; repaglinide; residronate; reteplase; ribavarin; rifabutine; rifampin sodium; rifapentine; rimantadine hydrochloride; rimexolone; ritanovir; rituximab; rizatriptan; rocuronium bromide; ropivacaine; rosigiltazone; rotavirus vaccine; salmetrol xinafoate; saquinavir; sargramostim; selenious acid; sertraline; sibutramine; sildenafil citrate; simvastatin; sincalide; sirolimus; small pox vaccine; solatol; somatostatin; somatropin; sparfloxacin; spectinomycin; spironolactone; stavudine; streptokinase; streptozocin; succinylcholine chloride; sulbactam sodium; sulfadiazine; sumatriptan; suxamethonium chloride; tacrine; tacrine hydrochloride; tacrolimus; tamoxifen; tamsulosin; targretin; tazarotene; telmisartan; tenecteplase; teniposide; terbinafine; terbutaline sulfate; teriparatide; teriparatide acetate; terzosin; testosterone; tetrahydrocannabinol; thiopeta; tiagabine; ticarcillin; ticlidopine; tigecycline; tiludronate; timolol; tinzaparin sodium; tirofiban; tissue type plasminogen activator; tizanidine; TNFR:Fc; TNK-tPA; topiramate; topotecan; toremifene; tramadol; trandolapril; trastuzumab; tretinoin; trimetrexate gluconate; triptorelin; troglitazone; trospectinomycin; trovafloxacin; tubocurarine chloride; tumor necrosis factor; typhoid vaccine live; ubidecarenone; urea; urofollitropin; urokinase; vaccines (all types); valaciclovir; valsartan; vancomycin; varicella virus vaccine live; vasopressin and vasopressin derivatives; vecoronium bromide; venlafaxine; vertoporfin; vigabatrin; vinblastin; vincristine; vinorelbine; vitamin A; vitamin B12; vitamin D; vitamin E; vitamin K; warfarin sodium; yellow fever vaccine; zafirlukast; zalcitabine; zanamavir; zidovudine; zileuton; zolandronate; zoledronic acid; zolmitriptan; zolpidem; zopiclone; and pharmaceutically acceptable salts, isomers and derivatives thereof; and mixtures thereof.

II. Methods

Methods for needleless drug delivery using microjet devices are also described here. In general, the methods comprise placing one of the described drug delivery devices on the skin. When the devices are configured for use in a patch-like fashion, the method may also comprise a step of peeling off a protective layer or lining on the adhesive surface, so that the adhesive may be placed on the skin. The methods may also involve filling the reservoir with drug (initially or for refill).

When devices having user interface buttons are used, the methods may further comprise depressing the user interface button. When the device is a modular drug delivery device, the user may further replace one or more components of the device (e.g., a battery, a reservoir, a nozzle), as described above. In addition, when modular devices are used, the methods may further include coupling and/or locking the modules together.

III. Kits

Also described here are kits. In some variations the kits comprise two modules in packaged combination. For example, the kit may comprise a first module comprising a drug reservoir and a nozzle in fluid communication with the drug reservoir and a second module comprising an actuator and a power supply, where the first and second modules are capable of being releasably coupled to form a modular drug delivery device. One or more first modules or one or more second modules may be packaged together in such a fashion. In other variations the kits comprise a single device and a disposable reservoir, pre-filled with a volume of drug for a given therapy. One or more pre-filled reservoirs may be included in the kit.

The kits described here may further comprise one or more batteries (or other sources of power), a battery charger, one or more syringes for re-filling the reservoir with drug, and/or instructions for use. The kits may be packaged in any suitable fashion. In some variations, the kit components are packaged in a single package that has been vacuum sealed in order to reduce the formation of bubbles during shipping.

What we claim is:

1. A modular drug delivery device comprising:
   a first module comprising a drug reservoir and a nozzle having a first end and a second end, where the first end is in fluid communication with the drug reservoir, the first module having a basal surface that contacts skin during use, and where the second end of the nozzle terminates at the basal surface to define a skin-nozzle interface; and
   a second module comprising an actuator and a power supply, wherein the power supply provides power to the actuator and wherein the first and second modules are capable of being releasably coupled to form a modular drug delivery device, and wherein when the first and second modules are coupled, the actuator is capable of acting on a dispensing member causing it to dispense a drug in liquid form from the nozzle at a velocity sufficient to penetrate skin.

2. The modular drug delivery device of claim 1, wherein the actuator is selected from the group consisting of a piezoelectric actuator, a spring, a solenoid, a magnet, a motor, and a compressed gas actuator.

3. The modular drug delivery device of claim 2, wherein the actuator is a piezoelectric actuator.

4. The modular drug delivery device of claim 3, wherein the piezoelectric actuator is controlled by one or more switches that are operated to apply a voltage pulse to the piezoelectric actuator.

5. The modular drug delivery device of claim 1, wherein the dispensing member is a plunger.

6. The modular drug delivery device of claim 5, wherein the plunger has one or more grooves thereon.

7. The modular drug delivery device of claim 1, wherein the reservoir is refillable.

8. The modular drug delivery device of claim 1, wherein the reservoir contains a pre-filled amount of drug and is configured for a single-use.

9. The modular drug delivery device of claim 1, wherein the device is programmable.

10. The modular drug delivery device of claim 1, wherein at least a portion of the device is made of a hydrophilic material or is coated with a hydrophilic agent.

11. The modular drug delivery device of claim 1, further comprising a locking mechanism to temporarily lock the first and second modules together.

12. The modular drug delivery device of claim 1, wherein the first module has a basal surface and a top surface and further comprises an adhesive on at least a portion of its basal surface to provide for temporary device attachment to the skin.

13. The modular drug delivery device of claim 1, wherein the power supply is a battery.

14. The modular drug delivery device of claim 13, wherein the battery is a rechargeable battery.

15. The modular drug delivery device of claim 1, wherein the second module further comprises a field programmable gate array.

16. The modular drug delivery device of claim 1 further comprising a display.

17. The modular drug delivery device of claim 1 further comprising at least one LED.

18. The modular drug delivery device of claim 1 further comprising at least one element to reduce leakage of drug around the dispensing member.

19. The modular drug delivery device of claim 18 wherein the at least one element to reduce leakage of drug around the dispensing member comprises a diaphragm coupled to the dispensing member.

20. The modular drug delivery device of claim 19 further comprising at least one retaining ring, wherein at least a portion of the diaphragm is coupled with the retaining ring.

21. The modular drug delivery device of claim 19 further comprising at least one elastomeric sealing member.

22. The modular drug delivery device of claim 1 wherein the second module further comprises a user interface switch.

23. The modular drug delivery device of claim 1 wherein the first module is configured for a single-use.

24. The modular drug delivery device of claim 1 wherein the first and second modules are uniquely mateable for a given therapy.

25. The modular drug delivery device of claim 1 wherein the first module comprises more than one nozzle.

26. The modular drug delivery device of claim 1 wherein the nozzle has a variable diameter at its distal opening.

27. The modular drug delivery device of claim 1 wherein the nozzle is an interchangeable nozzle.

28. A microjet drug delivery device having a top surface and a basal surface for needleless drug delivery across a skin surface comprising:
a drug reservoir;
a nozzle having a first end and a second end, the first end of the nozzle is in fluid communication with the drug reservoir where the second end of the nozzle terminates at the basal surface of the device, the nozzle second end contacts skin during use to define a skin-nozzle interface;
a dispensing member; and
an actuator, wherein the actuator is configured to act on the dispensing member causing it to dispense an amount of drug in liquid form from the second end of the nozzle at the skin-nozzle interface at a velocity sufficient to penetrate skin, and wherein the device comprises at least one feature that reduces leakage of the drug.

29. The microjet device of claim 28, wherein at least a portion of the device has a geometry that enhances nozzle contact with skin in order to reduce lateral leakage of drug.

30. The microjet device of claim 28, further comprising a flange disposed about at least a portion of the dispensing member.

31. The microjet device of claim 28, wherein the dispensing member is a plunger.

32. The microjet device of claim 28, wherein the at least one element to reduce leakage of drug is configured to reduce leakage around the dispensing member.

33. The microjet device of claim 28, wherein at least a portion of the device adjacent the nozzle has a plurality of concentric rings formed at least partially thereon.

34. The microjet device of claim 28, further comprising at least two electrodes to measure capacitance of the skin.

35. The microjet device of claim 28, wherein the actuator is selected from the group consisting of a piezoelectric actuator, a spring, a motor, a solenoid, a magnet, and a compressed gas actuator.

36. The microjet device of claim 35, wherein the actuator is a piezoelectric actuator.

37. The microjet device of claim 28, wherein the device is programmable.

38. The microjet device of claim 28, wherein the device further comprises an adhesive on at least a portion of the basal surface to provide for temporary device attachment to skin.

39. The microjet device of claim 36, further comprising at least one noise-reduction element that is capable of reducing the sound generated by the piezoelectric actuator.

40. The microjet device of claim 39 wherein the at least one noise-reduction element is selected from the group consisting of acoustic foam, sound absorbing silicone, acoustic rubber, a suspension of micro hollow glass spheres, and a combination thereof.

41. The microjet device of claim 28, wherein a portion of the device is made of a hydrophilic material or is coated with a hydrophilic agent.

42. The microjet device of claim 28, wherein the reservoir is refillable.

43. The microjet device of claim 28, wherein the reservoir contains a pre-filled amount of drug and is configured for a single-use.

44. The microjet device of claim 28, further comprising a flow restrictor that governs the refill flow rate to the nozzle from the reservoir after drug has been dispensed therefrom.

45. The microjet device of claim 44 wherein the flow restrictor comprises a fluidic channel having an inner diameter between about 10 and about 200 µm.

46. The microjet device of claim 28 wherein the amount of drug dispensed in a single dispensing action is between about 5 nL and about 10 nL.

47. The microjet device of claim 28 wherein at least a portion of the nozzle is made from a polymeric material.

48. The microjet device of claim 28 further comprising more than one nozzle.

49. The microjet device of claim 28 wherein the nozzle has a variable diameter at its distal opening.

50. The microjet device of claim 28 wherein the nozzle is an interchangeable nozzle.

51. The microjet drug delivery device of claim 28
wherein the actuator is a piezoelectric actuator having an unexpanded state and an expanded stated and configured to act on the dispensing member when in the expanded state, causing it to dispense an amount of drug in liquid form from the nozzle at a velocity sufficient to penetrate skin, wherein the piezoelectric actuator is in electrical communication with a capacitor and at least one switch.

52. The microjet drug delivery device of claim 51 wherein the capacitor has a capacitance that is about 1.5 to about 10 times the capacitance of the piezoelectric actuator.

53. The microjet drug delivery device of claim 51 wherein the capacitor is charged to a voltage that is the same or higher than the desired final voltage of the piezoelectric actuator when it is in its expanded state.

54. The microjet drug delivery device of claim 51 wherein the switch is a solid state switch and is used at least to discharge the piezoelectric actuator to bring the piezoelectric actuator back to its unexpanded state.

55. The microjet drug delivery device of claim 51 further comprising more than one switch.

56. The microjet drug delivery device of claim 55 wherein the switches are not closed at the same time.

57. The microjet drug delivery device of claim 51 wherein the piezoelectric actuator is expanded within a specified rise-time, maintained in an expanded position for a specified dwell time, brought back to its unexpanded state within a specified fall time, and maintained in the unexpanded state for a specified time, forming a single cycle of operation.

58. The microjet drug delivery device of claim 51 further comprising a battery in electrical communication with the capacitor.

59. The microjet drug delivery device of claim 58 wherein the battery is selected from the group consisting of a lithium ion battery, a zinc-air battery, a lithium manganese oxide battery, a zinc manganese oxide battery, a lithium sulfuryl chloride battery, a lithium polymer battery, a lithium vanadium oxide battery, and a nickel metal hydride battery.

60. The microjet drug delivery device of claim 58 further comprising a DC upconversion module.

61. The microjet drug delivery device of claim 60 wherein the DC upconversion module comprises a switching mode power supply.

62. The microjet drug delivery device of claim 61 wherein the switching mode power supply is a boost converter.

63. The microjet drug delivery device of claim 60 wherein the DC upconversion module comprises a charge pump.

64. The microjet drug delivery device of claim 51 further comprising a microprocessor.

65. The microjet drug delivery device of claim 60 further comprising a microprocessor, where the microprocessor is configured to control the DC upconversion.

\* \* \* \* \*